United States Patent [19]

Brighty

[11] Patent Number: 5,266,569

[45] Date of Patent: Nov. 30, 1993

[54] AZATRICYCLO CARBOXYLIC ACIDS USEFUL AS ANTI-BACTERIAL AGENTS

[75] Inventor: Katherine E. Brighty, Groton, Conn.

[73] Assignee: Pfizer Inc, New York, N.Y.

[21] Appl. No.: 12,202

[22] Filed: Feb. 2, 1993

Related U.S. Application Data

[60] Division of Ser. No. 919,477, Jul. 24, 1992, Pat. No. 5,229,396, which is a division of Ser. No. 650,835, Feb. 4, 1991, Pat. No. 5,164,402, which is a continuation-in-part of Ser. No. 551,212, Jul. 11, 1990, abandoned.

[51] Int. Cl.$^5$ .................. A61K 31/535; C07D 498/04

[52] U.S. Cl. .................. 514/229.8; 514/296; 544/101; 546/89; 546/100

[58] Field of Search .................. 546/89, 100; 544/101; 514/229.8, 296

[56] References Cited

U.S. PATENT DOCUMENTS 5,059,597 10/1991 Petersen et al. .................. 544/101

Primary Examiner—Bernard Dentz
Attorney, Agent, or Firm—Peter C. Richardson; Paul H. Ginsburg; Genzina Holtrust

[57] ABSTRACT

Quinolone carboxylic acids 7-substituted by azabicyclo groups have antibacterial activity.

17 Claims, No Drawings

AZATRICYCLO CARBOXYLIC ACIDS USEFUL AS ANTI-BACTERIAL AGENTS

CROSS REFERENCE TO RELATED APPLICATION

This is a division of application Ser. No. 919,477, filed on Jul. 24, 1992 now U.S. Pat. No. 5,229,396, which is a division of application Ser. No. 650,835, filed on Feb. 4, 1991 now U.S. Pat. No. 5,164,402 which is a continuation in part of application Ser. No. 07/551,212 filed on Jul. 11, 1990, abandoned which is a continuation in part of application Ser. No. PCT/US 89/03489 filed on Aug. 16, 1989.

BACKGROUND OF THE INVENTION

The invention relates to novel 7-azabicyclo-substituted quinolone carboxylic acids, pharmaceutical compositions containing such compounds and methods of treatment with such compounds.

U.S. Pat. No. 4,571,396 discloses diazabicyclo-substituted naphthyridine-, quinoline- and benzoxazine-carboxylic acids having antibacterial activity. European Patent Publication No. 215650 discloses similar antibacterial diazabicyclo-substituted compounds.

SUMMARY OF THE INVENTION

The invention provides antibacterial compounds having the formula

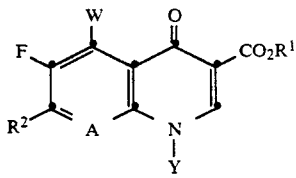

or a pharmaceutically acceptable acid addition salt thereof, wherein $R^1$ is hydrogen, a pharmaceutically acceptable cation, or ($C_1$-$C_6$) alkyl;

Y, when taken independently, is ethyl, t-butyl, vinyl, cyclopropyl, 2-fluoroethyl, p-fluorophenyl, or o,p-difluorophenyl;

W is hydrogen, F, Cl, Br, $C_1$-$C_4$ alkyl, $C_1$-$C_4$ alkoxy, $NH_2$, $NHCH_3$;

A is CH, CF, CCl, $COCH_3$, C—$CH_3$, C—CN or N; or

A is carbon and is taken together with Y and the carbon and nitrogen to which A and Y are attached to form a five or six membered ring which may contain oxygen or a double bond, and which may have attached thereto $R^8$ which is methyl or methylene; and $R^2$ is

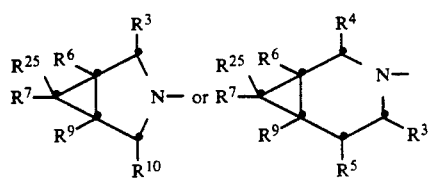

wherein $R^3$, $R^4$, $R^5$, $R^6$, $R^7$, $R^9$, and are each independently H, $CH_3$, $CH_2CH_2$, $CH_2NHCH_3$ or $CH_2NHC_2H_5$, and $R^5$, $R^6$, $R^7$, and $R^9$ may also independently be $NH_2$, $NHCH_3$ or $NHC_2H_5$, provided that not more than three of $R^3$, $R^4$, $R^5$, $R^6$, $R$, $R^9$, and are other than hydrogen, and if three of these substituents are not hydrogen, at least one of them is methyl; and prodrugs of those compounds of formula I having a free amino group.

Preferred compounds of the invention are those of formula I wherein $R^1$ is hydrogen or a pharmaceutically acceptable cation such as sodium or potassium, and hydrates thereof. Other preferred compounds are the p-toluenesulfonate, methanesulfonate and hydrochloride salts of the compounds of formula I.

Other preferred compounds are those wherein A is CH or N, or A is carbon and is taken together with Y and the carbon and nitrogen to which A and Y are attached to form a six membered ring as follows:

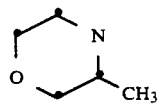

More preferably, A is CH or N, and most preferably, A is N. More specific compounds are those wherein one or two or $R^3$, $R^4$, $R^5$, $R^6$, $R^7$, $R^9$, $R^{10}$ and $R^{25}$ are other than hydrogen. Further more specific compounds are those wherein one of $R^3$, $R^4$, $R^5$, $R^6$, $R^7$, or $R^{10}$ is $CH_2NH_2$ or $CH_2NHCH_3$, and, optionally, another of $R^3$, $R^4$, $R^5$, $R^7$, $R^9$, $R^{10}$ or $R^{25}$ is methyl; or those wherein one of $R^5$, $R^6$, $R^7$ or $R^9$ is NH or $NHCH_3$ and, optionally, another of $R^5$, $R^6$, $R^7$ or $R^9$ or one of $R^3$, $R^4$, $R^{10}$ or $R^{25}$ is methyl rather than hydrogen. Preferred are those wherein $R^6$, $R^7$ or $R^9$ is amino and, optionally one of $R^3$, $R^4$, $R^5$, $R^6$, $R^7$, $R^9$, $R^{10}$, or $R^{25}$ is methyl, and more preferred $R^7$ is amino and, optionally, one of $R^3$, $R^4$, $R^5$, $R^6$, $R^9$, $R^{10}$, or $R^{25}$ is methyl. In the most preferred compounds $R^7$ is amino and $R^3$, $R^4$, $R^5$, $R^6$, $R^9$, $R^{10}$ and are each hydrogen.

Other preferred compounds are those of formula I wherein Y is cyclopropyl or o,p-difluorophenyl, and those wherein W is hydrogen.

Specific compounds of the invention are 7-(1-amino-3-azabicyclo[3.1.0]hex-3-yl)-6-fluoro-1-(2,4-di-fluorophenyl)-1,4-dihydro-4-oxo-1,8-naphthyridine-3-carboxylic acid, 7-([α,2β,5α,6α]-6-amino-2-methyl-3-azabicyclo[3.1.0]-hex-3-yl)-6-fluoro-1-(2,4-difluorophenyl))-1,4-dihydro-4-ox-o1,8-naphthyridine-3-carboxylic acid, 7-([1α,6α,7α[-7-amino-3-azabicyclo[4.1.0]hept-3-yl)-6-fluoro-1-(2,4-difluorophenyl)-1,4-dihydro-4-oxo-1,8-naphthyridine-3-carboxylic acid, 7-([1α,6α,7α[-7-amino-3-azabicyclo[4.1.0]hept-3-yl)-1-cyclopropyl-6-fluoro-1,4-dihydro-4-oxo-1,8-naphthyridine-3-carboxylic acid, 7-([1α,5α,6α]-6-amino-3-azabicyclo[3.1.0]hex-3-yl)-1-cyclopropyl-6-fluoro-1,4-dihydro-4-oxo-1,8-naphthyridine-3-carboxylic acid, 7-(1-amino-3-azabicyclo[4.1.0]hept-3-yl)-1-cyclopropyl-6-fluoro-1,4-dihydro-4-oxo-quinoline-3-carboxylic acid, 7-([1α,5α,6α]-6-[(N-methyl)amino]-3-azabicyclo[3.1.0]-hex-3-yl)-6-fluoro-1-(2,4-difluorophenyl)-1,4-dihydro-4-oxo-1,8-naphthyridine-3-carboxylic acid, 7-[(1α, 5α,6α)-6-amino-3-azabicyclo[3.1.0]hex-3-yl]-6-fluoro-1-(2,4-difluorophenyl)-1,4-dihydro-4-oxo-1,8-naphthyridine-3-carboxylic acid, hydrate, 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, hydrochloride salt, 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt, 7-([1α,5α,6α]-6-amino-3-azabicyclo[3.1.0]hex-3-fluoro-1-(2,4-difluorophenyl)-1,4-dihydro-4-oxo-1,8-naphthyridine-3-carboxylic acid, p-toluenesulfonic acid salt, 7-([1α,5α,6α]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, 7-([1α, 5α, 6β]-6-amino-3-azabicyclo[3.1.0]hex-3-yl)-6-fluoro-1-(2,4-difluorophenyl)-1,4-dihydro-4-oxo-1,8-naphthyridine-3-carboxylic acid, or 7([1α, 5α, 6α]-6-aminomethyl-3-azabicyclo[3.1.0]hex-3-yl) -fluoro-1-2(2,4-difluorophenyl)-1,4-dihydro-4-oxo-1,8-naphthyridine-3-carboxyclic acid.

The compounds of formula I of the invention wherein $R^3$, $R^4$, $R^5$, $R^7$, and $R^{25}$ are other than hydrogen can bear these substituents in either of two steric configurations relative to the cyclopropyl group in $R^2$. The compounds of formula I of the invention include the racemic mixtures and the optical isomers of all of these configurations.

The invention includes prodrugs of compounds of the formula I having free amino groups. Prodrugs are understood to be an amino acid residue, or a polypeptide chain of two or more, such as up to four, amino acid residues which are covalently joined through peptide bonds. The amino acid residues of use include the 20 naturally occurring amino acids designated by three letter symbols, 4-hydroxyproline, hydroxylysine, demosine, isodemosine, 3-methylhistidine, norvalin, beta-alamine, gamma-aminobutyric acid, citrulline homocysteine, homoserine, ornithine and methionine sulfone. Preferred amino acid residues are those with a nonpolar group such as Ala, Val, Nval, Leu, Met, Gly, Pro, Phe, or a basic polar group such as Lys.

The invention includes a pharmaceutical composition comprising a pharmaceutically acceptable carrier or diluent and a compound of the formula I in an antibacterially effective amount.

The invention further includes a method of treating a host, such as an animal or a human being, having a bacterial infection comprising administering to the host an antibacterially effective amount of a compound of the formula I, or a pharmaceutical composition as defined above.

The invention also includes intermediates of use in the preparation of a compound of the formula I. Exemplary intermediates have the formulae

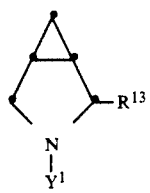

wherein $Y^1$ is hydrogen or benzyl, and $R^{13}$ is methyl, cyano, hydroxymethyl, carboxyl or $CH_2NR^{11}R^{12}$, wherein $R^{11}$ is hydrogen, methyl, or ethyl, and $R^{12}$ is hydrogen, $C_1$–$C_6$ acyl, $C_2$–$C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl.

with the proviso that when $Y^1$ is hydrogen, then $R^{13}$ is methyl or $CH_2NR^{11}R^{12}$ as defined above; and

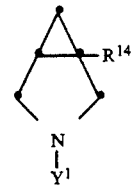

wherein $Y^1$ is hydrogen or benzyl, and $R^{14}$ is hydroxymethyl, $CH_2NR^{11}R^{12}$ or $NR^{11}R^{12}$, wherein $R^{11}$ is hydrogen, methyl, or ethyl, and $R^{12}$ is hydrogen, $C_1$–$C_6$ acyl, $C_2$–$C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

wherein $Y^2$ is hydrogen, benzyl, or benzyloxycarbonyl, and $R^{15}$ is carboxyl, hydroxymethyl, CHO, $CH_2NR^{11}R^{12}$ or $NR^{11}R^{12}$ wherein $R^{11}$ is hydrogen, methyl, or ethyl, and $R^{12}$ is hydrogen, $C_1$–$C_6$ acyl, $C_2$–$C_6$ alkoxycarbonyl, optionally substituted bynzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

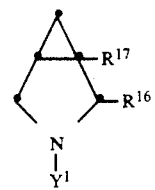

wherein $Y^1$ is hydrogen or benzyl, $R^{16}$ is methyl, hydroxymethyl, CHO, hydroxymethyl tetrahydropyranyl ether, or $CH_2NR^{11}R^{12}$, and $R^{17}$ is methyl, cyano, carboxyl, hydroxymethyl, or $CH_2NR^{11}R^{12}$, wherein $R^{11}$ is hydrogen, methyl, or ethyl, and $R^{12}$ is hydrogen, $C_1$–$C_6$ acyl, $C_2$–$C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

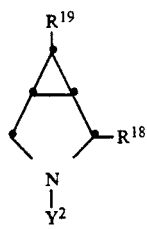

wherein $Y^2$ is hydrogen, benzyl, or benzyloxycarbonyl, $R^{18}$ is methyl, cyano, hydroxymethyl, or $CH_2NR^{11}R^{13}$, and $R^{19}$ is methyl, carboxyl, hydroxymethyl, CHO, hydroxymethyl tetrahydropyranyl ether, $CH_2NR^{11}R^{12}$, or $NR^{11}R^{12}$, wherein $R^{11}$ is hydrogen, methyl or ethyl and $R^{12}$ is hydrogen, $C_1-C_6$ acyl, $C_2-C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

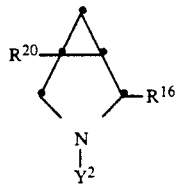

wherein $Y^2$ is hydrogen, benzyl, or benzyloxycarbonyl, $R^{16}$ is methyl, hydroxymethyl, CHO, hydroxymethyl tetrahydropyranyl ether, or $CH_2NR^{11}R^{12}$, and $R^{20}$ is methyl, carboxyl, hydroxymethyl, CHO, Methoxycarbonyl, ethoxycarbonyl, $CH_2NR^{11}R^{12}$, or $NR^{11}R^{12}$ wherein $R^{11}$ is hydrogen, methyl or ethyl, and $R^{12}$ is hydrogen, $C_1-C_6$ acyl, $C_2-C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

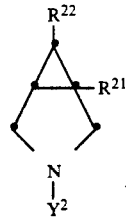

wherein $Y^2$ is hydrogen, benzyl, or benzyloxycarbonyl, $R^{21}$, is methyl, carboxyl, hydroxymethyl, CHO, hydroxymethyl tetrahydropyranyl ether, t-butoxycarbonyl, methoxycarbonyl, $CH_2NR^{11}R^{12}$ or $NR^{11}R^{12}$, and $R^{22}$ is methyl, carboxyl, hydroxymethyl, CHO, ethoxycarbonyl, $CH_2NR^{11}R^{12}$, or $NR^{11}R^{12}$ wherein $R^{11}$ is hydrogen, methyl or ethyl and $R^{12}$ is hydrogen, $C_1-C_6$ acyl, $C_2-C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

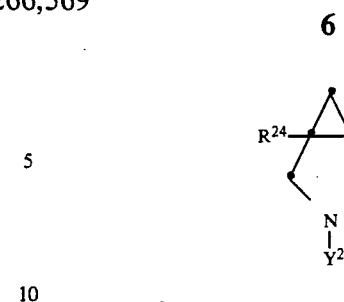

wherein $Y^2$ is hydrogen, benzyl, or benzyloxycarbonyl, $R^{23}$ is methyl, carboxyl, hydroxymethyl, CHO, methoxycarbonyl, $CH_2NR^{11}R^{12}$ or $NR^{11}R^{12}$, and $R^{24}$ is methyl, carboxyl, hydroxymethyl, CHO, hydroxymethyl tetrahydropyranyl ether, $CH_2NR^{11}R^{12}$, or $NR^{11}R^{12}$, wherein $R^{11}$ is hydrogen, methyl or ethyl and $R^{12}$ is hydrogen, $C_1-C_6$ acyl, $C_2-C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl; and

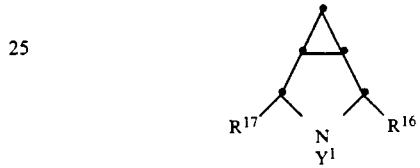

wherein $Y^1$ is hydrogen or benzyl, $R^{16}$ is methyl, hydroxymethyl, CHO, hydroxymethyl tetrahydropyranyl ether, or $CH_2NR^{11}R^{12}$, and $R^{17}$ is methyl, cyano, carboxyl, hydroxymethyl, CHO, or $CH_2NR^{11}R^{12}$, wherein $R^{11}$ is hydrogen, methyl or ethyl, and $R^{12}$ is hydrogen, $C_1-C_6$ acyl, $C_2-C_6$ alkoxycarbonyl, optionally substituted benzyloxycarbonyl, aryloxycarbonyl, silyl, trityl, tetrahydropyranyl, vinyloxycarbonyl, o-nitrophenylsulfonyl, diphenylphosphonyl, p-toluenesulfonyl, or benzyl.

Other intermediates of use in preparing compounds I are evident from the description below, particularly the sections numbered by Roman numerals.

DETAILED DESCRIPTION OF THE INVENTION

The term "$C_1-C_6$ alkyl", used in the definition of $R^1$, denotes saturated monovalent straight or branched aliphatic hydrocarbon radicals having one to six carbon atoms, such as methyl, ethyl, propyl, isopropyl, t-butyl, etc.

When A is carbon and is taken together with Y and the carbon and nitrogen to which A and Y, respectively, are attached to form a five membered ring or a six membered ring, the compounds of formula I in one specific embodiment have the following formula:

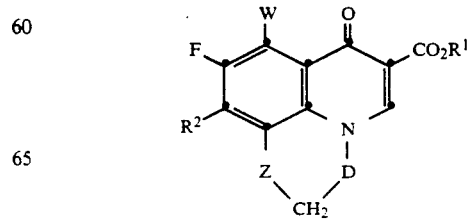

wherein Z is $CH_2$, O or a covalent bond, and D is $CH_2$, $CHCH_3$ or $C=CH_2$, and D may be $CH=CH$ when Z is a covalent bond.

The compounds (I) of the invention may be prepared by reacting a compound of the formula

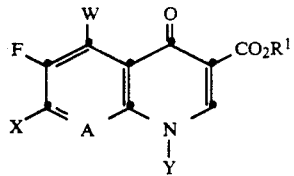

II with a compound of the formula $R^2H$ wherein $R^1$, $R^2$, A, W and Y are as defined above in connection with formula I, except that $R^2$ includes within the definitions of $R^3$, $R^4$, $R^5$, $R^6$, $R^7$, $R^9$, $R^{10}$ and $R^{11}$ the N-protected groups of $NH_2$, $CH_2NH_2$, $NHCH_3$, $CH_2NHCH_3$, $NHC_2H_5$, and $CH_2NHC_2H_5$, and X is a leaving group such as fluoro, chloro, bromo or $C_1-C_3$ alkylsulfonyl. Nitrogen protecting groups are known in the art. Examples of suitable nitrogen protecting groups are $C_1-C_6$ acyl, $C_2-C_6$ alkoxycarbonyl optionally substituted benzyloxycarbonyl, aryloxycarbonyl, silyl, trityl, tetrahydropyranyl, vinyloxycarbonyl, O-nitrophenylsulfonyl, diphenylphosphinyl, p-toluenesulfonyl, and benzyl. The nitrogen protecting group is removed by methods known in the art such as hydrogenation or hydrolysis.

The reaction may be conducted with or without a solvent. The solvent, when used, must be inert under the reaction conditions. Suitable solvents are acetonitrile, tetrahydrofuran, ethanol, chloroform, dimethylsulfoxide, dimethylformamide, pyridine, water, or mixtures thereof.

The reaction temperature usually ranges from about 20° C. to about 150° C.

The reaction may advantageously be carried out in the presence of an acid acceptor such as an inorganic or organic base, e.g. an alkali metal or alkaline earth metal carbonate or bicarbonate, or a tertiary amine, e.g. triethylamine, pyridine or picoline.

When $R^1$ is $C_1-C_6$ alkyl, conversion to the corresponding acid may be carried out under acidic or basic conditions conventional for hydrolysis of carboxylic acid esters, at about 20° to 150° C.

The starting materials of formula II are known in the art, e.g. as disclosed in U.S. Pat. Nos. 4,571,396 and 4,775,668. The starting materials of formula $R^2H$ have the following formulae

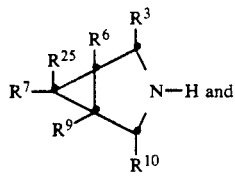

III

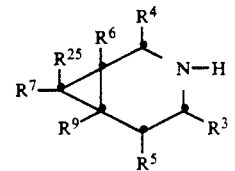

IV wherein $R^3$, $R^4$, $R^5$, $R^6$, $R^7$, $R^9$, $R^{10}$ and $R^{25}$ are as defined above in connection with a compound of the formula $R^2H$. Specific examples of such starting materials are the following compounds:

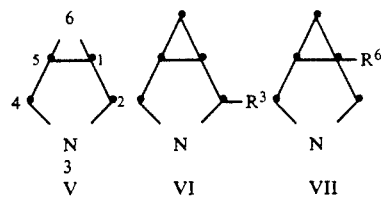

V  VI  VII

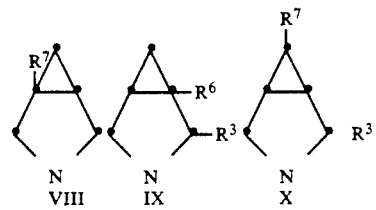

VIII  IX  X

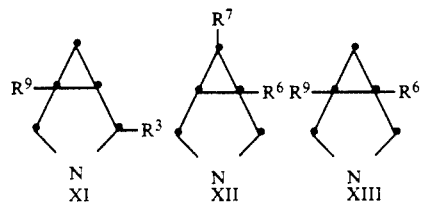

XI  XII  XIII

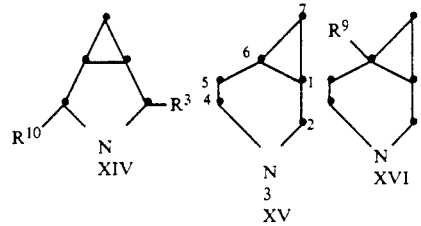

XIV  XV  XVI

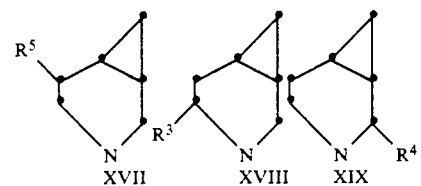

XVII  XVIII  XIX

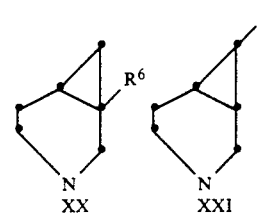

XX  XXI

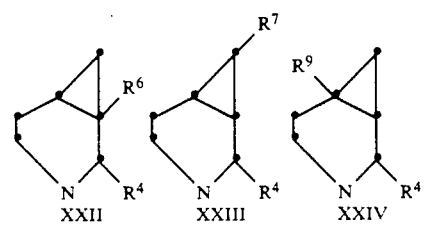

XXII  XXIII  XXIV

-continued
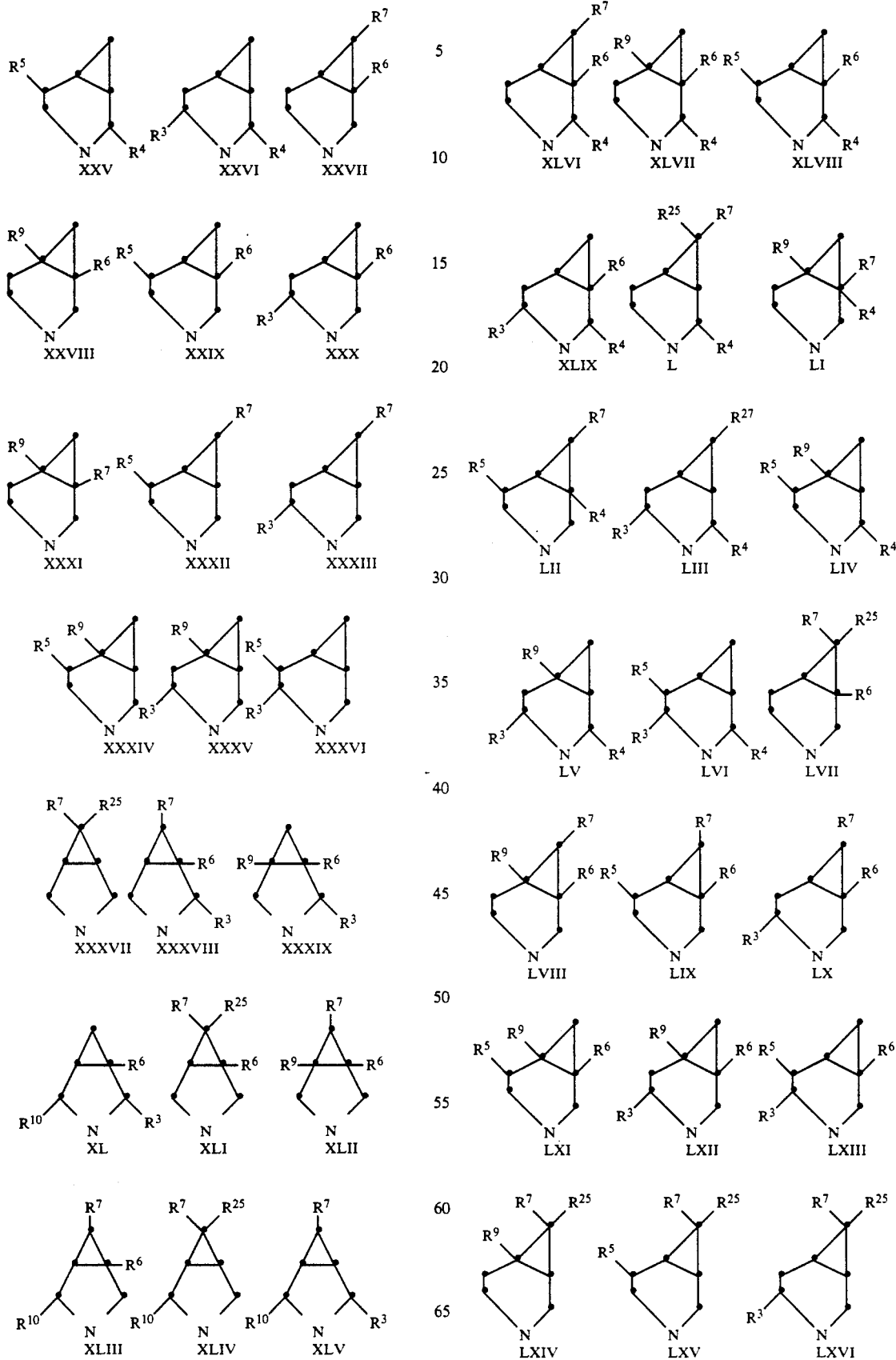

-continued

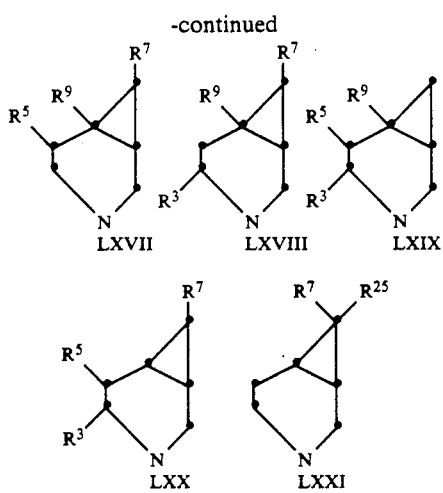

wherein $R^2$, $R^4$, $R^5$, $R^6$, $R^7$, $R^9$, $R^{10}$ and $R^{25}$ are as defined above, except hydrogen.

The preparation of representative foregoing compounds I to XXI is discussed below wherein each section is referred to by the formula of the compounds prepared.

3-Azabicyclo[3.1.0]hexane (V)

3-Azabicyclo[3.1.0]hexane may be prepared by the method of D. A. Wood et al. European Patent Publication 0010799 from 1,2-cyclopropanedicarboxylic acid.

2-$R^3$-Substituted 3-Azabicyclo[3.1.0]hexanes (VI)

2-Cyano-3-azabicyclo[3.1.0]hexane can be prepared by the method of D. A. Wood et al. EP 0010799. Protection of the ring nitrogen, for instance by a benzyl group, then provides 3-benzyl-2-cyano-3-azabicyclo[3.1.0]hexane. Reduction of the nitrile with lithium aluminum hydride gives a compound of the formula VI wherein $R^3$ is $CH_2NH_2$ and the 3-N is benzylated. This compound, and all subsequently described amino-substituted azabicyclo[3.1.0]hexyl systems, may be advantageously protected, for instance with an alkoxycarbonyl group such as tert-butoxy-carbonyl, or a carboxylic acid group such as formyl or acetyl, and subsequently debenzylated via hydrogenation to provide the protected 2-aminomethyl-3-azabicyclo[3.1.0]hexane. After coupling of this debenzylated diamine to a quinolone or naphthyridine nucleus by reaction with a compound of the formula II, the amino-protecting group such as the tert-butoxy-carbonyl or acetyl group can be removed by exposure to acidic conditions.

Alternatively, the diamine 2-aminomethyl-3-benzyl-3-azabicyclo[3.1.0]hexane can be formylated or acetylated by heating to reflux with ethyl formate, according to the procedure of Moffat et al., J. Org. Chem., 27, 4058 (1962), or acetyl chloride. These amides can then be reduced to the corresponding amines with lithium aluminum hydride, to provide a compound of the formula VI wherein $R^3$ is $CH_2NHCH_3$ or $CH_2NHC_2H_5$. This compound may be protected, as in the case of the conversion of the above diamine 2-aminomethyl-3-benzyl-3-azabicyclo[3.1.0]hexane to 2-[(N-acetyl)aminomethyl] or 2-[(N-tert-butoxycarbonyl)aminomethyl]-3-benzyl-3-azabicyclo[3.1.0]hexane, then debenzylated and appended to the quinolone or naphthyridine nucleus by reaction with a compound of the formula II.

For the case wherein $R^3$ is $CH_3$, the above nitrile 3-benzyl-2-cyano-3-azabicyclo[3.1.0]hexane can be hydrolyzed under acidic or basic conditions to the corresponding carboxylic acid, and reduced with lithium aluminum hydride to the alcohol 3-benzyl-2-hydroxymethyl-3-azabicyclo[3.1.0]hexane. Formation of the tosylate followed again by lithium aluminum hydride reduction provides the 2-methyl congener 3-benzyl-2-methyl-3-azabicyclo[3.1.0]hexane, which can be debenzylated as above.

1-$R^6$-Substituted-3-azabicyclo[3.1.0]hexanes (VII)

These compounds can be prepared from the nitrile 3-benzyl-1-cyano-3-azabicyclo[3.1.0]hexane, whose preparation is reported by Achini and Oppolzer, Tetrahedron Letters, 1975, 369. Alternatively, the nitrile may be synthesized from 3-[(benzyl)(2,3-dihydroxypropyl)amino]-propanenitrile via bismesylation, followed by double ring closure with sodium hexamethyldisilazide. Transformation of the nitrile functionality of 3-benzyl-1-cyano-3-azabicyclo[3.1.0]hexane into $CH_3$, $CH_2CH_2$, $CH_2NHCH_3$ or $CH_2NHC_2H_5$ can be carried out as in section VI above.

Hydrolysis of 3-benzyl-1-cyano-3-azabicyclo[3.1.0]hexane to 3-benzyl-3-azabicyclo[3.1.0]hexane-1-carboxylic acid can be carried out under basic conditions. Subsequent reaction with diphenylphosphoryl azide in t-butanol, using the procedure reported by Ninomiya et al., Tetrahedron 1974, 30, 2151, provides the protected amine 3-benzyl-1-tert-butoxycarbonylaino-3-azabicyclo-3.1.0]hexane. Debenzylation as above yields an amine which can be coupled to the quinolone or naphthyridine nucleus by reaction with a compound of the formula II; acidic removal of the tert-butoxycarbonyl group provides the final product with an amino group as the 1-substituent in the 3-azabicyclo[3.1.0]hexane side chain.

Removal of the tert-butoxycarbonyl group from the protected amine to give 1-amino-3-benzyl-3-azabicyclo[3.1.0]hexane can be followed by acetylation or formylation and lithium aluminum hydride reduction as above to provide a compound of the formula VII wherein $R^6$ is $NHCH_3$ or $NHC_2H_5$. This can be further processed as in Section VI to provide the final product bearing a methylamine or ethylamine at C-1 of the 3-azabicyclo[3.1.0]hexane side chain.

Alternatively, 3-benzyl-1-tert-butoxycarbonylamino-3-azabicyclo[3.1.0]hexane can be N-alkylated by treatment with sodium hydride and methyl or ethyl iodide. The resulting diprotected N-alkyl compound can be debenzylated and processed as in Section VI.

6-$R^7$-Substituted-3-azabicyclo[3.1.0]hexanes (VIII)

Addition of ethyl diazoacetate to N-benzylmaleimide generates a pyrazoline which upon thermolysis provides 3-benzyl-3-azabicyclo[3.1.0]hexane-2,4-dione-6-carboxylic acid ethyl ester. Reduction with lithium aluminum hydride gives 3-benzyl-6-hydroxymethyl-3-azabicyclo[3.1.0]hexane; Swern oxidation followed by oxime formation and lithium aluminum hydride reduction then produces the primary amine, which can be protected or treated as above to give a compound of formula VIII wherein $R^7$ is $CH_2NHCH_3$ or $CH_2NHCH_2CH_3$.

Alternatively, 3-benzyl-6-hydroxymethyl-3-azabicyclo-[3.1.0]hexane can be treated as in Section VI to provide the 6-methyl derivative. To prepare compounds with a 6-amino group, hydrogenolytic removal of the benzyl group from 3-benzyl-6-hydroxymethyl-3- azabicyclo[3.1.0]hexane is followed by introduction of a benzyloxycarbonyl group; Jones oxidation at this point provides 3-benzyloxycarbonyl-3-azabicyclo[3.1.0]hexane-6-carboxylic acid. Curtius rearrangement as in Section VII, using diphenyloxycarbonyl-6-tert-butoxyphosphoryl azide, yields 3-benzylcarbonylamino-3-azabicyclo[3.1.0]hexane, which can be taken on to the analogue bearing a primary amine, or which can be deprotected and further manipulated as in Section VII to provide the compounds of formula VIII wherein $R^7$ is $NHCH_3$ or $NHC_2H_5$.

Another route to these compounds involves treatment of N-benzyloxycarbonyl-3-pyrroline with ethyl diazoacetate under rhodium acetate catalysis, to provide the ethyl ester of 3-benzyloxycarbonyl-3-azabicyclo[3.1.0]hexane-6-carboxylic acid. Basic hydrolysis, for instance with sodium hydroxide in methanol, then gives the corresponding carboxylic acid, which can be processed as described above. Alternatively, the benzyloxycarbonyl group can be removed by hydrogenolysis, and the nitrogen functionality protected as a benzyl derivative, by treatment with benzyl bromide. Subsequent lithium aluminum hydride reduction then gives 3-benzyl-6-hydroxymethyl-3-azabicyclo[3.1.0]hexane, which can be further functionalized as described above.

1,2-$R^6$,$R^3$-Disubstituted-3-azabicyclo[3.1.0]hexanes (IX)

Modification of the Oppolzer procedure mentioned in Section VII provides this substitution pattern. For the 2-methyl substituted compounds, 3-benzylaminobutanenitrile is used as the starting material. For all other 2-substituents, 3-(benzylamino)-4-[(tetrahydro-2H-pyran-2-yl)oxy]-butanenitrile, available from beta-cyanoalanine via carboxylic acid reduction, alcohol protection and N-benzylation, can be reacted with glycidol to provide 3-[(benzyl)(2,3-dihydroxypropyl)amino]-4-[(tetrahydro-2H-pyran-2-yl)oxy]-butanenitrile. Tosylation of the primary alcohol is followed by base-induced ring closure to 3-[(benzyl)(2,3-epoxypropyl)amino]-4-[(tetrahydro-2H -pyran-2yl)oxy]-butanenitrile; sodium hexamethyldisilazide treatment provides 1-benzyl-4-hydroxymethyl-2-[(tetrahydro-2H-pyran-2-yl)oxy]methyl-3-pyrrolidine-carbonitrile. A second tosylation can be followed again by base-induced ring closure to the 3-azabicyclo[3.1.0]hexane of the formula IX wherein the 2-substituent is tetrahydropyeranyloxymethyl, the 1-substituent is cyano, and the 3-aza nitrogen is benzylated. The nitrile functionality of the latter can be transformed into all of the substituents $R^6$ as in Section VII.

For the elaboration of the C-2 substituent $R^3$, final C-1 substituents $R^6$ bearing amino groups can be protected as the corresponding acetamides. Subsequent acid-induced removal of the tetrahydropyran (THP) protecting group gives a primary alcohol which can be subjected to a Swern oxidation; reductive amination of the derived aldehyde with amonium acetate, methylamine or ethylamine then provides the corresponding amines of the formula IX wherein $R^6$ is $CH_3$ or aminoprotected $CH_2Ch_2$, $CH_2NHCH_3$, $NH_2$, $NHCH_3$, or $NHC_2H_5$, and $R^3$ is $CH_2CH_2$, $CH_2NHCH_3$,or $CH_2NHC_2H_5$. Protection of the resultant 2-amine can be carried out as above, with the tert-butoxycarbonyl protecting group; removal of the benzyl group via hydrogenation provides the free secondary amine, which can be coupled to the quinolone or naphthyridine nucleus, followed by acid-induced removal of the acetamide and tert-butoxycarbonyl groups.

2,6-$R^3$,$R^7$-Disubstituted-3-azabicyclo[3.1.0]hexanes (X)

These compounds can be prepared from 3-benzyl-6-hydroxymethyl-3-azabicyclo[3.1.0]hexane; protection as the THP ether, followed by debenzylation, provides 6-[(tetrahydro-2H-pyran-2-yl)oxy]methyl-3-azabicyclo-[3.1.0]hexane. A cyano group can then be introduced into the 2-position by the method of Wood, as in Section VI. Reintroduction of the benzyl group provides 3-benzyl-2-cyano-6-[(tetrahydro-2H-pyran-2-yl)oxy]methyl-3-azabicyclo[3.1.0]hexane, wherein the two substituents are differentially functionalized. The cyano group can be transformed into the desired 2-substituents, as described in Section VI. At this point, protection of any primary or secondary amine as its acetamide can be followed by acidic removal of the tetrahydropyran protecting group, and elaboration of the primary alcohol into the desired substituent by the methods outlined in Section VIII.

When the 6-substituent is a methyl group, elaboration of the tetrahydropyranyl ether is carried out prior to introduction of the cyano group at C-2. When the 2-substitutent is a methyl group, an alternate route involves rhodium acetate-catalyzed cyclopropanation of N-benzyloxycarbonyl-2-methyl-3-pyrroline (available via the chemistry described by Takano, *Heterocycles*, 1989, 29, 1861, starting with 4-hydroxy-1-pentene) with ethyl diazoacetate. The ester group can then be elaborated to the desired 6-substituent as in Section VIII.

1,4-$R^3$ Disubstituted-3-azabicyclo[3.1.0]hexanes (XI)

These compounds can be prepared from methyl acrylate and 2-benzylamino-3-[(tetrahydro-2H-pyran-2-yl)oxy]-propanoic acid methyl ester; heating these reagents in methanol provides an adduct which can be cyclized with sodium hexamethyldisilazide to 1-benzyl-4-oxo-5-[(tetrahydro-2H-pyran-2-yl)oxy]methyl-3-pyrrolidine carboxylic acid methyl ester. Reduction and benzyl group removal is effected with Raney nickel; introduction of a benzyloxycarbonyl group is then followed by mesylation of the secondary alcohol and diazabicyclononane-mediated dehydration to give 1-benzyloxycarbonyl-2,5-dihydro-5-[(tetrahydro-2H-pyran-2-yl)oxy]methyl-1H-pyrrole-3-carboxylic acid, methyl ester. Cyclopropanation with diiodomethane and zinc/silver couple, according to the method of Denis et al., *Synthesis*, 1972, 549, gives the bicyclo[3.1.0-]hexyl system of formula XI wherein the 1-substituent is CO the 4-substituent is tetrahydropyranyloxymethyl, and the 3-nitrogen is protected with benzyloxycarbonyl. The ester can be reduced to the corresponding alcohol wherein the 1-substituent is hydroxy-methyl with lithium borohydride. Removal of the benzyloxycarbonyl group by hydrogenolysis using 10% palladium on carbon can then be followed by benzylation with benzyl bromide, to provide the compound of formula XI wherein the 1-substituent is hydroxymethyl, the 4-substituent is tetrahydropyranyloxymethyl, and the 3-nitrogen is protected with benzyl. Alternatively, the cyclopropanation product obtained above can be hydrolyzed with sodium hydroxide to the corresponding acid wherein the 1-substituent is $CO_2H$. These two compounds can be manipulated as in Section VIII to provide the desired 1-substituent $R^9$; after protection of the 1-substituent, the 4-substituent $R^3$ can be generated from the tetrahydropyranyl-protected alcohol as in Section IX. Removal of the 3-benzyloxycarbonyl group can then be effected by hydrogenation.

When the desired 4-substituent is a methyl group, the chemistry described above can be carried out starting with 2-benzylamino-propanoic acid methyl ester.

1,6-$R^6$,$R^7$-Disubstituted-3-azabicyclo[3.1.0]hexanes (XII)

These compounds can be prepared from tert-butyl acrylate and N-benzylglycine methyl ester; 1-benzyloxy-carbonyl-2,5-dihydro-1H-pyrrole-3-carboxylic acid, tert-butyl ester is then synthesized via the methods described in Section XI. Molybdenum hexacarbonyl-mediated cyclopropanation with ethyl diazoacetate then provides the bicyclic system of the formula XII wherein the 1-substituent is t-butyloxycarbonyl, the 6-substituent is ethyloxycarbonyl, and the 3-nitrogen is substituted by benzyloxycarbonyl. Selective hydrolysis of the tert-butyl ester with trifluoroacetic acid can be followed by diborane-mediated reduction of the liberated carboxylic acid and protection of the derived primary alcohol as its tetrahydropyranyl ether. The 6-carboethoxy group can then be transformed into the desired 6-substituent as described above with respect to compounds of the formula XI. For a -methyl substituent, the protecting group on nitrogen is changed from benzyloxycarbonyl to benzyl as outlined in Section IX. After protection of any primary or secondary amines, the tetrahydropyranyl group can be removed under acidic conditions and the primary alcohol can be elaborated into the desired 1-substituent by the methods outlined in Section VIII.

For the case of a 1-methyl substituent, N-benzyloxycarbonyl-3-methyl-3-pyrroline (available via N-protection of 3-methyl-3-pyrroline, whose preparation is described by Gajda, Liebigs Ann. Chem, 1986, 992) is cyclopropanated using ethyl diazoacetate under rhodium acetate catalysis, to give a compound of formula XII wherein the 1-substituent is methyl, the 3-substituent is benzyloxycarbonyl, and the -substituent is ethoxycarbonyl. The ester functionality
is then elaborated as described above.

1,5-$R^6$,$R^9$-Disubstituted-3-azabicyclo[3.1.0]hexanes (XIII)

These compounds are derived from 1-benzyl-4-hydroxymethyl-3-pyrrolidine carbonitrile, whose preparation is described by Achini and Oppolzer as mentioned in Section VII. Protection of the primary alcohol followed by nitrile hydrolysis and diazomethane esterification provides 1-benzyl-4-[(tetrahydro-2H-pyran-2-yl)oxy]methyl-3-pyrrolidine carboxylic acid methyl ester. The benzyl group can be removed by hydrogenation and replaced by a benzyloxycarbonyl group. Introduction of a thiophenyl group can then be effected via deprotonation with sodium hydride and reaction of the derived enolate with S-phenyl benzenethiosulfonate to give 1-benzyloxycarbonyl-4-[(tetrahydro-2H-pyran -2-yl)oxy]-3-thiophenyl-3-pyrrolidinecarboxylic acid methyl ester. Oxidation of the sulfur with hydrogen peroxide, followed by thermolysis of the derived sulfoxide then gives alkene 1-benzyloxycarbonyl-2,5-dihydro-4-[(tetra-hydro-2H-pyran-2-yl)oxy]methyl-1H-pyrrol-3-carboxylic acid methyl ester. Cyclopropanation with diiodomethane provides the bicyclic system of formula XIII wherein the 1-substituent is methoxycarbonyl, the 5-substituent is tetrahydropyranyloxymethyl, and the 3-aza is substituted by benzyloxycarbonyl, which can be further elaborated as in Section XII to give all of the disubstituted compounds.

When the 1-substituent is methyl, the benzyloxycarbonyl group is replaced with a benzyl group, as in Section XI, prior to conversion of the tetrahydropyranyloxymethyl group to a methyl group.

2,4-$R^3$,$R^{10}$-azabicyclo[3.1.0]hexanes (XIV)

These compounds can be prepared from 3-benzyl-2-hydroxymethyl-3-azabicyclo[3.1.0]hexane by protection of the primary alcohol as the tetrahydropyranyl ether, debenzylation, introduction of a cyano group at the 4-position, and conversion into the desired 2- and 4-substituents according to the methods described in Section X.

3-Azabicyclo[4.1.0]heptane (XV)

Reaction of 1-benzyl-1,2,5,6-tetrahydropyridine with diazomethane and zinc iodide, according to the method of Attia, Ind. J. Chem., 16B, 98 (1978) provides 3-benzyl-3-azabicyclo[4.1.0]heptane. Hydrogenolytic removal of the benzyl group gives 3-azabicyclo[4.1.0]heptane.

6-$R^9$-Substituted 3-Azabicyclo[4.1.0]heptanes (XVI)

Reaction of 3-benzylamino-1,2-dihydroxypropane with 4-bromobutanenitrile provides 4-[(benzyl) (2,3-dihydroxypropyl)aminop]butanenitrile. Processing of this compound as in Section VII provides 3-benzyl-6-cyano-3-azabicyclo-[4.1.0]heptane. The nitrile group of this compound can be transformed into the desired 6-$R^9$-substituents as described in Section VII.

Alternatively, methyl 1-benzyloxycarbonyl-1,2,5,6-tetrahydropyridine-4-carboxylate can be reduced with diisobutylaluminum hydride, to provide 1-benzyloxycarbonyl-4-hydroxymethyl-1,2,5,6-tetrahydropyridine. Cyclopropanation using samarium amalgam and iodochloromethane, then gives 3-benzyloxycarbonyl-6-hydroxymethyl-3-azabicyclo[4.1.0]heptane. The hydroxymethyl group can be transformed into the desired substituent by the methods outlined in Section VIII.

5-$R^5$-Substituted-3-Azabicyclo[4.1.0]heptanes (XVII)

These compounds can be prepared from 3-azabicyclo-[4.1.0]heptan-4-one, disclosed in U.S. Pat. No. 4,262,124. Reaction with sodium hydride and benzyl bromide provides 3-benzyl-3-azabicyclo[4.1.0]heptan-4-one, which can be subjected to treatment with strong base, such as lithium hexamethyldisilazide, and then reacted with formaldehyde. Subsequent protection of the resulting primary alcohol as the tetrahydropyranyl ether gives 3-benzyl-5-[(tetrahydro-2H-pyran-2-yl)oxy]methyl-3-azabicyclo[4.1.0]heptan-4-one. Lithium aluminum hydride reduction then yields the bicyclic system of the formula XVII where the 5-substituent is tetrahydropyranyl-protected hydroxymethyl. This substituent, after acid-induced removal of the THP group, can be transformed into the desired 5-$R^5$-substituent by utilizing the methods described in Section VIII.

Alternatively, when $R^5$ is amino or substituted amino, the compounds may be prepared starting from 1-benzyloxycarbonyl-5-hydroxy-1,2,5,6-tetrahydropyridine. Samarium-promoted cyclopropanation, as in Section XVI, can then be followed by replacement of the benzyloxycarbonyl group by a benzyl group, as in Section VIII (the benzyl bromide step can be replaced by treatment with benzaldehyde/sodium cyanoborohydride), to give 3-benzyl-5-hydroxy-3-azabicyclo-[4.1.0]heptane. A Swern oxidation provides the corresponding ketone, and subsequent treatment with hydroxylamine hydrochloride, followed by lithium aluminum hydride reduction of the derived oxime, then gives 3-benzyl-5-amino-3-azabicyclo[4.1.0]heptane. Protection of the primary amine as its tert-butoxycarbonyl derivative can then be followed, if desired, by introduction of an N-methyl or N-ethyl group, as in Section VII.

4-$R^3$-Substituted-3-Azabicyclo[4.1.0]heptanes (XVIII)

These compounds can be prepared from 2-hydroxymethylpyridine by protection of the primary alcohol as the tetrahydropyranyl ether followed by reaction with benzyl iodide, and sodium borohydride reduction, according to the method reported by Sashida and Tsuchiya, *Chem. Pharm. Bull.*, 32, 4600 (1984), to provide 1-benzyl-2-[(tetrahydro-2H-pyran-2-yl)oxy]methyl-1,2,3,6-tetrahydropyridine. Cyclopropanation with diazomethane/zinc iodide, according to the method of Attia in Section XV, then gives 3-benzyl-4-[(tetrahydro-2H-pyran-2-yl)oxy]methyl-3-azabicyclo-4.1.0]heptane. Acid-induced removal of the tetrahydropyranyl group can be followed by methods described in Section VIII to provide the desired 4-$R^3$-substituent 2-$R^4$-Substituted-3-Azabicyclo[4.1.0]heptanes (XIX)

Compounds of this type may be prepared from bicyclo-3.1.0]hexan-3-one by deprotonation with strong base, such as lithium hexamethyldisilazide, followed by quenching of the derived enolate with formaldehyde and protection of the resulting primary alcohol as the tetrahydropyranyl ether to provide 2-[(tetrahydro-2H-pyran-2-yl)oxy]methyl-bicyclo-[3.1.0]hexan-3-one. Beckmann rearrangement of this compound, via the corresponding oxime tosylate, provides 2-[(tetrahydro-2H-pyran-2-yl)oxy]methyl-3-azabicyclo-[4.1.0]heptan-4-one. Reaction with sodium hydride and benzyl bromide, followed by reduction with lithium aluminum hydride, then gives 3-benzyl-2-[(tetrahydro-2H-pyran-2-yl)-oxy]methyl-3-azabicyclo[4.1.0]heptane; the protected hydroxymethyl 2-substituent can be transformed into the desired 2-substituent utilizing the methods described in Section IX.

1-$R^6$-Substituted-3-Azabicyclo[4.1.0]heptanes (XX)

These compounds can be prepared from methyl 1-benzyloxycarbonyl-1,2,5,6-tetrahydropyridine-3-carboxylate, using the methodology described in Section XVI to generate 3-benzyloxycarbonyl-1-hydroxymethyl-3-azabicyclo-[4.1.0]heptane. The methodology described in Section VIII can be used to convert the hydroxymethyl group into the desired substituent. In this case, as well as others where the Curtius rearrangement is employed, good results may be obtained using the modified Curtius reaction described by Overman, *Org. Synth. Coll. Volume VI*, 95.

7-$R^7$-Substituted-3-Azabicyclo[4.1.0]heptanes (XXI)

These compounds can be prepared from 1-benzyl-5,6-dihydro-2(1H)-pyridine by reaction with ethyl diazoacetate with molybdenum hexacarbonyl catalyst to provide 3-benzyl-2-oxo-3-azabicyclo[4.1.0]heptane-7-carboxylic acid ethyl ester, which can be reduced with lithium aluminum hydride to provide 3-benzyl-7-hydroxymethyl-3-azabicyclo[4.1.0]heptane. Utilization of the methods in Section VIII then yields the desired 7-$R^7$-substituent.

Alternatively, 1-benzyloxycarbonyl-1,2,5,6-tetrahydropyridine can be subjected to reaction with ethyl diazoacetate under rhodium acetate catalysis, to provide ethyl-3-benzyloxycarbonyl-3-azabicyclo[4.1.0-]heptane-7-carboxylate. Ester hydrolysis with sodium hydroxide then provides the corresponding carboxylic acid, which can be converted as described in Section VIII to give amino or substituted amino derivatives.

2,7-$R^4$,$R^7$-Disubstituted-3-azabicyclo[4.1.0]heptanes (XXIII)

These compounds are derived from 1-methyl-2-tetrahydropyranyloxymethyl-1,2,5,6-tetrahydropyridine, which can be prepared from 2-(hydroxymethyl)pyridine using the procedures outlined in Section XVIII. Treatment of 1-methyl-2-tetrahydropyranyloxymethyl-1,2,5,6-tetrahydropyridine with -chloroethyl chloroformate, followed by methanol, serves to remove the 1-methyl group; treatment of the secondary amine with benzyl chloroformate then yields 1-benzyloxycarbonyl-2-tetrahydropyranyloxymethyl-1,2,5,6-tetrahydropyridine. Cyclopropanation of this compound with ethyl diazoacetate in the presence of catalytic rhodium acetate gives ethyl 3-benzyloxycarbonyl-2-tetrahydropyranyloxymethyl-3-azabicyclo[4.1.0]heptane-7-carboxylate. This can be transformed into a compound with the desired substitution pattern, using the chemistry described in Section XI.

2,6-$R^4$,$R^9$-Disubstituted-3-azabicyclo[4.1.0]heptanes (XXIV)

These compounds can be prepared from methyl 1-benzyloxycarbonyl-1,2,5,6-tetrahydropyridine-4-carboxylate. Deprotonation with strong base, such as lithium diisopropylamide or lithium hexamethyldisilazide, can be followed by reaction with formaldehyde and protection of the resulting primary alcohol as its tetrahydropyranyl derivative, to give methyl 1-benzyloxycarbonyl-2-tetrahydropyranyloxymethyl-1,2,5,6-tetrahydropyridine-4-carboxylate. Processing of this compound using methodology described in Section XVI provides 3-benzyloxycarbonyl-6-hydroxymethyl-2-tetrahydropyranyloxymethyl-3-azabicyclo -[4.1.0]heptane, which can be converted into the desired disubstituted compound using chemistry from Sections VIII and XI.

1,7-$R^6$, $R^7$-Disubstituted-3-azabicyclo[4.1.0]heptanes (XXVII)

Methyl 1-benzyloxycarbonyl-1,2,5,6-tetrahydropyridine-3-carboxylate can be reduced with diisobutylaluminum hydride, and the resulting primary alcohol protected as its tetrahydropyranyl derivative. Cyclopropanation with ethyl diazoacetate in the presence of rhodium acetate then yields the ethyl ester of 3-benzyloxycarbonyl-1-tetrahydropyranyl-oxymethyl-3-azabicyclo[4.1.0]heptane-7-carboxylic acid. Processing of this compound as in Section XII delivers the desired substitution.

Alternatively, tert-butyl 1-benzyloxycarbonyl-1,2,5,6-tetrahydropyridine-3-carboxylate can be cyclopropanated using ethyl diazoacetate under molybdenum hexacarbonyl catalysis, to give 1-tert-butyl 7-ethyl 3-benzyloxycarbonyl-3-azabicyclo[4.1.0]heptane-1,7-dicarboxylic acid. Application of chemistry described in Section XII can be used to synthesize the desired disubstituted compound.

1,6-R$^6$,R$^9$-Disubstituted-3-azabicyclo[4.1.0]heptanes(XXVIII)

Addition of benzylamine to 1-tetrahydropyranyloxy-3-buten-2-one, followed by Wittig olefination of the ketone with methyltriphenylphosphonium bromide and base, provides 4-benzylamino-2-methylene-1-(tetrahydropyranyloxy)butane. Amide formation with monoethyl malonate, using carbonyldiimidazole as a condensing agent then provides a dicarbonyl compound, which is subjected to diazo transfer using p-toluenesulfonyl azide or p-carboxyphenylsulfonyl azide under the influence of potassium t-butoxide or potassium hydride. Alternatively, the procedure of Koskinen, *J. Chem. Soc, Chem. Commun.*, 1990, 652 can be utilized. The resulting diazo compound is treated with rhodium acetate in refluxing benzene, according to the procedure of Kametani, *Chem. Pharm. Bull.*, 1985, 61, to provide the ethyl ester of 3-benzyl-2-oxo-6-tetrahydropyranyloxymethyl-3-azabicyclo[4.1.0]heptane-1-carboxylic acid. Lithium aluminum hydride reduction gives a compound of formula XXVIII wherein the 1-substituent is hydroxymethyl and the 6-substituent is tetrahydropyranyloxymethyl. This compound can be processed into the desired sidechain by the chemistry described in Sections XI and VIII.

1,5-R$^6$,R$^5$-Disubstituted-3-azabicyclo[4.1.0]heptanes (XXIX)

2-Ethenyl-1,3-propanediol can be prepared using the methodology of Meyer, *Syn. Commun.*, 1986, 261. Monoprotection as the tetrahydropyranyl derivative can be followed by mesylation of the remaining primary alcohol, and displacement with benzylamine, to provide 4-(benzyl-amino)-3-tetrahydropyranyloxymethyl-1-butene. Amide formation with monoethyl malonate, diazo transfer and cyclization as in Section XXVIII then provides the ethyl ester of 3-benzyl-2-oxo-5-tetrahydropyranyloxymethyl-3-azabicyclo[4.1.0]heptane-1-carboxylic acid. Lithium aluminum hydride reduction gives 3-benzyl-1-hydroxymethyl-5-tetrahydropyranyloxymethyl-3-azabicyclo[4.1.0]heptane, which can be transformed into the desired substituent using the chemistry outlined in Sections XI and VIII.

5,7-R$^5$,R$^7$-Disubstituted-3-azabicyclo[4.1.0]heptanes (XXXII)

Cycloaddition of 5-tetrahydropyranyloxy-1,3-pentadiene with the benzyl ester of methylenecarbamic acid provides 1-benzyloxycarbonyl-3-tetrahydropyranyloxymethyl-1,2,3,6-tetrahydropyridine. Cyclopropanation with ethyl diazoacetate and rhodium acetate then gives the ethyl ester of 3-benzyloxycarbonyl-5-tetrahydropyranyloxymethyl-3-azabicyclo[4,1,0-]heptane-7-carboxylic acid. Conversion into the desired disubstituted compound can then be carried out as described in Section XII.

5,6-R$^5$,R$^9$-Disubstituted-3-azabicyclo[4.1.0]heptanes (XXXIV)

Addition of allylamine to ethyl 4-chloroacetoacetate, followed by protection of the resulting secondary amine as its benzyloxycarbonyl derivative provides ethyl N-allyl-N-benzyloxycarbonyl-4-amino-3-oxo-butanoic acid. Diazo transfer and rhodium-mediated cyclization can then be carried out, as described in Section XXVIII, to provide ethyl 3-benzyloxycarbonyl-5-oxo-3-azabicyclo[4.1.0]heptane-6-carboxylate. Olefination with (methoxymethyl)triphenyl-phosphonium chloride and base, followed by mild acid hydrolysis, then gives ethyl 3-benzyloxycarbonyl-5-carboxaldehyde-3-azabicyclo[4.1.0]heptane-6-carboxylate. Oxidation of the aldehyde to a carboxylic acid can be carried out with sodium chlorite or tetra-n-butylammonium permanganate. The resulting compound of formula XXXIV, wherein R$^5$ is a carboxylic acid and R$^9$ is an ethyl ester, can be transformed into the desired disubstituted compound using the procedure outlined in Section XII.

6,6-R$^7$ substituted-3-azabicyclo[3.1.0]hexanes(XXXVII)

These compounds are derived from methyl tert-butyl 3-benzyloxycarbonyl-3-azabicyclo[3.1.0]hexane-6,6-dicarboxylic acid, which can be prepared by cyclopropataion of 1-benzyloxycarbonyl-3-pyrroline using the method of Ohishi, *Synthesis*, 1980, 690 or Peace and Wulfman, *Synthesis*, 1973, 137. Removal of the tert-butyl ester can be effected by brief treatment with trifluoroacetic acid; the liberated carboxylic acid can then be transformed into an amino group by the procedure of Baldwin, *J. Chem. Soc, Chem, Commun.*, 1988, 775. The resulting compound of formula XXXVII, wherein the 3-substituent is benzyloxycarbonyl and the 6-substituents are amino and methoxycarbonyl, can then be protected as its tert butoxycarbonyl derivative; alkylation of the amine, as in Section VII, can be carried out to provide the N-methyl and N-ethyl derivatives. Reduction of the ester functionality with lithium borohydride gives the primary alcohol, which can be processed as in Section IX to give aminomethyl substituents.

When at least one of the 6-substituents is methyl, the carboxylic acid resulting from deprotection of the tert-butyl ester is reduced with diborane, to provide a compound of the formula XXXVII wherein the 3-substituent is benzyloxycarbonyl and the 6-substituents are hydroxymethyl and Methoxycarbonyl. Replacement of the benzyloxycarbonyl group by a benzyl group, as in Section XI, is then followed by tosylation of the alcohol. Reduction with lithium aluminum hydride yields a compound of formula XXXVII wherein the 3-substituent is benzyl, and the 6-substituents are methyl and hydroxymethyl. The hydroxymethyl group can be transformed into the desired substituent by the methods outlined in Section VIII.

Alternatively, to generate compounds where at least one of the 6-substituents is methyl, methodology of Loozen, *J. Org. Cham*, 1976, 2965 can be employed. Thus, 1-benzyloxycarbonyl-3-pyrroline can be reacted with dibromocarbene, to provide 3-benzyloxycarbonyl-6,6-dibromo-3-azabicyclo[3.1.0]hexane. One of the bromines is replaced by methyl, using n-butyllithium and methyl iodide. The resulting compound is again subjected to metal-halogen exchange, using butyllithium at low temperature, and the anion is quenched with formaldehyde, to provide 3-benzyl-6-hydroxymethyl-6-methyl-3-azabicyclo[3.1.0]hexane. Formation of the initial gem-dibromocyclopropane can also be effected using phenyl(tribromomethyl)mercury. The hydroxymethyl group can be transformed into the desired substituent by the methods outlined in Section VIII.

To generate compounds in which both of the 6-substituents are aminomethyl derivatives, methyl tert-butyl 3-benzyloxycarbonyl-3-azabicyclo[3.1.0]hexane-6,6-dicarboxylic acid is once again deprotected with trifluoroacetic acid. The liberated carboxylic acid is condensed with ammonia, methylamine or ethylamine through the use of an activating agent such as dicyclohexylcarbodiimide or carbonyl diimidazole, to form the corresponding amide. The methyl ester is then hydrolyzed to the carboxylic acid under acidic or basic conditions, and a second amide is formed in similar fashion. The resulting compound of formula XXXVII wherein both 6-substituents are amides, optionally substituted with a methyl or ethyl group, is then transformed from the N-benzyloxycarbonyl derivative to the N-benzyl compound, as in Section XI. Subsequent reduction with lithium aluminum hydride provides the compound bearing two aminomethyl groups at the 6-position, which are optionally substituted with a methyl or an ethyl group. Protection as the di-tert-butoxycarbonyl derivative and removal of the benzyl group by hydrogenolysis provides the compound in a form appropriate for coupling to compound II.

1,2,6-$R^6$,$R^3$,$R^7$-Trisubstituted-3-azabicyclo[3.1.0]hexanes (XXXVIII)

A. $R^7$ is a methyl group.

These compounds are derived from 1-benzylamino-2-butene, available from the reaction of benzylamine with 1-bromo-2-butene. Amide formation with monoethyl malonate, diazo transfer, and cyclization using rhodium acetate can be carried out as in Section XXVIII, to provide the ethyl ester of 3-benzyl-6-methyl-2-oxo-3-azabicyclo[3.1.0]hexane-1-carboxylic acid. Reduction with lithium borohydride and protection of the resulting hydroxymethyl group as its tetrahydropyranyl ether provides a compound of the formula XXXVIII where $R^3$ is a double bond to oxygen, $R^6$ is a tetrahydropyranyloxymethyl group, and $R^7$ is a methyl group. Subjection of this compound to methyllithium followed by sodium cyanoborohydride, according to the work of Shibagaki, *Heterocycles*, 1986, 423, gives 3-benzyl-2,6-dimethyl-1-tetrahydropyranyloxymethyl-3-azabicyclo[3.1.0]-hexane, wherein the 1-substituent can be elaborated as in Section X, to give compounds of the formula XXXVIII where $R^3$ and $R^7$ are methyl groups.

Alternatively, the amide functionality in the 1-tetrahydropyranyloxymethyl compound can be reduced to the carbinolamine with sodium bis(2-methoxyethoxy)aluminum hydride (Red-Al) at −78° C. Methylation of the alcohol functionality with methyl iodide can be followed by displacement with trimethylsilylcyanide to provide a compound of formula XXXVIII wherein $R^3$ is cyano, $R^6$ is tetrahydropyranyloxymethyl and $R^7$ is methyl. The cyano group can be transformed at this point into the desired substituent by the methods outlined in Section VI. The 1-substituent is converted from the tetrahydropyranyloxymethyl substituent by the chemistry described in Section IX or Section X.

B. $R^6$ is a methyl group.

Reaction of 3-methyl-1,4-pentadiene with less than one equivalent of osmium tetroxide provides a diol, which can be mono-protected at the primary alcohol to give 2-hydroxy-3-methyl-1-tetrahydropyranyloxy-4-pentene. Submission of this compound to the chemistry described by Takano, *Heterocycles* 1989, 1861, yields 1-benzyloxycarbonyl-3-methyl-2-tetrahydropyranyloxymethyl-3-pyrroline. Cyclopropanation with ethyl diazoacetate under rhodium acetate catalysis provides a compound of the formula XXXVIII wherein $R^3$ is tetrahydropyranyloxymethyl, $R^6$ is methyl and $R^7$ is ethoxycarbonyl. Hydrolysis of the ethyl ester under basic conditions provides a carboxylic acid as the 6-substituent; this can be transformed into an amine or an alkylated amine using the chemistry described in Section VIII. Alternatively, the benzyloxycarbonyl group can be replaced by a benzyl group, as in Section XI; the ester group can then be converted to an (alkyl)aminomethyl group as in Section VIII. After protection of any amine groups at the 6-position, the tetrahydropyranyloxymethyl group can be converted into the desired substituent using the chemistry in Section IX or X.

When both the 1- and 6-substituents are methyl, the same chemistry can be effected starting with 1-benzyloxycarbonyl-2,3-dimethyl-3-pyrroline.

C. $R^3$ is a methyl group.

In this case, the starting material is the tert-butyl ester of 1-benzyloxycarbonyl-2-methyl-3-pyrroline-3-ester carboxylic acid, obtainable from the chemistry described in Section XII, where tert-butyl crotonate is employed in place of tert-butyl acrylate. Cyclopropanation as above with ethyl diazoacetate provides a compound of the formula XXXVIII wherein $R^3$ is methyl, $R^6$ is tert-butoxycarbonyl, and $R^7$ is ethoxycarbonyl. Trifluoroacetic acid can be used to hydrolyze the tert butyl ester; subsequent Curtius rearrangement with diphenylphosphoryl azide in tert-butanol provides a protected 1-amino substituent, which can be alkylated as in Section VIII if desired. Alternatively, the acid moiety at the 1-position can be reduced with diborane to provide a hydroxymethyl substituent, which can be elaborated as in Section VIII or IX. The ethyl ester at the 6-position is then either hydrolyzed under basic conditions and the resulting acid subjected to a similar Curtius rearrangement and further elaboration, or reduced to the hydroxymethyl group with lithium borohydride. The hydroxymethyl group can then be converted into the desired substituent by the chemistry described in Section IX.

1,6,6-$R^6$,$R^7$,$R^{25}$-Trisubstituted-3-azabicyclo[3.1.0]hexanes (XLI)

A. $R^6$ is a methyl group.

These compounds can be prepared from 1-benzyloxycarbonyl-3-methyl-3-pyrroline by cyclopropanation with tert-butyl methyl malonate or its diazo derivative, as outlined in Section XXXVII. The resulting tert-butyl methyl 3-benzyloxycarbonyl-1-methyl-3-azabicyclo[3.1.0]-hexane-6,6-dicarboxylic acid can be further functionalized as described in Section XXXVII.

B. $R^7$ is a methyl group.

Compounds of this type are derived from 1-benzyloxycarbonyl-3-tetrahydropyranyloxymethyl-3-pyrroline. This starting material can be prepared from 1-benzyloxycarbonyl-3-pyrrolidinone by deprotonation with strong base, such as lithium hexamethyldisilazide, followed by quenching with formaldehyde. The free alcohol is protected as its tetrahydropyranyl derivative, and the ketone is reduced with sodium borohydride. Dehydration of the resulting alcohol with phosphorus oxychloride in pyridine gives the requisite starting material.

Cyclopropanation with ethyl diazoacetate under rhodium acetate catalysis provides the ethyl ester of 3-benzyloxyacetatecarbonyl-1-tetrahydropyranyloxymethyl-3-azabicyclo[3.1.0]-hexane-6-carboxylic acid, which can be methylated at the 6-position by deprotonation with strong base such as potassium hydride or lithium hexamethyldisilazide, and reaction of the derived enolate with methyl iodide. The ester can then be hydrolyzed using sodium hydroxide in methanol, and the resulting carboxylic acid functionalized as desired, using the methods described in Sections XI or XXXVIII(c).

Alternatively, the pyrroline starting material can be cyclopropanated as in Section XXXVII, to provide t-butyl methyl 3-benzyloxycarbonyl-1-tetrahydropyranyloxymethyl-3-azabicyclo[3.1.0]hexane-6,6-dicarboxylic acid. This can be processed as in Section XXXVII to generate 3-benzyloxycarbonyl-6-hydroxymethyl-6-methyl-1-tetrahydropyranyloxymethyl-3-azabicyclo[3.1.0]hexane. Use of chemistry outlined in Section XI then gives the desired substitution pattern.

1,5,6-$R^6$,$R^9$,$R^7$-Trisubstituted-3-azabicyclo[3.1.0]hexanes (XLII)

A. $R^7$ is a methyl group.

1-Bromo-2-tetrahydropyranyloxymethyl-2-butene can be reacted with benzylamine, and the resulting secondary amine condensed with the monoethyl ester of malonic ester, as described in Section XXVIII. Diazo transfer and intramolecular cyclopropanation, as described in Section XXVIII, then provides ethyl 3-benzyl-6-methyl-2-oxo-5-tetrahydropyranyloxymethyl-3-azabicyclo[3.1.0]hexane-1-carboxylic acid. Lithium aluminum hydride reduction gives a compound of formula XLII wherein the 1-substituent is hydroxymethyl, the 5-substituent is tetrahydropyranyloxymethyl, and the 6-substituent is methyl. This compound can be processed into the desired sidechain by utilizing the chemistry described in Sections XI and VIII.

B. $R^6$ is a methyl group.

These compounds are derived from 1-chloro-2-methyl-4-tetrahydropyranyloxy-2-butene, whose preparation has been described Schmid, Helv. Chim. Acta, 1982, 684. Processing of this compound as in Section A above provides 3-benzyl-1-hydroxymethyl-5-methyl-6-tetrahydropyranyloxymethyl-3-azabicyclo[3.1.0]hexane. This compound can also be transformed into the desired sidechain by utilizing the chemistry described in Sections XI and VIII.

2,4,6-$R^3$,$R^{10}$,$R^7$-Trisubstituted-3-azabicyclo[3.1.0]hexanes (XLV)

A. $R^7$ is a methyl group.

To prepare compounds of this type, 3-benzyl-6-methyl-3-azabicyclo[3.1.0]hexane (a preparation for which is outlined in Section VII) is transformed into 3-benzyl-2-cyano-6-methyl-3-azabicyclo[3.1.0]hexane by the method described in Section X. Subsequent hydrolysis of the nitrile under acidic or basic conditions can be followed by lithium aluminum hydride reduction and protection of the resulting primary alcohol as its tetrahydropyranyl derivative. Further functionalization can be carried out as in Section XIV to provide the desired substitution pattern.

B. $R^3$ is a methyl group.

These compounds are derived from 1-benzyloxycarbonyl -2-methyl-3-pyrroline. Cyclopropanation with ethyl diazoacetate, as described in Section X, can be followed by ester reduction with lithium borohydride, and protection of the resulting primary alcohol as its tetrahydropyranyl derivative, to provide 3-benzyloxycarbonyl-2-methyl-6-tetrahydropyranyloxymethyl-3-azabicyclo[3.1.0]hexane. Removal of the benzyloxycarbonyl group by hydrogenolysis can then be followed by the introduction of a cyano group at the 4-position. The 4-cyano-2-methyl-6pyranyloxymethyl-3-azabicyclotetrahydro-3.1.0]hexane obtained in this way can then be converted to the desired trisubstituted 3-azabicyclo[3.1.0]hexane by the methods outlined in Section X.

1,2,7-$R^6$,$R^4$,$R^7$-Trisubstituted-3-azabicyclo[4.1.0]heptanes (XLVI)

A. $R^7$ is a methyl group.

Reaction of benzylamine with 5-bromopent-2-ene gives 5-benzylamino-2-pentene, which can be condensed with the half-ester of malonic acid, as described in Section XXVIII. Subsequent diazo transfer and cycloaddition, according to Section XXVIII, provides ethyl 3-benzyloxycarbonyl-7-methyl-2-oxo-3-azabicyclo[4.1.0]heptane-1-carboxylate. Processing of this compound as in Section XXXVIII provides the desired trisubstituted compound.

B. $R^6$ is a methyl group.

Cycloaddition of the benzyl ester of methylenecarbamic acid with 3-methyl-5-tetrahydropyranyloxy-1,3-pentadiene yields 1-benzyloxycarbonyl-3-methyl-2-tetrahydropyranyloxymethyl-1,2,5,6-tetrahydropyridine. Cyclopropanation with ethyl diazoacetate, as described above, then provides a compound of formula XLVI, where $R^7$ is an ethyl ester, $R^6$ is methyl, and $R^4$ is tetrahydropyranyloxymethyl. This compound can be transformed into the desired trisubstituted sidechain using methodology described in Section XI.

C. $R^4$ is a methyl group.

Cycloaddition of the benzyl ester of methylenecarbamic acid with 3-tetrahydropyranyloxymethyl-1,3-pentadiene provides 1-benzyloxycarbonyl-2-methyl-3-tetrahydropyranyl-oxymethyl-1,2,5,6-tetrahydropyridine. Cyclopropanation with ethyl diazoacetate gives a compound of formula XLVI, wherein $R^7$ is an ethyl ester group, $R^6$ is tetrahydropyranyloxymethyl, and $R^4$ is methyl. Chemistry described in Section XII can be used to transform this compound into the desired sidechain.

2,7,7-$R^7$,$R^{25}$-Trisubstituted-3-azabicyclo[4.1.0]heptanes (L)

A. $R^4$ is a methyl group.

Cycloaddition of the benzyl ester of methylenecarbamic acid with 1,3-pentadiene provides 1-benzyloxycarbonyl-2-methyl-1,2,5,6-tetrahydropyridine. Cyclopropanation with tert-butyl methyl malonate or its diazo derivative, as outlined in Section XXXVII, then gives a compound of formula L wherein $R^4$ is a methyl group, $R^7$ is a methyl ester group and $R^{25}$ is a tert-butyl ester group. Chemistry outlined in Section XXXVII is then used to convert this compound.

B. $R^7$ is a methyl group.

Reaction of 1-benzyloxycarbonyl-2-tetrahydropyranyloxymethyl-1,2,5,6-tetrahydropyridine with bromoform under basic conditions, as in Section XXXVII, gives 3-benzyloxycarbonyl-7,7-dibromo-2-tetrahydropyranyloxymethyl-3-azabicyclo[4.1.0]heptane, which can be further converted into the desired compound by applying methods described in Section XXXVII.

1,6,7-$R^6$,$R^9$,$R^7$-Trisubstituted-3-azabicyclo[4.1.0]heptanes (LVIII)

A. $R^7$ is a methyl group.

Addition of benzylamine to 1-tetrahydropyranyloxy-3-buten-2-one, followed by Witting olefination of the ketone with ethylidene triphenylphosphorane, provides 5-benzyl-amino-3-tetrahydropyranyloxymethyl-2-pentene. Amide formation with monoethyl malonate, followed by diazo transfer and rhodium-catalyzed cycloaddition, can be carried out as described in Section XXVIII to provide the ethyl ester of 3-benzyl-7-methyl-2-oxo-6-tetrahydropyranyloxymethyl-3-azabicyclo[4.1.0]heptane-1-carboxylic acid. This compound can be further processed as in Section XXVIII.

B. $R^9$ is a methyl group.

Addition of benzylamine to methyl vinyl ketone, followed by Peterson olefination of the ketone with ethyl 2-trimethylsilylacetate and base, gives an unsaturated ester which can be reduced with diisobutylaluminum hydride. The resulting primary alcohol is protected as its tetrahydropyranyloxy derivative, to give tetrahydropyranylprotected 5-benzylamino-3-methylpent-2-en-1-ol. Amide formation and cycloaddition as described in Section XXVIII then provides the ethyl ester of 3-benzyl-6-methyl-2-oxo-7-polymethyl-3-azabicyclo[4.1.0]heptane-1-carboxylic acid. This can be processed into the desired derivative using chemistry outlined in Section XXVIII.

C. $R^6$ is a methyl group.

Addition of benzylamine to 1-tert-butyldimethylsilyoxy-3-buten-2-one, followed by Peterson olefination of the ketone with ethyl 2-trimethylsilylacetate and base, gives an unsaturated ester which can be reduced with diisobutylaluminum hydride. The resulting primary alcohol can be protected as its tetrahydropyranyloxy derivative. Amide formation, cycloaddition and lithium aluminum hydride reduction, as described in Section XXVIII, then gives 3-benzyl-6-tert-butyldimethylsilyloxymethyl-1-hydroxymethyl-7-tetrahydropyranyloxymethyl-3-azabicyclo[4.1.0]-heptane. Reduction of the primary alcohol to a methyl group at position 1 can be carried out using the methodology described in Section VI. Subsequent removal of the tert-butyldimethylsilyl protecting group at position 6 can then be effected using tetra-n-butyl ammonium fluoride in tetrahydrofuran solution. The resulting 3-benzyl-6-hydroxymethyl-1-methyl-7-tetrahydropyranyloxymethyl-3 -azabicyclo[4.1.0]heptane can be transformed into the desired compound using the chemistry in Sections XI and VIII.

4,5,7-$R^3$,$R^5$,$R^7$-Trisubstituted-3-azabicyclo[4.1.0]heptanes (LXX)

A. $R^3$ is a methyl group.

1-Benzyloxycarbonyl-1,6-dihydro-3(2H)-pyridinone can be cyclopropanated with ethyl diazoacetate under the influence of molybdenum hexacarbonyl, to give the ethyl ester of 3-benzyloxycarbonyl-5-oxo-3-azabicyclo[4.1.0]-heptane-7-carboxylic acid. Treatment of this compound with base, such as lithium hexamethyldisilazide or potassium tert-butoxide, followed by methyl iodide, serves to introduce a methyl group at the 4-position. Wittig reaction and further processing of this compound as in Section XXXIV delivers the desired trisubstituted compound.

B. $R^5$ is a methyl group.

Deprotonation of the ethyl ester of 3-benzyloxycarbonyl-5-oxo-3-azabicyclo[4.1.0]heptane-7-carboxylic acid with a strong base, such as lithium hexamethyldisilazide or potassium tert-butoxide, followed by quenching of the enolate with formaldehyde, gives a primary alcohol which can be protected as its tetrahydropyranyloxy derivative. The resulting ethyl 3-benzyloxycarbonyl-5-oxo-4-tetrahydropyranyloxymethyl-3-azabicyclo[4.1.0]heptane-7-carboxylate is subjected to olefination with base and methyltriphenylphosphonium bromide. Catalytic hydrogenation of the double bond, followed by reintroduction of the benzyloxycarbonyl group, gives the ethyl ester of 3-benzyloxycarbonyl-5-methyl-4-tetrahydropyranyloxymethyl-3-azabicyclo[4.1.0]-heptane-7-carboxylic acid, which can be further elaborated as in Section XI.

C. $R^7$ is a methyl group.

1-Benzyloxycarbonyl-5-hydroxy-1,2,5,6-tetrahydropyridine can be transformed into 3-benzyloxycarbonyl-7-bromo-7-methyl-5-hydroxy-3-azabicyclo[4.1.0-]heptane using methods described in Section XXXVII. Reaction with tri-(n-butyl)tin hydride then yields the debrominated compound. Oxidation of the alcohol to the ketone with pyridinium chlorochromate or a Swern oxidation provides 3-benzyloxycarbonyl-7-methyl-5-oxo-3-azabicyclo[4.1.0]-heptane. Deprotonation, quenching with formaldehyde, and protection as the tetrahydropyranyl derivative as described in Section B above, yields 3-benzyloxycarbonyl-7-methyl-5-oxo-4-tetrahydropyranyloxymethyl-3-azabicyclo[4.1.0]-heptane. Transformation of the ketone to the homologated carboxylic acid can be effected as described in Section XXXIV. The resulting 3-benzyloxycarbonyl-7-methyl-4-tetrahydropyranyloxymethyl-3-azabicyclo[4.1.0]heptane-5-carboxylic acid can be converted as in Section XI to give the desired substituents.

The prodrugs of this invention may be prepared by conventional peptide coupling reactions coupling the free amino group in the 7-substituent of the compound of formula I with an amino acid or a polypeptide, e.g. dipeptide, chain. The coupling reaction is generally conducted at a temperature of about −30 to about 80° C., preferably about 0 to about 25° C. Suitable coupling reagents are usually present, such as dicyclohexylcarbodiimide with hydroxybenzotriazole (HBT), N-3-dimethylaminopropyl-N′-ethylcarbodiimide with HBT, 2-ethoxy-1-ethoxycarbonyl-1,2-dihydroquinoline, carbonyl diimidazole with HBT, and diethylphosphorylcyanide. The reaction is conducted in an inert solvent, such as acetonitrile, methylene chloride, chloroform, dimethylformamide, dioxane, tetrahydrofuran, dimethoxyethane, or water, or a mixture of at least two of such solvents.

The pharmaceutically acceptable acid addition salts of compounds (I) are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, methanesulfonic, p-toluenesulfonic, cinnamic, fumaric, phosphonic, hydrochloric, hydrobromic, hydroiodic, sulfamic, and sulfonic acid.

The pharaceutically acceptable cationic salts of compounds (I) may be prepared by conventional methods from the corresponding acids, e.g. by reaction with about one equimolar amount of a base. These cationic salts do not increase the toxicity of the compound toward animal organisms. Examples of suitable cationic salts are those of alkali metals such as sodium or potassium, alkaline earth metals such as magnesium or calcium, and ammonium or organic amines such as diethanolamine or N-methylglucamine.

The novel compounds of formula I and the pharmaceutically acceptable acid addition salts thereof are useful in the treatment of bacterial infections of broad spectrum, particularly the treatment of gram-positive bacterial strains.

The compounds of the invention may be administered alone, but will generally be administered in admixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of 5-5000 ppm, preferably 25-500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, compounds can be administered intramuscularly or subcutaneously at dosage levels of about 0.1-50 mg/kg/day, advantageously 0.2-10 mg/kg/day given in a single daily dose or up to 3 divided doses.

The invention also provides pharmaceutical compositions comprising an antibacterially effective amount of a compound of the formula (I) together with a pharmaceutically acceptable diluent or carrier.

The compounds of the invention can be administered to humans for the treatment of bacterial diseases by either the oral or parenteral routes, and may be administered orally at dosage levels of about 0.1 to 500 mg/kg/day, advantageously 0.5-50 mg/kg/day given in a single dose or up to 3 divided doses. For intramuscular or intravenous administration, dosage levels are about 0.1-200 mg/kg/day, advantageously 0.5-50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The temperatures are in degrees Celsius in the following preparations and examples.

PREPARATION A

1. N-Benzyl-N-(2-cyanoethyl)-3-amino-1,2-propanediol

A solution of glycidol (25.4 ml, 0.383 mol) and 3-(benzylamino)propionitrile (50 ml, 0.319 mol) in ethanol (383 ml) was heated to reflux for 65 hours. Removal of solvent under reduced pressure left a yellow oil, which was partitioned between ethyl acetate and water. The organic layer was washed with water, washed with saturated sodium chloride solution and dried over sodium sulfate. Filtration and concentration in vacuo provided an oil (75 g) which was purified by column chromatography (eluant: 5% methanol in chloroform) to give the title product (55.3 g, 0.236 mol, 74% yield) as a colorless oil. $^1$H NMR (CDCl$_3$) 7.35 (m, 5H), 3.86 (d, J=13 Hz, 1H), 3.8 (m, 2H), 3.64 (d, J=13 Hz, 1H), 3.20 (bs, 1H), 3.20 )bs, 1H), 2.95 (m, 1H), 2.84 (m, 1H), 2.75 (dd, J=12, 8 Hz, 1H), 2.63 (dd, J=13, 4 Hz, 1H), 2.50 (m, 2H).

2.

N-Benzyl-N-(2-cyanoethyl)-3-amino-1,2-bis(methanesulfonyloxy) propane

A solution of the title compound of Preparation A.1. (11.2 g, 47.8 mmol) and triethylamine (8.14 ml, 105 mmol) in methylene chloride (480 ml) was cooled to $-10°$ and treated with methanesulfonyl chloride (16.6 ml, 119 mmol). After 85 minutes at $-10°$, the reaction mixture was poured into a saturated aqueous sodium bicarbonate solution. The aqueous layer was extracted twice with methylene chloride, and the combined organic layers were dried over magnesium sulfate. Filtration and removal of solvent in vacuo provided the title product as a yellow oil (18.0 g, 47.6 mmol, 99% yield) which was used without purification. $^1$H NMR (CDCl$_3$) 7.31 (m, 5H), 4.75 (m, 1H), 4.45 (dd, J=12, 3Hz, 1H), 4.27 (dd, J=12, 6 Hz, 1H), 3.68 (AB quartet, J=12 Hz, 2H), 3.07 (s, 3H), 3.02 (s, 3H), 2.88 (m, 4H), 2.48 (m, 2H).

3. 3-Benzyl-1-cyano-3-azabicyclo[3.1.0]hexane

N-Benzyl-N-(2-cyanoethyl)-2,3-dimethanesulfonylpropylamine (32.25 g, 85.2 mmol) was dissolved in benzene (800 ml), cooled to $-10°$, and treated with sodium hexamethyldisilazide (170 ml of a 1M solution in tetrahydrofuran, 170 mmol). After 2 hours, the reaction mixture was quenched with saturated ammonium chloride solution, and the mixture was extracted three times with methylene chloride. The combined organic layers were dried over magnesium sulfate, filtered and concentrated in vacuo. Chromatographic purification (eluant: 4:1 hexane:ethyl acetate) gave the title product as a yellow oil (8.23 g, 41.5 mmol, 49% yield. $^1$H NMR (CDCl$_3$): 7.26 (m, 5H), 3.59 (s, 2H), 3.11 (d, J=9 Hz, 1H), 2.94 (d, J=9 Hz, 1H), 2.54 (d, J=9 Hz, 1H), 2.47 (dd, J=10, 4 Hz, 1H), 2.03 (m, 1H), 1.57 (m, 1H), 1.10 (dd, J=8, 5 Hz, 1H).

4. 1-Aminomethyl-3-benzyl-3-azabicyclo[3.1.0]hexane

Lithium aluminum hydride (70 ml of a 1M solution in diethyl ether, 70 mmol) was added to a solution of 3-benzyl-1-cyano-3-azabicyclo[3.1.0]hexane (3.35 g, 16.9 mmol) in tetrahydrofuran (200 ml). After 18 hours at room temperature, the reaction mixture was treated sequentially with water (2.6 ml), sodium hydroxide (2.6 ml of a 15% aqueous solution), and water (7.8 ml). The mixture was filtered, and the filtrate was concentrated under reduced pressure to provide the title product as a viscous, slightly yellow oil (3.47 g, 100% yield), which was used without purification. $^1$H NMR (CDCl$_3$): 7.20 (m, 5H), 3.54 (AB quartet, J=12 Hz, 2H), 2.92 (d, J=8 Hz, 1H), 2.87 (d, J=9 Hz, 1H), 2.81 (d, J=13 Hz, 1H), 2.59 (d, J=13 Hz, 1H), 2.33 (dd, J=8, 4 Hz, 1H), 2.25 (d, J=7 Hz, 1H), 1.10 (m, 1H), 0.97 (m, 1H), 0.30 (dd, J=8, 5 Hz, 1H).

5.

3-Benzyl-1-[(N-tert-butoxycarbonyl)ainomethyl]-3-azabicyclo[3.1.0]hexane

A solution of the title compound of Preparation A.4. (2.19 g, 10.8 mmol) and triethylamine (1.8 ml, 13 mmol) in aqueous dioxane (8.8 ml water and 80 ml dioxane) was treated with di-tert-butyl dicarbonate (2.6 g, 11.9 mmol). After 1 hour at room temperature, the reaction mixture was partitioned between saturated aqueous sodium bicarbonate and dichloromethane. The organic layer was dried over sodium sulfate, filtered, and concentrated in vacuo to provide a viscous, slightly yellow oil. Purification by column chromatography (eluant: 95:5:0.5 chloroform: methanol: concentrated ammonium hydroxide) provided the title product as a colorless oil (3.27 g, 10.8 mmol, 100% yield). $^1$H NMR (CDCl$_3$): 7.26 (m, 5H), 4.54 (bs, 1H), 3.60 (AB quartet, J=13 Hz, 2H), 3.35 (m, 1H), 3.11 (dd, J=14, 6 Hz, 1H), 2.93 (m, 2H), 2.41 (dd, J=10, 4 Hz, 1H), 2.31 (d, J=8 Hz, 1H), 1.44 (s, 9H), 1.23 (m, 1H), 1.07 (m, 1H), 0.40 (dd, J=8, 4 Hz, 1H).

6.

1-[(N-tert-butoxycarbonyl)aminomethyl)]-3-azabicyclo[3.1.0]hexane

The title compound of Preparation A.5. (3.27 g, 10.8 mmol) and 10% palladium on carbon (3.44 g) were mixed with ethanol (500 ml), and the resulting suspension was treated with ammonium formate (2.04 g, 32.5 mmol) and heated to 60° for 7 minutes. The reaction mixture was cooled, filtered through diatomaceous earth (Celite (trademark)), and the solid cake was rinsed thoroughly with chloroform. Removal of solvent in vacuo provided a yellow-white residue, which was purified by column chromatography (eluant: 89:10:1 chloroform: methanol: concentrated ammonium hydroxide) to provide the title product as a white solid, mp 131.5°–132.5° (1 53 g, 7.2 mmol, 67% yield). $^1$H NMR (CDCl$_3$): 4.63 (bs, 1H), 3.31 (dd, J=12, 6 Hz, 1H), 3.24 (m, 1H), 2.88 (m, 4H), 1.40 (s, 9H), 1.23 (m, 1H), 0.54 (m, 1H), 0.42 (m, 1H).

Preparation B

1.

1-[(N-Acetyl)aminomethyl]-3-benzyl-3-azabicyclo-[3.1.0]hexane

A mixture of the title compound of Preparation A.4. (1.65 g, 8.16 mmol) and triethylamine (1.7 ml, 12 mmol) was treated with acetic anhydride (20 ml) and allowed to stir at room temperature for 18 hours. The reaction solution was diluted with chloroform, washed with saturated aqueous sodium bicarbonate, washed with saturated aqueous sodium chloride, dried over magnesium sulfate and filtered. Removal of solvent in vacuo provided the title product as a viscous yellow oil (1.97 g, 8.06 mmol, 99% yield). $^1$H NMR (CDCl$_3$) 7.25 (m, 5H), 5.46 (bs, 1H), 3.61 (d, J=13 Hz, 1H), 3.51 (d, J=13 Hz, 1H), 3.48 (m, 1H), 3.16 (dd, J=14, 5Hz, 1H), 2.90 (d, J=9 Hz, 2H), 2.38 (dd, J=9, 3Hz, 1H), 2.25 (d, J=9 Hz, 1H), 1.94 (s, 3H), 1.22 (m, 1H), 1.05 (m, 1H), 0.39 (dd, J=8, 4Hz, 1H).

2.

1-[(N-Acetyl)aminomethyl]-3-azabicyclo[3.1.0]hexane

A solution of the title compound of Example B.1. (197.4 mg, 0.80 mmol) in ethanol (15 mol) was treated with palladium on carbon (10%, 254.4 mg, 0.24 mmol) and ammonium formate (151.3 mg, 2.4 mmol). The reaction mixture was allowed to stir at room temperature for 30 minutes, then was filtered through diatomaceous earth (Celite (trademark)). The colorless filtrate was concentrated in vacuo to provide the title product as a colorless semi-solid (149.4 mg, quantitative). H NMR (CD$_3$OD): 3.42 (s, 2H), 3.25 (m, 4H), 2.00 (s, 3H), 1.6 (m, 1H), 0.84 (m, 1H), 0.71 (m, 1H).

PREPARATION C

1.

3-Benzyl-1-[N-(tert-butoxycarbonyl)ethylaminomethyl]-3-azabicyclo[3.1.0]hexane

The compound of Preparation A.4. (1.1 g, 5.4 mmol) was dissolved in methanol (55 ml) and treated with acetic acid (0.31 ml, 5.4 mmol), acetaldehyde (0.30 ml, 5.4 mmol) and sodium cyanoborohydride (341 mg, 5.4 mmol). The reaction mixture was allowed to stir at room temperature for 18 hours; it was then diluted with water and methylene chloride and acidified to pH 1 with 6N hydrochloric acid. Potassium carbonate was then added until the pH of the aqueous layer was 10; the mixture was extracted three times with methylene chloride, and the combined organic layers were dried over sodium sulfate, filtered and concentrated in vacuo. The residue was subjected to silica gel chromatography (eluant: 89:10:1 chloroform: methanol: concentrated ammonium hydroxide) to provide a colorless oil (390 mg, 2:1 mixture of 3-benzyl-1-ethylaminomethyl-3-azabicyclo[3.1.0]hexane and 1-aminomethyl-3-benzyl-3-azabicyclo[3.1.0]hexane). This material was dissolved in dioxane (18 ml) and water (2 ml) and treated with triethylamine (0.7 ml, 5.0 mmol) and di-tert-butyl dicarbonate (1.1 g, 5.0 mmol); the reaction mixture was allowed to stir for 18 hours at room temperature. The solution was partitioned between methylene chloride and saturated aqueous sodium bicarbonate. The aqueous layer was extracted three times with methylene chloride and the combined organic layers were dried over magnesium sulfate, filtered and concentrated in vacuo. The resulting colorless oil was subjected to purification on a Chromatotron (trademark) (eluant: 400:10:1 chloroform: methanol: concentrated ammonium hydroxide) to provide the title product as a yellow oil (277 mg, 0.84 mmol, 16% yield). $^1$H NMR (CDCl$_3$): 7.30 (m, 5H), 3.65 (bs, 2H), 3.30 (m, 4H), 3.00 (m, 2H), 2.44 (m, 2H), 1.48 (s, 9H), 1.25 (m, 1H), 1.15 (m, 1H), 1.12 (t, J=7 Hz, 3H), 0.46 (bs, 1H).

2.

1-[N-(tert-Butoxycarbonyl)ethylaminomethyl]-3-azabicyclo[3.1.0]hexane

The title compound of Preparation C.1. (266.2 mg, 0.80 mmol) was dissolved in ethanol (8 ml), treated with ammonium formate (152 mg, 2.4 mmol) and 10% palladium on carbon (280 mg) and heated to 60° for 10 minutes. The reaction mixture was filtered through diatomaceous earth (Celite (trademark)) and the filtrate concentrated in vacuo; the residue was mixed with chloroform and filtered once more to provide, after removal of solvent, a colorless oil. This material was purified by silica gel chromatography (eluant: 95:5:0.5 chloroform: methanol: conc. ammonium hydroxide) to provide the title product as a colorless oil (45.6 mg, 0.19 mmol, 24% yield). $^1$H NMR (CDCl$_3$) 3.43 (bs, 2H), 3.24 (bs, 2H), 1, 2.90 (m, 3H), 2.46 (bs, 2H), 1.42 (s, 9H), 1.22 (bs, 1H), 1.08 (t, J=7 Hz, 3H), 0.55 (m, 1H), 0.46 (m, 1H).

PREPARATION D 1. 3-Benzyl-3-azabicyclo[3.1.0]hexane-1-carboxylic acid

A mixture of 3-benzyl-1-cyano-3-azabicyclo-3.1.0]hexane (2.77 g, 14.0 mmol) and barium hydroxide (4 47 g, 14.2 mmol) in water (100 ml) was heated to reflux for 18 hours. The reaction was then cooled and brought to neutral pH with sulfuric acid. The thick white mixture was filtered and washed twice with ethanol and twice with water. The filtrate was concentrated in vacuo, and the residue mixed with hot ethanol and filtered again. The filtrate was concentrated to provide the title product (2.91 g, 13.4 mmol, 96% yield). $^1$H NMR (D$_2$O) 7.50 (bs, 5H), 4.36 (s, 2H), 3.9 (bs, 1H), 3.6 (m, 1H), 3.5 (bs, 2H), 2.14 (bs, 1H), 1.53 (bs, 1H), 1.09 (bs, 1H).

2. 3-Benzyl-1-isopropoxycarbonylamino-3-azabicyclo-[3.1.0]hexane

A mixture of the title compound of Preparation D.1. (4.72 g, 21.7 mmol), diphenylphosphoryl azide (4.68 ml, 21.7 mmol) and triethylamine (6 ml, 43 mmol) in isopropanol (210 ml) was heated to 80° for 18 hours. Volatiles were removed in vacuo and the residual oil was dissolved in benzene. The benzene solution was washed with water, aqueous sodium bicarbonate, saturated sodium chloride and then dried over magnesium sulfate. Filtration and removal of solvent in vacuo gave a dark oil which was purified by silica gel chromatography (eluant: 289:10:1 chloroform: methanol: concentrated ammonium hydroxide) to provide the title product as a yellow solid, mp 88° (3.5 g, 12.8 mmol, 59% yield). $^1$H NMR (CDCl$_3$) 7.26 (m, 5H), 4.92 (m, 2H), 3.60 (s, 2H), 3.03 (d, J=8 Hz, 1H), 2.87 (d, J=9 Hz, 1H), 2.61 (bs, 1H), 2.51 (d, J=8 Hz, 1H), 1.52 (bs, 1H), 1.32 (bs, 1H), 1.21 (d, J=6 Hz, 6H), 0.73 (dd, J=8, 4 Hz, 1H).

3. 1-Amino-3-benzyl-3-azabicyclo[3.1.0]hexane

The title compound of Preparation D.2. (1.43 g, 5.21 mmol) was treated with hydrochloric acid (7 ml of a 12M solution) and heated to 100° for 18 hours. The reaction was then concentrated in vacuo to provide a viscous oil which was purified by silica gel chromatography (eluant: 189:10:1 then 89:10:1 then 85:14:1 chloroform: methanol: concentrated ammonium hydroxide). In this way the title product was obtained as an oil (661 mg, 3.51 mmol, 67% yield). $^1$H NMR (CDCl$_3$) 7.27 (m, 5H), 3.60 (s, 2H), 3.02 (d, J=8 Hz, 1H), 2.84 (d, J=9 Hz, 1H), 2.50 (dd, J=8, 4 Hz, 1H), 2.33 (d, J=8 Hz, 1H), 1.9 (vbs, 2H), 1.18 (m, 1H), 1.09 (m, 1H), 0.63 (dd, J=8, 4 Hz, 1H).

4. 1-Acetylamino-3-benzyl-3-azabicyclo[3.1.0]hexane

Acetyl chloride (0.273 ml, 3.85 mmol) was added dropwise over 5 minutes to a solution of the title compound of Preparation D.3. (144.7 mg, 0.77 mmol), dimethylaminopyridine (47 mg, 0.38 mmol) and triethylamine (1.6 ml, 11.5 mmol) in tetrahydrofuran (10 ml). The reaction was allowed to stir at room temperature for 18 hours; the solvent was then removed in vacuo and the residue diluted with methylene chloride. This organic solution was washed with aqueous sodium bicarbonate followed by saturated aqueous sodium chloride; after drying over magnesium sulfate, the solution was filtered and concentrated in vacuo to provide a dark red oil. Purification by column chromatography (eluant: 189:10:1 chloroform: methanol: concentrated ammonium hydroxide) provided the title product as a yellow oil (89.5 mg, 0.39 mmol, 51% yield). $^1$H NMR (CDCl$_3$) 7.25 (m, 5H), 5.96 (bs, 1H), 3.60 (m, 2H), 3.07 (d, J=8 Hz, 1H), 2.87 (d, J=9 Hz, 1H), 2.63 (dd, J=9, 4 Hz, 1H)), 2.51 (d, J=8 Hz, 1H), 1.90 (s, 3H), 1.52 (m, 1H), 1.35 (m, 1H), 0.70 (dd, J=9, 5 Hz, 1H).

5. 1-Acetylamino-3-azabicyclo[3.1.0]hexane

The title compound of Preparation D.4. (77.8 mg, 0.34 mmol) was dissolved in ethanol (20 ml) and treated with palladium on carbon (10%, 105 mg, 0.09 mmol); after addition of ammonium formate (78 mg, 1.24 mmol) the reaction mixture was heated to 60° for 1 hour. The reaction mixture was filtered through diatomaceous earth (Celite (trademark)), the diatomaceous earth washed well with ethanol, and the combined filtrates concentrated in vacuo to provide a yellow-green oil. Purification by silica gel chromatography (eluant: 1:1 chloroform: methanol with 1% ammonium hydroxide) provided the title product as a viscous oil (26.1 mg, 0.186 mmol, 55% yield). $^1$H NMR (CD$_3$OD): 3.10 (m, 2H), 2.87 (d, J=11 Hz, 1H), 2.84 (d, J=11 Hz, 1H), 1.90 (s, 3H), 1.55 (m, 1H), 0.88 (d, J=7 Hz, 2H).

PREPARATION E

1. 5-Benzyl-1,3a,4,5,6,6a-hexahydro-4,6-dioxopyrrolo[3,4-c]pyrazole-3-carboxylic acid, ethyl ester Ethyl diazoacetate (13 g, 114 mmol) in diethyl ether (100 ml) was added dropwise to a solution of N-benzylmaleimide (10 g, 53 mmol) in diethyl ether (250 ml). The resulting mixture was allowed to stir for 18 hours; the solvent was then removed in vacuo, and the resulting residue partitioned between methylene chloride and water. The organic layer was dried over sodium sulfate, filtered and concentrated to provide the title product as a white solid, mp 145°-146° with decomposition (16 g, 53 mmol, 100% yield). $^1$H NMR (CDCl$_3$): 7.31 (m, 5H), 7.02 (bs, 1H), 4.89 (dd, J=11, 2 Hz, 1H), 4.65 (s, 2H), 4.55 (d, J=10 Hz, 1H), 4.36 (q, J=7 Hz, 2H), 1.37 (t, J=7 Hz, 3H).

2. [1α,5α,6α]-3-Benzyl-3-azabicyclo[3.1.0]hexane-2,4-dione-6-carboxylic acid, ethyl ester The title compound of Preparation E.1. (99 g, 0.33 mol) was thermolyzed in a 185° oilbath; after 1.5 hours, the reaction was cooled to room temperature and the product recrystallized from diethyl ether to provide the title product as a white solid, mp 100°-101° (31.2 g, 114 mol, 35% yield). $^1$H NMR (CDCl$_3$): 7.29 (s, 5H), 4.50 (s, 2H), 4.17 (q, J=7 Hz, 2H), 2.86 (d, J=3 Hz, 2H), 2.28 (t, J=3 Hz, 1H), 1.26 (t, J=7 Hz, 3H).

3. [1α,5α,6α]-3-Benzyl-6-hydroxymethyl-3-azabicyclo[3.1.0]hexane

A solution of ethyl 3-benzyl-3-azabicyclo[3.1.0]hexane-2,4-dione-6-carboxylate (2.73 g, 10 mmol) was added to a suspension of lithium aluminum hydride (1.5 g, 40 mmol) in tetrahydrofuran (250 ml). The resulting mixture was heated to reflux for 28 hours. The reaction mixture was quenched with saturated aqueous ammonium chloride (2 ml) and filtered; the filtrate was concentrated in vacuo to provide the title product as a colorless oil (1.69 g, 8.3 mmol, 83% yield). $^1$H NMR (CDCl$_3$) 7.27 (m, 5H), 3.58 (s, 2H), 3.43 (d, J=7 Hz, 2H), 2.96 (d, J=8 Hz, 2H), 2.35 (bd, J=9 Hz, 2H), 1.58 (m, 1H), 1.28 (s, 2H).

4. [1α,5α,6α]-3-Benzyl-3-azabicyclo[3.1.0]hexane-6-carboxaldehyde

Dimethylsulfoxide (0.48 ml, 6.8 mmol) was added to a −65° solution of oxalyl chloride (0.33 ml, 3.8 mmol) in methylene chloride (80 ml). A solution of the title compound of Preparation E.3. (0.75 g, 3.7 mmol) in methylene chloride (20 ml) was then added to the reaction mixture, still at −65°. After addition of triethylamine (2.0 ml, 16 mmol), the mixture was allowed to warm to room temperature. The solvent was then removed in vacuo, and the residue was partitioned between water and diethyl ether. The combined organic layers were dried over sodium sulfate, filtered and concentrated to provide a light brown oil. Column chromatography (eluant: 20% ethyl acetate in hexanes) provided the title product as a light green oil (574 mg, 285 mmol, 77% yield). $^1$H NMR (CDCl$_3$): 9.26 (d, J=5 Hz, 1H), 7.24 (m, 5H), 3.59 (s, 2H), 3.03 (d, J=9 Hz, 2H), 2.45 (bd, J=9 Hz, 2H), 2.40 (m, 1H), 2.06 (bs, 2H).

5.
[1α,5α,6α]-3-Benzyl-3-azabicyclo[3.1.0]hexane-6-carboxaldehyde oxime

A solution of the title compound of Preparation E.4. (3.2 g, 16 mmol) in ethanol (160 ml) was treated with sodium acetate (4.25 g, 60 mmol) and hydroxylamine hydrochloride (3.2 g, 46 mmol) and allowed to stir for 18 hours. After removal of solvent in vacuo, the residue was partitioned between methylene chloride and aqueous potassium carbonate. The combined organic layers were dried over sodium sulfate and concentrated to provide the title product (3.29 g, 15.2 mmol, 95% yield). $^1$H NMR (CDCl$_3$, mixture of geometrical isomers around oxime): 7.28 (m, 5H), 7.07 and 6.06 (d, J=8, 9 Hz, 1H), 3.61 and 3.60 (s, 2H), 3.07 and 3.04 (d, J=9 Hz, 2H), 2.75 and 2.10 (m, 1H), 2.41 (m, 2H), 1.64 (m, 2H).

6.
[1α,5α,6α]-6-Aminomethyl-3-benzyl-3-azabicyclo[3.1.0]hexane

The title compound of Preparation E.5. (3.2 g, 14 mmol) was dissolved in tetrahydrofuran (150 ml) and treated with lithium aluminum hydride (1.85 g, 49 mmol). The resulting suspension was heated to reflux for 12 hours. Water (5 ml) and a saturated solution of sodium potassium tartrate (2 ml) were added; the mixture was allowed to stir for 1 hour. Magnesium sulfate was added, and the mixture was filtered; removal of solvent from the filtrate provided the title product as a yellow oil (2.3 g, 11 mmol, 78% yield). $^1$H NMR (CDCl$_3$) 7.27 (m, 5H), 3.58 (s, 2H), 2.96 (d, J=9 Hz, 2H), 2.50 (d, J=7 Hz, 2H), 2.34 (d, J=9 Hz, 2H), 1.38 (m, 1H), 1.32 (bs, 2H), 1.19 (bs, 2H).

7.
[1α,5α,6α]-3-Benzyl-6-[tert-butoxycarbonyl)aminomethyl]-3-azabicyclo[3.1.0]hexane The title compound of Preparation E.6. (150 mg, 0.74 mmol) was dissolved in dioxane (9 ml) and water (1 ml) and treated with triethylamine (0.15 ml, 1.1 mmol) and di-tert-butyl dicarbonate (165 mg, 0.76 mmol). The resulting solution was allowed to stir for 1.5 hours, and was then partitioned between diethyl ether and water. The combined organic layers were dried over sodium sulfate, filtered and concentrated in vacuo to provide the title product as a pale green oil (216 mg, 0.71 mmol, 96% yield). $^1$H NMR (CDCl$_3$) 7.27 (m, 5H), 4.73 (bs, 1H), 3.57 (s, 2H), 2.97 (m, 4H), 2.34 (bd, J=9 Hz, 2H), 1.44 (m, 10H), 1.25 (bs, 2H).

8.
[1α,5α,6α]-6-(tert-Butoxycarbonyl)aminomethyl-3-azabicyclo[3.1.0]hexane A mixture of the title compound of Preparation E.7. (240 mg, 0.79 mmol), 10% palladium on carbon (240 mg) and ammonium formate (240 mg, 3.8 mmol) in ethanol (10 ml) was stirred at room temperature for 0.5 hour. The mixture was filtered and concentrated to give a gummy solid which was mixed with methylene chloride and filtered. Removal of solvents under reduced pressure gave a yellow oil which was crystallized from ethyl ether to give the title product as a white solid, mp 95°–97° (148 mg, 0.70 mmol, 89% yield). $^1$H NMR (CDCl$_3$) 8.47 (bs, 1H), 4.80 (bs, 1H), 3.33 (m, 4H), 3.06 (m, 2H), 1.66 (bs, 2H), 1.43 (s, 9H), 1.23 (bs, 1H).

EXAMPLE F

1.
[1α,5α,6α]-6-Hydroxymethyl-3-azabicyclo[3.1.0]-hexane

[1α,5α,6α]-3-Benzyl-6-hydroxymethyl-3-azabicyclo[3.1.0]hexane (2.5 g, 12 mmol) was dissolved in methanol (200 ml), treated with palladium hydroxide on carbon (20% palladium content, 500 mg) and stirred under 1 atmosphere of hydrogen for 4.5 hours. The reaction mixture was filtered, and concentrated in vacuo; the residue was mixed with acetonitrile and allowed to crystallize. Filtration provided the title product as an amorphous white solid, mp 98°–100° (1.16 g, 10.2 mmol, 85% yield). $^1$H NMR (CDCl$_3$): 3.49 (d, J=7 Hz, 2H), 2.98 (d, J=11 Hz, 2H), 2.85 (bd, J=12 Hz, 2H), 1.67 (bs, 2H), 1.33 (m, 2H), 0.89 (m, 1H).

2.
[1α,5α,6α]-3-Benzyloxycarbonyl-6-hydroxymethyl-3-azabicyclo[3.1.0]hexane The title compound of Preparation F.1 (1.0 g, 8.8 mmol) was dissolved in dioxane (40 ml) and water (40 ml) and treated with sodium bicarbonate (3 g, 36 mmol) and benzyl chloroformate (1.3 ml, 9.1 mmol). After 30 minutes, the reaction mixture was extracted with ethyl acetate; the combined organic layers were dried over sodium sulfate, filtered and concentrated to provide the title product as an oil (2.15 g., 8.7 mmol, 99% yield). $^1$H NMR (CDCl$_3$): 7.32 (bs, 5H), 5.08 (s, 2H), 3.65 (m, 2H), 3.46 (m, 4H), 1.45 (m, 2H), 0.91 (m, 1H).

3.
[1α,5α,6α]-3-Benzyloxycarbonyl-3-azabicyclo[3.1.0]hexane-6-carboxylic acid A solution of the title compound of Preparation F.2 (2.1 g, 8.5 mmol) in acetone (50 ml) was treated dropwise with Jones' reagent until an orange color persisted. Isopropanol was then added to quench excess oxidant, and the resulting mixture was partitioned between water and methylene chloride. The organic layer was dried over sodium sulfate, filtered and concentrated to provide the title product as an oil (2.08 g, 8.0 mmol, 94% yield). $^1$H NMR (CDCl$_3$) 7.32 (bs, 5H), 5.08 (s, 2H), 3.72 (m, 2H), 3.50 (bs, 2H), 2.13 (bs, 2H), 1.47 (t, J=3 Hz, 1H).

4. [1α,5α,6α]-3-Benzyloxycarbonyl-6-tert-butoxycarbonylamino-3-azabicyclo[3.1.0]hexane Diphenylphosphoryl azide (865 l, 4 mmol), triethylamine (1.1 ml, 8 mmol) and the title compound of Preparation F.3. (1.0 g, 3.83 mmol) were dissolved in t-butanol (45 ml) and heated to reflux for 18 hours. The solvent was then removed in vacuo, and the residue partitioned between water and ethyl acetate. The combined organic layers were dried over sodium sulfate and concentrated to provide a residue which was purified by column chromatography (eluant: 40% ethyl acetate in hexane). The title product was obtained as an oil (772 mg, 2.3 mmol, 60% yield). $^1$H NMR (CDCl$_3$): 7.31 (s, 5H), 5.06 (s, 2H), 4.65 (bs, 1H), 3.70 (m, 2H), 3.46 (m, 2H)/ 2.26 (bs, 1H), 1.67 (bs, 2H), 1.41 (s, 9H).

5. [1α,5α,6α]-6-tert-Butoxycarbonylamino-3-azabicyclo 3.1.0]hexane

A solution of the title compound of Preparation F.4. (58 mg, 0.17 mmol) was treated with palladium on carbon (10% by weight, 60 mg) and ammonium formate (60 mg, 1 mmol) and heated to 65° for 15 minutes. The reaction mixture was then filtered through Super-cel and the filtrate concentrated in vacuo to provide the title product as a solid (28 mg, 0.14 mmol, 82% yield). $^1$H NMR (CDCl$_3$) 4.65 (bs, 1H), 3.14 (d, J=12 Hz, 2H), 2.93 (m, 2H), 2.30 (bs, 1H), 1.59 (bs, 2H), 1.44 (s, 9H).

EXAMPLE G

1. [1α,5α,6α]-3-Benzyl-4-hydroxy-4-methyl-3-azabicyclo-[3.1.0]hexan-2-one-6-carboxylic acid, ethyl ester

[1α,5α,6α]-3-Benzyl-3-azabicyclo[3.1.0]hexane-2,4-dione -6-carboxylic acid, ethyl ester (26 g, 95 mmol) was dissolved in tetrahydrofuran (800 ml) and cooled to −78°. Methyllithium (105 mL of a 0.98M solution in ether, 102 mmol) was added dropwise. Saturated aqueous ammonium chloride was added to the cold reaction mixture; the mixture was then extracted with ethyl acetate. The combined organic layers were dried over sodium sulfate, treated with decolorizing charcoal, filtered and concentrated in vacuo to provide the title product as a brown oil (26.86 g, 93 mmol, 98% yield). This was used without purification. $^1$H NMR (CDCl$_3$) 7.27 (m, 5H), 4.63 (bd, J=16 Hz, 1H), 4.17 (m, 3H), 2.54 (d, J=3 Hz, 2H), 1.75 (t, J=3 Hz, 1H), 1.63 (s, 1H), 1.34 (s, 3H), 1.28 (t, J=7 Hz, 3H).

2. [1α,2α,5α,6α]-3-Benzyl-6-hydroxymethyl-2-methyl-3-azabicyclo[3.1.0]hexane The compound of Example G.1 (28 g, 95 mmol) was dissolved in tetrahydrofuran (800 ml), treated with lithium aluminum hydride (18 g, 470 mmol) and heated to reflux for 18 hours. The reaction mixture was then treated with saturated ammonium chloride (30 ml), water (90 mL), and allowed to be stirred until a white precipitate formed. The solid was filtered off, and the filtrate concentrated in vacuo to provide an oil. This was purified by column chromatography (eluant: 20% ethyl acetate in hexanes, then 40%, then ethyl acetate) to provide the title product as an oil (10.86 g, 50 mmol, 53% yield). $^1$H NMR (CDCl$_3$): 7.23 (m, 5H), 3.88 (d, J=13.5 Hz, 1H), 3.38 (m, 2H), 3.13 (d, J=13.5 Hz, 1H), 2.90 (d, J=9 Hz, 1H), 2.69 (m, 1H), 2.30 (dd, J=9, 3 Hz, 1H), 1.76 (bs, 1H), 1.50 (m, 1H), 1.27 (m, 1H), 1.18 (m, 1H), 1.14 (d, J=6 Hz, 3H).

3. [1α,2β,5α,6α]-3-Benzyl-2-methyl-3-azabicyclo-[3.1.0]-hexane-6-carboxaldehyde Dimethylsulfoxide (0.6 ml, 7.8 mmol) was added to a −65° solution of oxalyl chloride (0.67 ml, 7.7 mmol) in methylene chloride (200 ml). A solution of the compound of Example G.2 (1.5 g, 7 mmol) in methylene chloride (50 ml) was then added to the reaction mixture, still at −65°. After addition of triethylamine (4.3 ml, 30 mmol), the mixture was allowed to warm to room temperature. Hydrochloric acid (3N, 150 ml) was added; the organic layer was then washed with additional hydrochloric acid (3N, 100 ml). The aqueous layer was basified with potassium carbonate, and extracted with ether. The combined ether layers were washed with brine, dried over sodium sulfate and concentrated in vacuo to provide a residue, which was mixed with hexane, filtered and concentrated to provide the crude title product as an oil (1.26 g, 5.8 mmol, 83% yield). $^1$H NMR (CDCl$_3$): 9.23 (d, J=5 Hz, 1H), 7.26 (m, 5H), 3.91 (d, J=13.5 Hz, 1H), 3.15 (d, J=13.5 Hz, 1H), 2.95 (d, J=9 Hz, 1H), 2.85 (m, 1H), 2.42 (dd, J=9.6, 3.3 Hz, 1H), 2.34 (m, 1H), 2.10 (m, 1H), 2.00 (m, 1H), 1.16 (d, J=6 Hz, 3H).

4. [1α,2β,5α,6α]-3-Benzyl-2-methyl-3-azabicyclo-[3.1.0]hexane -6-carboxaldehyde oxime A solution of the compound of Example G.3 (1.0 g, 4.6 mmol) in ethanol (50 ml) was treated with sodium acetate (1.5 g, 18 mmol) and hydroxylamine hydrochloride (0.915 g, 13 mmol) and allowed to be stirred for 1 hour. After removal of solvent in vacuo, the residue was partitioned between chloroform and aqueous potassium carbonate. The combined organic layers were dried over sodium sulfate and concentrated. The solid material thus obtained was recrystallized from hexane to provide the title product as white needles, mp 104°-107° C. (729 mg, 3.16 mmol, 69% yield).

5. [1α,2β,5α,6α]-6-aminomethyl-3-benzyl-2-methyl-3-azabicyclo[3.1.0]hexane

The compound of Example G.4 (4.2 g, 18 mmol) was dissolved in tetrahydrofuran (250 ml) and treated with lithium aluminum hydride (4.2 g, 111 mmol). The resulting suspension was heated to reflux for 1 hour. Saturated aqueous sodium chloride (24 ml) and water (5 ml) were added; the resulting precipitate was filtered off, and the filtrate concentrated to provide the crude product as an oil (3.68 g, 17 mmol, 94% yield). $^1$H NMR (CDCl$_3$) 7.23 (m, 5H), 3.87 (d, J=13.5Hz, 1H), 3.11 (d, J=13.5 Hz, 1H), 2.88 (d, J=9.0 Hz, 1H), 2.66 (m, 1H), 2.45 (m, 2H), 2.28 (dd, J=9 4 Hz, $^1$H), 1.54 bs, 2H), 1.30 (m, 1H), 1.18 (m, 1H), 1.12 id, J=5.9 Hz, 3H), 1.09 (m, 1H).

6. [1α,2β,5α,6α]-6-(tert-Butoxycarbonyl)aminomethyl-2-methyl-3-azabicyclo[3.1.0]hexane The compound of Example G.5 (3.4 g, 15.7 mmol) was dissolved in dioxane (50 ml) and water (6 ml) and treated with di-tert-butyl dicarbonate (3.4 g, 15.7 mmol). The reaction solution was allowed to stir for 1 hour, and was then concentrated in vacuo. The resulting material was purified by column chromatography (eluant: 20% ethyl acetate in hexane) to provide the title product as a white solid, mp 71°-72° C. mmol, 97% yield).

7. [1α,2β,5α,6α]-6-(tert-Butoxycarbonyl)aminomethyl-2-methyl-3-azabicyclo[3.1.0]hexane A mixture of the compound of Example G.6 (3.4 g, 11 mmol) and 10% palladium hydroxide (3.5 g) in methanol (350 ml) was treated with hydrogen at atmospheric pressure for 18 hours. Filtration and removal of solvent in vacuo provided a crude product which was purified by column chromatography (eluant: 89:10:1 chloroform: methanol: concentrated ammonium hydroxide). Trituration with ether provided the title product as a white solid, mp 89.5°-91.5° C. (1.86 g, 8.2 mmol, 75% yield). $^1$H NMR (CDCl$_3$) 4.82 (bs, 1H), 3.16 (m, 1H), 2.89 (m, 2H), 2.81 (m, 2H), 1.33 (s, 10H), 1.16 (m, 2H), 1.00 (d, J=6.3 Hz, 3H), 0.72 (m, 1H).

EXAMPLE H

1. [1α,2β,5α,6α]-6-Hydroxymethyl-2-methyl-3-azabicyclo[3.1.0]hexane

[1,α2,62 ,5α,6α]-3-Benzyl-6-hydroxymethyl-2-methyl-3-azabicyclo[3.1.0]hexane (4.2 g, 19.3 mmol) was dissolved in methanol (150 mmol), treated with palladium hydroxide on carbon (10% palladium content, 3.0 g) and stirred under 1 atmosphere of hydrogen for 18 hours. The reaction mixture was filtered and concentrated in vacuo to provide the title product as a white solid, mp 85°-87° C. (2.45 g, 19.3 mmol, 100% yield). $^1$H NMR (CDCl$_3$) 3.39 (dd, J=7, 10 Hz, 1H), 3.28 (dd, J=7, 9 Hz, 1H), 3.19 (m, 1H), 2.84 (m, 4H), 1.24 (m, 2H), 1.05 (d, J=6 Hz, 3H), 0.82 (m, 1H).

2. [1α,2β,5α,6α]-3-Benzyloxycarbonyl-6-hydroxymethyl-2-methyl-3azabicyclo[3.1.0]hexane The compound of Example H.1 (2.3 g, 18 mmol) was dissolved in dioxane (50 ml) and water (50 ml) and treated with saturated aqueous bicarbonate solution (50 ml) and benzyl chloroformate (2.8 ml, 19 mmol). After 18 hours, the reaction mixture was partitioned between ether and water; the combined organic layers were dried over sodium sulfate, filtered and concentrated in vacuo. The residue was purified by column chromatography (eluant: 50% ethyl acetate in hexane) to provide the title product as an oil (3.68 g, 14 mmol, 78% yield). $^1$H NMR (CDCl$_3$): 7.30 (m, 5H), 5.18 (AB quartet, J=12.5 Hz, 2H), 3.98 (m, 1H), 3.54 (d, J=2 Hz, 2H), 3.43 (m, 2H), 2.31 (s, 1H), 1.55 (m, 1H), 1.40 (m, 1H), 1.32 (d, J=6 Hz, 3H), 1.02 (m, 1H).

3. [1α,2β,5α,6α]-3-Benzyloxycarbonyl-2-methyl-3-azabicyclo[3.1.0]hexane-6-carboxylic acid A solution of the compound of Example H.2 (3.2 g, 12 mmol) in acetone (100 ml) was treated dropwise with Jones' reagent until an orange color persisted. Isopropanol was then added to quench excess oxidant, and the resulting mixture was partitioned between water and methylene chloride. The organic layer was dried over sodium sulfate, filtered and concentrated to provide a residue, which was mixed with ether, dried once more over sodium sulfate, filtered and concentrated in vacuo to provide the title product as a gum (3.06 g, 11.1 mmol, 93% yield). $^1$H NMR (CDCl$_3$): 10.2 (vbs, 1H), 7.33 (m, 5H), 5.09 (m, 2H), 4.08 (m, 1H), 3.64 (bs, 2H), 2.27 (m, 1H), 2.09 (m, 1H), 1 59 (t, J=3 Hz, 1H), 1.38 (bs, 3H).

4. [1α,2β,5α,6α]-3-Benzyloxycarbonyl-6-tert-butoxycarbonylamino-2-methyl-3-azabicyclo[3.1.0]hexane Diphenylphosphoryl azide (2.3 ml, 10.6 mmol), triethylamine (2.85 ml, 20 mmol) and the compound of Example H.3, (2.85 g, 10 mmol) were dissolved in t-butanol (120 ml) and heated to reflux for 18 hours. The solvent was then removed in vacuo, and the residue purified by column chromatography (eluant: 20% ethyl acetate in hexane). The title product was obtained as a solid, mp 118°-120° C. 11.7 g, 4.9 mmol, 49% yield).

5. [1α,2β,5α,6α]-6-tert-Butoxycarbonylamino-2-methyl-3-azabicyclo[3.1.0]hexane A solution of the compound of Example H.4 (1.5 g, 4.3 mmol) in methanol (150 ml) was treated with palladium hydroxide on carbon (10% palladium content, 1.5 g) and stirred under one atmosphere of hydrogen for 2.5 hours. The catalyst was removed by filtration and the filtrate concentrated in vacuo to provide a residue, which was purified by column chromatography (eluant: 89:10:1 chloroform:methanol:concentrated ammonium hydroxide) to provide the title product as a gum (771 mg, 3.6 mmol, 84% yield). $^1$H NMR (CDCl$_3$) 9.15 (vbs, 1H), 4.72 (s, 1H), 3.94 (m, 1H), 3.56 (bd, J=11 Hz, 1H), 3.35 (m, 1H), 2.88 (s, 1H), 1.86 (m, 1H), 1.81 (m, 1H), 1.58 (d, J=6.2 Hz, 3H), 1.40 (s, 9H).

EXAMPLE I

1. N-Benzyl-N-(1-cyanoprop-2-yl)-3-amino-1,2-propanediol

A solution of glycidol (70 ml, 1.05 mol) and 3-(benzylamino)butyronitrile (111 g, 0.64 mol) in ethanol (800 ml) was heated to reflux for 18 hours. Additional glycidol (50 ml, 0.75 mol) was added, and the mixture was heated at reflux for an additional 24 hours. Removal of solvent in vacuo left a residue which was partitioned between water and ethyl acetate. The organic layer was washed with water, washed with saturated sodium chloride solution and dried over sodium sulfate. Filtration and concentration in vacuo provided an oil, which was purified by column chromatography (eluant: 5% methanol in chloroform) to give the title product as an oil (42 g, 0.17 mol, 27% yield). $^1$H NMR (CDCl$_3$) 7.31 (m, 5H), 3.77 (d, J=13.4 Hz, 1H), 3.67 (m, 3H), 3.49 (d, J=13.5 Hz, 1H), 3.43 (m, 1H), 3.18 (m, 1H), 2.55 (m, 4H), 2.30 (m, 1H), 1.16 and 1.08 (d, J=6.5 Hz, 3H).

2. [1α,2β,5α]-3-Benzyl-1-cyano-2-methyl-3-azabicyclo[3.1.0]hexane -[1α,2α,5α]-3-Benzyl-1-cyano-2-methyl-3-azabicyclo[3.1.0]hexane A solution of the compound of Example I.1 (7.5 g, 30 mmol) and triethylamine (10.6 ml, 76 mmol) in chloroform (300 ml) was treated with methanesulfonyl chloride (5.2 ml, 67 mmol). After 1 hour, the reaction mixture was partitioned between chloroform and saturated sodium bicarbonate. The organic layer was washed with water, dried over sodium sulfate, filtered and concentrated in vacuo to provide the crude bis-mesylate derivative. This was dissolved in tetrahydrofuran (50 ml) and added dropwise to a solution of sodium hexamethyldisilazide (62 ml of a 1N solution in tetrahydrofuran, 62 mmol) in tetrahydrofuran (300 ml). After 1 hour, the reaction mixture was poured into saturated ammonium chloride solution (500 ml) and ether (300 ml). The aqueous layer was extracted with additional ether, and the combined organic layers were washed with saturated sodium chloride solution, dried over sodium sulfate, filtered and concentrated in vacuo. The resulting brown oil was purified by column chromatography (eluant: 20% ethyl acetate in hexanes) to provide [1α,2β,5α]-3benzyl-1-cyano-2-methyl-3-azabicyclo[3.1.0]hexane (0.97 g, 4.6 mmol, 15% yield) and [1,2,5]-3-benzyl-1-cyano-2-methyl-3-azabicyclo[3.1.0]hexane (0.84 g, 4.00 mmol, 13% yield).

1H NMR (CDCl3) for [1α,2β,5α] isomer: 7.24 (m, 5H), 3.88 (d, J=13.6 Hz, 1H), 3.19 (d, J=13.5, Hz, 1H), 2.88 (q, J=6 Hz, 1H), 2.85 (d, J=9.6 Hz, 1H), 2.42 (dd, J=9.2, 3.7 Hz, 1H), 1.95 (m, 1H), 1.48 (appparent t, J=4.9, 4.6 Hz, 1H), 1.25 (d, J=5.9 Hz, 3H), 0.97 (dd, J=8.2, 5.1 Hz, 1H).

1H NMR (CDCl3) for [1α,2α,5α] isomer: 7.24 (m, 5H), 3.69 (d, J=13.5 Hz, 1H), 3.57 (d, J=13.5 Hz, 1H), 3.31 (q, J=6.6 Hz, 1H), 2.73 (m, 2H), 2.03 (m, 1H), 1.60 (apparent t, J=5.0, 4.5 Hz, 1H), 1.14 (d, J=6.7 Hz, 3H), 1.13 (m, 1H).

3.

[1α,2β,5α]-1-Aminomethyl-3-benzyl-2-methyl-3-azabicyclo[3.1.0]hexane

Lithium aluminum hydride (4.3 ml of a 1M solution in tetrahydrofuran, 4.3 mmol) was added to a solution of [1α,2β,5α]-3benzyl-1-cyano-2-methyl-3-azabicyclo-[3.1.0]-hexane (224 mg, 1.05 mmol) in tetrahydrofuran (10 ml). After 18 hours at room temperature, the reaction mixture was treated sequentially with water (0.16 ml), sodium hydroxide (0.16 ml of a 15% aqueous solution) and water (0.48 ml). The mixture was filtered, and the filtrate was concentrated in vacuo to provide the title product as a light yellow oil (213.3 mg, 0.99 mmol, 94% yield). 1H NMR (CDCl3): 7.24 (m, 5H), 3.91 (d, J=13.5 Hz, 1H), 3.16 (d, J=13.6 Hz, 1H), 2.95 (d, J=13.5 Hz, 1H), 2.83 (d, J=8.9 Hz, 1H), 2.68 (q, J=5.9 Hz, 1H), 2.61 (d, J=13.5 Hz, 1H), 2.28 (dd, J=8.9, 3.6 Hz, 1H), 1.19 (bs, 2H), 1.13 (m, 1H), 1.11 (d, J=5.6 Hz, 3H), 0.88 (apparent t, J=4.4, 3.5 Hz, 1H), 0 20 (dd, J=8.0, 4.3 Hz, 1H).

4.

[1α,2β,5α]-3-Benzyl-1-[(N-acetyl)aminomethyl]-2-methyl-3-azabicyclo[3.1.0]hexane A solution of the compound of Example I.3 (213 mg, 0.98 mmol) and triethylamine (0.2 ml, 1.47 mmol) in acetic anhydride (5 ml) was allowed to be stirred at room temperature for 18 hours. The reaction solution was then diluted with chloroform and washed with saturated sodium bicarbonate solution and saturated sodium chloride solution. The organic layer was dried over magnesium sulfate, filtered and concentrated in vacuo to provide a yellow oil, which was purified by column chromatography (eluant: 189:10:1 chloroform: methanol: concentrated ammonium hydroxide) to provide the title product as an oil (168 mg, 0.65 mmol, 66% yield).

1H NMR (CDCl3) 7.26 (m, 5H), 5.46 (bs, 1H), 3.93 (d, J=13 Hz, 1H), 3.54 (dd, J=13, 6Hz, 1H), 3.23 (m, 2H), 2.86 (d, J=9 Hz, 1H), 2.63 (m, 1H), 2.32 (m, 1H), 1.99 (s, 3H), 1.19 (m, 1H), 1.14 (d, J=6Hz, 3H), 0.98 (bs, 1H), 0.28 (dd, J=8, 4Hz, 1H).

5. [1α,2β,5α]-1-[N-Acetyl)aminomethyl]-2-methyl-3-azabicyclo[3.1.0]hexane

The compound of Example I.4 (164 mg, 0.63 mmol) and 10% palladium on carbon (200 mg) were mixed with ethanol (15 ml). The resulting suspension was treated with ammonium formate (119 mg, 1.89 mmol) and heated to 60° C. for 40 minutes. The reaction mixture was filtered through diatomaceous earth (Celite (trademark)), and the solid cake was rinsed thoroughly with ethanol. Removal of solvent in vacuo provided the title product as a viscous oil (101.4 mg, 0.62 mmol, 96% yield).

1H NMR (CDCl3): 5.46 (bs, 1H), 3.50 (dd, J=14.3, 5.7 Hz, 1H), 3.30 (dd, J=14.3, 5.8 Hz, 1H), 3.15 (q, J=6.2 Hz, 1H), 2.93 (dd, J=11.3, 3.1 Hz, 1H), 2.81 (d, J=11.2 Hz, 1H), 1.96 (s, 3H), 1.28 (m, 1H), 1.08 (d, J=6.4 Hz, 3H), 0.42 (m, 2H).

EXAMPLE J

1.

[1α,2β,5α]-3-Benzyl-2-methyl-3-azabicyclo[3.1.0]-hexane-1-carboxylic acid hydrochloride A mixture of [1α,2β,5α]-3-benzyl-1-cyano-2-methyl-3-azabicyclo[3.1.0]hexane (2.25 g, 10.6 mmol) and barium hydroxide octahydrate (5.0 g, 15.8 mmol) in water (100 ml) was heated at reflux for 5 days. The reaction was then acidified with 6N hydrochloric acid, and water was removed in vacuo. Ethanol was added to the residue, the inorganic salts were removed by filtration, and the filtrate was concentrated in vacuo. Trituration with chloroform produced a white solid, which was recrystallized from chloroform to provide the title product, mp 228°-229° C. (2.5 g, 9.3 mmol, 88% yield).

2.

[1α,2β,5α]-3-Benzyl-1-[(N-tert-butoxycarbonyl)amino]-2-methyl-3-azabicyclo[3.1.0]hexane A solution of the compound of Example J.1 (2.5 g, 9.3 mmol) in acetone (15 ml) and water (15 ml) was treated with ethyl choloroformate (0.92 ml, 9.6 mmol) and allowed to be stirred for 30 minutes. Sodium azide (625 mg, 9.6 mmol) was then added. After one hour, the reaction mixture was partitioned between water and ether. The organic layer was dried over sodium sulfate, filtered and concentrated in vacuo; the resulting oil was dissolved in toluene (10 ml) and heated to 100° C. for 1 hour. After addition of tert-butanol (40 ml), the reaction solution was heated to reflux for 18 hours. Removal of solvent in vacuo provided a residue, which was purified by column chromatography (eluant: 20% ethyl acetate in hexane) to provide the title produce as a solid, mp 91°-92° C. (1.46 g, 4.83 mmol, 52% yield).

3.

[1α,2β,5α]-1-[(N-tert-Butoxycarbonyl)amino-2-methyl-3-azabicyclo[3.1.0]hexane

The compound of Example J.2 (380 mg, 1.25 mmol) was dissolved in methanol (50 ml), treated with palladium hydroxide on carbon (10% palladium content, 350 mg) and subjected to hydrogenation (30 psi hydrogen) for 2 hours. The reaction mixture was filtered and concentrated in vacuo to provide a residue, which was purified by column chromatography (eluant: 89:10:1 chloroform: methanol: concentrated ammonium hydroxide) to provide the title product as a white solid, mp 132°-135° C. (136 mg, 0.64 mmol, 51% yield).

$^1$H NMR (CDCl$_3$) 5.35 and 5.19 (bs, 1H), 3.17 (m, 1H), 3.05 (m, 1H), 2.65 (d, J=11.6 Hz, 1H), 1.43 (m, 1H), 1.30 (s, 9H), 0.97 (d, J=6.3 Hz, 3H), 0.63 (m, 2H).

EXAMPLE K

1. [1α,2α,5α]-3-Benzyl-2-methyl-3-azabicyclo[3.1.0]hexane-1-carboxylic acid hydrochloride

[1α,2α,5α]-3-Benzyl-1-cyano-2-methyl-3-azabicyclo [3.1.0]hexane(1.4 g, 6.6 mmol) was mixed whth hydrochloric acid (12 N, 50 ml) and heated to reflux for 18 hours. Removal of solvents in vacuo provided a residue, which was purified by column chromatography (eluant: 89:10:1 chloroform: methanol: concentrated ammonium hydroxide), giving the title product as a gummy solid (1.1 g, 4.8 mmol, 73% yield). An analytical sample was prepared by recrystallization from acetone, mp 157°-158 ° C.

$^1$H NMR (CDCl$_3$) 7.28 (m, 5H), 3.75 (d, J=13.6 Hz, 1H), 3.59 (d, J=13.6 Hz, 1H), 3.39(q, J=6.3 Hz, 1H), 2.76(d, J=8.8 Hz, 1H), 2.67 (dd, J=8.8, 3.2 Hz, 1H), 2.08 (m, 1H), 1.73(m, 1H), 1.18(m, 1H), 1.15(d, J=6.3 Hz, 3H).

2.
[1α,2α,5α]-3-Benzyl-1-[(N-tert-butoxycarbonyl)amino]-2-methyl-3-azabicyclo]3.1.0]hexane The title compound was synthesized from the compound in step 1 according to the procedure of Example H.4. The product was obtained in 43% yield. An analytical sample was prepared by recrystallization from hexane, to give a solid, mp 141°-142 ° C.

$^1$H NMR (CDCl$_3$):7.26 (m, 5H), 5.03 (bs, 1H), 3.64 (AB quartet, J=13.7 Hz, 2H), 3.33 (bm, 1H), 2.77 (bm, 1H), 2.60 (d, J=8.8 Hz, 1H), 1.48 (m, 2H), 1.42 (s, 9H), 0.97 (d, J=6.5 Hz, 3H), 0.85 (m, 1H).

3.
[1α,2α,5α]-1-[(N-tert-Butoxycarbonyl)amino]-2-methyl-3-azabicyclo[3.1.0]hexane The title compound was prepared from the compound of step 2 according to the procedure of Example H.5, except that the hydrogenolysis was carried out at 30 psi. The product was obtained in 85% yield. An analytical sample was prepared by a second chromatographic purification (eluant: 89:10:1 chloroform: methanol: concentrated ammonium hydroxide), followed by recrystallization from ether, to give a white solid, mp 93°-95 ° C.

$^1$H NMR (CDCl$_3$) 5.01 (bs, 1H), 3.41 (m, 1H), 3.15 (dd, J=11.5, 3.2 Hz, 1H), 2.69 (d, J=11.5 Hz, 1H), 1.54 (m, 1H), 1.43 (s, 9H), 1.08 (d, J=6.7 Hz, 3H), 0.90 (m, 2H).

EXAMPLE L

1.
[1α,5α,6α]-3-Benzyloxycarbonyl-3-azabicyclo[3.1.0]hexane-6-carboxylic acid, ethyl ester and

[1α,5α,6β]-3-Benzyloxycarbonyl-3-azabicyclo[3.1.0]hexane-6-carboxylic acid, ethyl ester A solution of ethyl diazoacetate (5.8 ml, 55 mmol) in methylene chloride (32 ml) was added slowly (over 70 hours, using a syringe pump) to a mixture of 1-benzyloxycarbonyl-3-pyrroline (9.25 g, 50.0 mmol), and rhodium acetate (1.0 g, 2.3 mmol) in methylene chloride (140 ml). At the end of the addition, the reaction mixture was filtered through Celite and concentrated in vacuo. The residue was purified by column chromatography (eluant: 10% ethyl acetate in hexane) to provide recovered starting material (3.2 g, 17.3 mmol) and the title products [1α,5α,6α]-3-Benzyloxycarbonyl-3-azabicyclo[3.1.0]hexane-6-carboxylic acid, ethyl ester: (2.61 g, 9.02 mmol, 28% yield based on recovered starting material): $^1$H NMR (CDCl$_3$) 7.32 (m, 5H), 5.08 (s, 2H), 4.10 (q, J=7.4 Hz, 2H), 3.71 (dd, J=14, 11.4 Hz, 2H), 3.49 (m, 2H), 2.07 (m, 2H), 1.46 (m, 1H), 1.23 (t, J=7.4 Hz, 3H).

[1α,5α,6β]-3-Benzyloxycarbonyl-3-azabicyclo[3.1.0]hexane -6-carboxylic acid, ethyl ester: (5.4 g, 18.7 mmol, 57% yield based on recovered starting material):

$^1$H NMR (CDCl$_3$) 7.30 (m, 5H), 5.06 (s, 2H), 3.97 (q, J=7 Hz, 2H), 3.80 (d, J=11.2 Hz, 2H), 3.49 (m, 2H), 1.87 (m, 2H), 1.75 (m, 1H), 1.12 (t, J=7 Hz, 3H).

2.
[1α,5α,6β]-3-Benzyloxycarbonyl-3-azabicyclo[3.1.0]hexane-6-carboxylic acid

A solution of [1α,5α,6β]-3-benzyloxycarbonyl-3-azabicyclo[3.1.0]hexane-6-carboxylic acid, ethyl ester (2.0 g, 6.9 mmol) in methanol (200 ml) was treated with aqueous sodium hydroxide solution (15% by weight, 200 ml). After 2 hours at room temperature, the reaction mixture was concentrated in vacuo, extracted with methylene chloride, then acidified to pH 2 with 6N hydrochloric acid. The organic extracts were discarded, and the aqueous layer was extracted with methylene chloride. The combined organic layers were dried over sodium sulfate, filtered and concentrated to provide the title product as a solid, mp 101°-102° (1.36 g, 5.2 mmol, 75% yield).

$^1$H NMR (CDCl$_3$): 7.33 (m, 5H), 5.10 (d, J=5.3 Hz, 2H), 3.87 (d, J=11.4 Hz, 2H), 3.61 (bd, J=11.1 Hz, 2H), 2.03 (m, 2H), 1.83 (m, 1H).

3.
[1α,5α,6β]-3-Benzyloxycarbonyl-6-tert-butoxycarbonylamino-3-azabicyclo[3.1.0]hexane The title product was prepared from the compound of step 2 by the procedure described in Example H.4, except that the reaction was allowed to proceed for 48 hours, and the column chromatography was carried out using 40% ethyl acetate in hexane. The title product was obtained in 60% yield; an analytical sample was prepared by recrystallization from hexane-ether, to provide a solid of mp 99°-103° C.

$^1$H NMR (CDCl$_3$): 7.31 (m, 5H), 5.09 (s, 2H), 4.40 (bs, 1H), 3.63 (m, 2H), 3.47 (m, 2H), 2.80 (m, 1H), 1.77 (m, 2H), 1.39 (s, 9H).

4.
[1α,5α,6β]-6-tert-Butoxycarbonylamino-3-azabicyclo[3.1.0]hexane

A solution of the compound of step 3 (1.25 g, 3.75 mmol) in ethanol (50 ml) was treated with palladium on carbon (200 mg) and subjected to Parr hydrogenation conditions (30 psi hydrogen) for 2.5 hours. The catalyst was removed by filtration, and the filtrate concentrated in vacuo to provide a residue, which was chromatographed (eluant: 89:10:1 chloroform:methanol:concentrated ammonium hydroxide) to give the title product (682 mg, 3.44 mmol, 91% yield). An analytical sample was prepared by recrystallization from hexane, to provide a white solid, mp 85°-86° C.

¹H NMR (CDCl₃-MeOH-d₄) 3.55 (bd, J=11.7 Hz, 2H), 3.32 (d, J=12.3 Hz, 2H), 2.68 (t, J=6.8 Hz, 1H), 1.99 (m, 2H), 1.42 (s, 9H).

EXAMPLE M

1.

]1α,5α,6α]-3-Benzylcarbonyl-6-(N-methyl)tert-butoxycarbonylamino-3-azabicyclo[3.1.0]hexane A solution of [1,5,6]-3-benzyloxycarbonyl-6-tert-butoxycarbonylamino-3-azabicyclo[3.1.0]hexane (1.25 g, 3.75 mmol) and methyl iodide (1.9 ml, 30.5 mmol) in tetrahydrofuran (10 ml) was treated portionwise with sodium hydride (60% in oil, 500 mg, 7.5 mmol). The resulting mixture was allowed to stir at room temperature for 2.5 hours, and was then poured into saturated aqueous ammonium chloride solution. This mixture was extracted with ethyl acetate, and the combined organic layers were dried over sodium sulfate, filtered and concentrated in vacuo. The resulting material was purified by column chromatography (eluant: 20% ethyl acetate in hexane) to provide the title product as an oil (1.12 g, 3.23 mmol, 86% yield).

¹H NMR (CDCl): 7.32 (m, 5H), 5.08 (s, 2H), 3.68 (m, 2H), 3.46 (m, 2H), 2.80 (s, 3H), 2.20 (bs, 1H), 1.76 (bs, 2H), 1.43 (s, 9H).

2.

[1α,5α,6α]-6-(N-Methyl)tert-butoxycarbonylamino-3-azabicyclo[3.1.0]hexane

A solution of the compound of step 1 (1.3 g, 3.75 mmol) in methanol (50 ml) was treated with palladium hydroxide on carbon (500 mg) and subjected to Parr hydrogenation conditions (30 psi hydrogen, room temperature). After 2 hours, the catalyst was filtered off, and the filtrate was concentrated in vacuo. The title product was obtained as an off-white solid (773 mg, 3.64 mmol, 97% yield). An analytical sample was prepared by trituration with ether, to provide a solid, mp 159°–162° C.

¹H NMR (CDCl₃): 6.50 (vbs, 1H), 3.45 (d, J=11.9 Hz, 2H), 3.35 (d, J=11.5 Hz, 2H), 2.77 (s, 3H), 2.62 (bs, 1H), 1.92 (bs, 2H), 1.42 (s, 9H).

EXAMPLE N

1.

1-Benzyloxycarbonyl-1,2,5,6-tetrahydro-3-pyridinecarboxylic acid, methyl ester

A solution of 1,2,5,6-tetrahydro-3-pyridinecarboxylic acid, hydrochloride salt (1.8 g, 10 mmol) in methylene chloride (60 ml) was cooled to 0° C. Benzyl chloroformate (2.74 ml, 19.2 mmol) was added, followed by addition of triethylamine (7.2 ml, 51.2 mmol), and stirring at room temperature for 12 hours. The reaction mixture was washed with brine and dried over magnesium sulfate. Evaporation in vacuo afforded a yellow oil. This was purified by chromatography on silica gel (eluant: 20%, then 30% ethyl acetate/hexane) to give the product as a slightly yellow oil (2.14 g, 7.7 mmol, 77% yield).

¹H NMR (CDCl₃): 7.35-7.33 (m, 5H), 7.05 (m, 1H), 5.14 (s, 2H), 4.18 (d, J=2.3 Hz, 2H), 3.73 (s, 3H), 3.53 (t, J=5.5 Hz, 2H), 2.30 (m, 2H).

2.

1-Benzyloxycarbonyl-3-hydroxymethyl-1,2,5,6-tetrahydropyridine

To a solution of the compound of step 1 (2.0 g, 7.33 mmol) in tetrahydrofuran (30 ml) at −20° C. was added DIBAL-H. The mixture was warmed up to 0° C. and stirred at this temperature for 5 hours. Addition of methanol (5 ml) at 0° C. followed by addition of a saturated solution of Rochelle salt (10 ml) resulted in the formation of a white slurry. After stirring for an additional 2 hours, this was filtered; the filtrate was extracted with ether and the organic layer was washed with brine and dried over magnesium sulfate. Upon evaporation, the title compound was obtained as a slightly yellow oil (1.14 g, 4.6 mmol, 63% yield).

¹H NMR (CDCl₃) 7.34 (m, 5H), 5.80 (m, 1H), 5.13 (s, 2H), 4.03 (bs, 2H), 3.98 (d, J=2.0 Hz, 2H), 3.53 (t, J=6.0 Hz, 2H), 2.14 (m, 2H).

3.

3-Benzyloxycarbonyl-1-hydroxymethyl-3-azabicyclo[4.1.0]heptane

A flask containing samarium metal (6.54 g, 43.5 mmol) was flame-dried, then charged with tetrahydrofuran (50 ml). A tetrahydrofuran solution (25 ml) of mercuric chloride (1.12 g, 4.14 mmol) was added and the mixture was stirred for ten minutes. After addition of the product of step 2 (2.56 g, 10.4 mmol), the reaction mixture was cooled to −78° C., and chloroiodomethane (3.01 ml, 41.4 mmol) was added dropwise. The mixture was then stirred at room temperature overnight. The reaction mixture was quenched with saturated K₂CO₃ and extracted with ether; the ether layer was washed with brine, dried over MgSO₄ and concentrated to provide a yellow oil. This crude material was chromatographed on silica gel (eluant: 50% ethyl acetate/hexane), providing the title compound as a colorless liquid, (1.62 g, 6.2 mmol, 60% yield).

¹H NMR (CDCl₃): 7.37-7.27 (m, 5H), 5.10 (s, 2H), 3.83 (m, 1H), 3.62 (m, 1H), 3.42 (m, 3H), 3.08 (m, 1H), 1.95 (m, 1H), 1.67 (m, 1H), 0.96 (m, 1H), 0.61 (m, 1H), 0.37 (t, J=5.1 Hz, 1H).

4.

3-Benzloxycarbonyl-3-azabicclo[4.1.0]hexane-1-carboxylic acid

To a solution of the compound of Step 3 (580 mg, 2.22 mmol) in acetone (10 ml) was added Jones reagent (2.8 ml) at 0° C. The mixture was stirred at this temperature for 1 hour. After addition of methanol (5 ml), the reaction mixture was warmed to room temperature and diluted with water. The product was extracted into methylene chloride, and the combined organic layers were washed with brine and dried over magnesium sulfate. Removal of solvent in vacuo provided the title compound as a white solid, (570 mg, 2.1 mmol, 93% yield).

¹H NMR (CDCl₃): 7.32 (m, 5H), 5.11 (s, 2H), 3.97 (m, 2H), 3.45 (m, 1H), 3.06 (m, 1H), 2.03 (m, 1H) 1.78 (m, 2H), 1.47 (m, 1H), 0.81 (t, J=5.3 Hz, 1H).

5.

3-Benzyloxycarbonyl-1-(tert-butoxycarbonyl)amino-3-azabicyclo[4.1.0]hexane

To a solution of the compound of step 4 (540 mg, 1.96 mmol) in acetone (8 ml) was added triethylamine (0.303 ml, 2.16 mmol); the resulting solution was cooled to 0° C. in an ice bath. Ethyl chloroformate (0.224 ml, 2.35 mmol) was added slowly and the mixture was stirred for 30 minutes. A solution of sodium azide (1.27 g, 19.6 mmol) in 4 ml of water was added and the stirring was continued for an additional 2 hours at 0° C. The reaction mixture was diluted with water and extracted with ether. The organic layer was then washed with brine, dried over magnesium sulfate, and concentrated on a rotary evaporator with the water bath at 25°–30° C.; the acyl azide was obtained as a yellow oil.

A solution of pyridium tosylate (1.5 mg, catalytic amount) in t-butyl alcohol (4.5 ml) and toluene (20 ml) was heated to 105°. A solution of the acyl azide in toluene (5 ml) was added dropwise, and the resulting solution was stirred at reflux overnight.

After cooling to room temperature, the toluene was removed on a rotary evaporator to afford a slightly brown oil. The crude product was chromatographed on silica gel (eluant: 25%, then 40% ethyl acetate/hexane) to provide the title compound as a colorless liquid (478 mg, 1.38 mmol, 71% yield).

$^1$H NMR (CDCl$_3$): 7.31–7.27 (m, 5H), 5.09 (s, 2H), 4.90 (bs, 1H), 4.12 (bd, J=2.0 Hz, 1H), 3.55 (m, 1H), 3.47 (m, 1H), 3.05 (m, 1H), 2.09 (m, 1H), 1.67 (m, 1H), 1.40 (s, 9H), 1.27 (m, 1H), 0.80 (m, 1H), 0.51 (t, J=5.9 Hz, 1H).

6.
1-(tert-Butoxycarbonyl)amino-3-azabicyclo[4.1.0]hexane

To a solution of the compound of Step 5 (1.24 g, 3.58 mmol) in ethanol (20 ml) was added ammonium formate (678 mg, 10.76 mmol) followed by palladium on activated carbon (10% palladium content, 113.8 mg, 1.1 mmol). The mixture was stirred at room temperature for 23 hours. The solid material was removed by filtration, and the filtrate concentrated on a rotary evaporator to afford the title compound as a pale yellow solid (1.78 g, >100% weight recovery).

$^1$H NMR (CDCl$_3$): 5.90 (bs, 1H), 5.26 (m,1H), 3.29 (m, 1H), 3.22 (m, 1H), 2.84 (m, 1H), 2.65 (m, 1H), 2.16 (m, 1H), 1.68 (m, 1H), 1.40 (s, 9H), 1.25 (m, 1H), 0.95 (m, 1H), 0.78 (m, 1H).

EXAMPLE O

1.
[1α,5β,6α]-3-Benzyloxycarbonyl-5-hydroxy-3-azabicyclo[4.1.0]hexane

A flask containing samarium metal (2.7 g, 18.0 mmol) was flame-dried, then charged with tetrahydrofuran (40 ml). A tetrahydrofuran solution (30 ml) of mercuric chloride (467 mg, 1.72 mmol) was added and the mixture was stirred for ten minutes. After addition of 1-benzyloxycarbonyl-5-hydroxy-1,2,5,6-tetrahydropyridine, the flask was cooled to −78° C., and chloroiodomethane (1.25 ml, 17.2 mmol) was added dropwise. The mixture was stirred at room temperature overnight, quenched with saturated aqueous K$_2$CO$_3$ solution, and extracted with ether. The ether layer was washed with brine, dried over MgSO$_4$, and concentrated in vacuo to give a yellow oil. This crude material was chromatographed on neutral alumina-activity I (eluant: 50% ethyl acetate/hexane), providing the title compound as a colorless liquid (750 mg, 3.0 mmol, 81% yield).

$^1$H NMR (CDCl$_3$): 7.34 (m, 5H), 5.10 (s, 2H), 4.21 (bs, 1H), 3.68 (d, J=13.2 Hz, 1H), 3.59 (dd, J=13.4, 5.2 Hz, 1H), 3.36 (dd, J=13.9, 4.9 Hz, 1H), 3.16 (dd, J=13.9, 5.6 Hz, 1H), 1.44 (m, 1H), 1.32 (bm, 1H), 0.65 (m, 1H), 0.49 (q, J=5.2 H 1H).

2.
[1α,5β,6α]-3-Benzyl-5-hydroxy-3-azabicyclo[4.1.0]-heptane

To a solution of the compound of Step 1 (3.55 g, 14.36 mmol) in ethanol (150 ml) was added ammonium formate (2.71 g, 43.1 mmol), followed by addition of palladium on activated carbon (10% palladium content, 456 mg, 4.3 mmol). The mixture was stirred at room temperature for 23 hours, then filtered. The filtrate was concentrated on a rotary evaporator to afford the secondary amine (1.62 g, 14.3 mmol, 100% yield).

To a solution of the above-mentioned secondary amine in methanol (150 ml) was added benzaldehyde (1.6 ml, 15.8 mmol) and acetic acid (0.82 ml, 14 mmol) followed by addition of sodium cyanoborohydride (1.6 g, 14 mmol). The mixture was stirred at room temperature overnight. The resulting solution was treated with HCl until the pH value of the solution was about 3. A small amount of gas evulention was observed. The solvent was removed in vacuo, and the residue was treated with aqueous K$_2$CO$_3$ solution (pH,>10) and extracted with methylene chloride. The organic layer was washed with brine, dried over magnesium sulfate and evaporated to give the title compound (2.7 g, 13.3 mmol, 93% yield).

$^1$H NMR (CDCl$_3$): 7.34 (m, 2H), 7.25 (m, 3H), 4.16 (m, 1H), 3.43 (d, J=13.1 Hz, 1H), 3.36 (d, J=13.1 Hz, 1H), 2.62 (d, J=10.8 Hz, 1H), 2.52 (dd, J=11.3 Hz, 5.3, 1H), 2.28 (dd, J=11.8 Hz, 4.5, 1H), 2.14 (dd, J=11.8 Hz, 4.6, 1H), 1.68 (bs, 1H), 1.38 (m, 1H), 1.24 (m, 1H), 0.64 (m, 1H), 0.52 (m, 1H).

3. 3-Benzyl-3-azabicclo[4.1.0]heptan-5-one

To a solution of dimethylsulfoxide (4.8 ml, 68.5 mmol) in methylene chloride (150 ml) at −78° C. was added oxalyl chloride (2.9 ml, 34 mmol). After 15 minutes, the compound of Step 2 (3.4 g, 17 mmol) was added slowly at this temperature. The mixture was stirred at -78° C. for 40 minutes. To this solution was added triethylamine (14.32 ml, 102.8 mmol). The stirring was continued for an additional 5 minutes and the reaction was allowed to warm to room temperature. The reaction mixture was poured into saturated sodium chloride solution and extracted with methylene chloride. The organic layer was washed with brine, dried over magnesium sulfate and evaporated to give the crude material. This was purified by silica gel chromatography (eluant: 15% ethyl acetate/hexane). The title compound was obtained as a viscous oil (2.23 g, 11.1 mmol, 65% yield).

$^1$H NMR (CDCl$_3$) 7.32–7.21 (m, 5H), 3.50 (d, J=13.2 Hz, 1H), 3.42 (d, J=13.2 Hz, 1H), 3.26 (d, J=18.5 Hz, 1H), 3.09 (d, J=11.1 Hz, 1H), 2.58 (d, J=18.5 Hz, 1H), 2.45 (dd, J=11.1, 1.3 Hz, 1H), 1.92 (q, J=4.6 Hz, 1H), 1.79 (m, 1H), 1.69 (m, 1H), 1.06 (m, 1H).

4. 3-Benzyl-3-azabicyclo[4.1.0]heptan-5-one oxime

A solution of the compound of step 3 (2.23 g, 11.1 mmol) and hydroxylamine hydrochloride (1.0 g, 14.4 mmol) in 80% ethanol (110 ml) was stirred at reflux for 30 minutes. The solvent was removed in vacuo, and the residue was taken up in ether. The organic layer was washed with brine, dried over magnesium sulfate and evaporated to give 3-benzyl-3-azabicyclo[4.1.0]heptan-5-one oxime as a viscous yellow oil (2.28 g, 10.6 mmol, 95% yield).

¹H NMR (CDCl₃, mixture of two isomers): 8.75 (br m, 2H), 7.34–7.17 (m, 10H), 3.77 (d, J=17.8 Hz, 1H), 3.47 (2 doublets, J=13.2 Hz, 2H), 3.46 (2 doublets, J=13.2 Hz, 2H), 3.43 (m, 1H), 3.15 (d, J=14.0 Hz, 1H), 2.96 (d, J=11.0 Hz, 1H), 2.73 (d, J=17.8 Hz, 1H), 2.67 (d, J=14.0 Hz, 1H), 2.47 (dd, J=11.0, 3.6 Hz, 1H), 2.31 (d, J=11.0 Hz, 1H), 2.17 (m, 1H), 1.71 (m, 1H), 1.43 {m, 2H}, 1.36 {m, 1H}, 1.05 {m, 1H), 0.99 {m, 1H), 0.76 (m, 1H).

5.
[1α,5α,6α]-3-Benzyl-5-(tert-butoxycarbonyl)amino-3-azabicyclo[4.1.0]heptane To a solution of the compound of step 4 (2.28 g, 10.6 mmol) in tetrahydrofuran (50 ml) was added a solution of lithium aluminum hydride in tetrahydrofuran (60.6 mmol). The mixture was heated to reflux for 2 hours and, after being cooled to room temperature, was quenched with ethyl acetate (11.6 ml) followed by water (2 ml), aqueous NaOH (15% solution, 6.9 ml) and water (6.9 ml). The resulting precipitate was removed by filtration; the filtrate was diluted with saturated aqueous sodium bicarbonate and extracted with chloroform. The organic layer was washed with brine, dried over magnesium sulfate and evaporated to give the title compound as a viscous yellow oil (1.95 g, 9.65 mmol, 91% yield). This was carried on to the title compound without purification, via one of two routes:

a) Via di-t-butyl dicarbonate and triethylamine.

To a solution of 3-benzyl-5-amino-3-azabicyclo[4.1.0]-heptane (1.95 g, 9.6 mmol) and di-t-butyl dicarbonate (2.3 g, 10.5 mmol) in dioxane (90 ml) and water (10 ml) was added triethylamine (1.6 ml, 11.5 mmol). The mixture was stirred at room temperature for 5 hours, diluted with saturated sodium bicarbonate and extracted with methylene chloride. The organic layer was washed with brine, dried over magnesium sulfate and evaporated to give a yellow oil. This oil was chromatographed on silica gel (eluant: 30% ethyl acetate/hexane) to afford the title compound (1.3 g, 4.3 mmol, 45% yield) from the fraction with high R$_f$ value (R$_f$ 0.82, 30% ethyl acetate/hexane). The fraction with low R$_f$ value (R$_f$ 0.68, 30% ethyl acetate/hexane) provided the [1α,5β,6α] isomer (0.56 g, 1.85 mmol, 19% yield).

¹H NMR for title compound (CDCl₃): 7.31–7.19 [m, 5H), 5.24 (d, J=8.1 Hz, 1H), 3.92 (bs, 1H), 3.38 (d, J=13.2 Hz, 1H), 3.31 (d, J=13.2 Hz, 1H). 2.95 (dd, J=11.2, 7.6 Hz, 1H), 2.31 (d, J=11.9 Hz, 1H), 2.13 (m, 2H), 1.41 (s, 9H), 1.09 (m, 1H), 0.95 (m, 1H), 0.63 (m, 1H), 0.26 (m, 1H).

¹H NMR for [1α,5β,6α] isomer (CDCl₃) 7.30–7.20 (m, 5H), 4.70 (bd, 1H), 4. (m, 1H), 3.42 (d, J=13.1 Hz, 1H), 3.34 (d, J=13.1 Hz, 1H), 2.61 (m, 1H), 2.51 (m, 1H), 2.31 (dd, J=11.9, 4.9 Hz, 1H), 2.11 (dd, J=11.9, 3.5 Hz, 1H), 1.40 (s, 9H), 1.31 (m, 1H), 1.17 (m, 1H), 0.47 (m, 2H).

b) Via di-t-butyl dicarbonate and sodium hydroxide.

To a solution of 3-benzyl-5-amino-3-azabicyclo[4.1.0]-heptane (518 mg, 2.56 mmol) and di-t-butyl dicarbonate (671 mg, 3.58 mmol) in dioxane (15 ml) was added powdered sodium hydroxide (143 mg) followed by addition of water (5 ml). The mixture was stirred for 1 hour, diluted with water and extracted with ether. The ether layer was washed with brine, dried over magnesium sulfate and evaporated to give an off-white solid, which was chromatographed on silica gel (eluant 30% ethyl acetate/hexane) to afford the title compound as a white solid (187 mg, 0.619 mmol, 24% yield), the [1α,6β,6α] isomer of the title product (144 mg, 0.477 mmol, 19% yield), and a mixture of the title compound and its isomer (263 mg, 0.87 mmol, 34% yield).

6
[1α,5α,6α]-5-(tert-Butoxycarbonyl)amino-3-azabicyclo[4.1.0]heptane

To a solution of the title compound of step 5 (1.3 g, 4.3 mmol) in ethanol (50 ml) was added ammonium formate (0.81 g, 12.9 mmol) followed by palladium on activated carbon (10% palladium content, 0.136 g, 1.29 mmol). The mixture was stirred at room temperature for 2 hours, and then filtered. The filtrate was concentrated in vacuo to afford the title compound as a white solid (830 mg, 3.9 mmol, 91% yield).

¹H NMR (CD30D): 3.60 (m, 1H) 3.10 (dd, J=13.1, 5.7 Hz, 1H), 2.83 (d, J=13.1 Hz, 1H), 2.61 (dd, J=13.1, 4.7 Hz, 1H), 2.27 (dd, J=13.1, 7.1 Hz, 1H), 1.43 (s, 9H), 0.99 (m, 1H), 0.89 (m, 1H), 0.69 (m, 1H), 0.30 (q, J=5.4 Hz, 1H).

EXAMPLE P

1.
[1α,5β,6α]-5-(tert-Butoxycarbonyl)amino-3-azabicyclo[4.1.0]heptane

To a solution of [1α,5β,6α]-3-benzyl-5-(tert-butoxycarbonyl)amino-3-azabicyc [4.1.0]heptane, obtained as the minor isomer from Preparation 0.5, (800 mg, 2.64 mmol) in ethanol (50 ml) was added ammonium formate (500 mg, 7.92 mmol) followed by palladium on activated carbon (10% palladium content, 837 mg, 0.79 mmol). The mixture was stirred at room temperature for 1.5 hours, then filtered. The filtrate was concentrated in vacuo to afford 570 mg of the title compound as a waxy yellow solid (570 mg, >100% weight recovery).

¹H NMR (CDCl₃): 4.80 (bm, 1H), 4.01 (m, 1H), 3.11 (m, 2H), 2.85 (m, 2H), 2.33 (m, 1H), 1.42 (s, 9H), 1.33 (m, 1H), 1.19 (m, 1H), 0.57 (m, 1H), 0.45 (m, 1H).

EXAMPLE Q

1.
[1α,6α,7α]-3-Benzyloxycarbonyl-3-azabicyclo[4.1.0]heptane-7-carboxylic acid, ethyl ester A solution of benzyl 1,2,5,6-tetrahydropyridine-1-carboxylate (20 g, 92 mmol) in methylene chloride (92 ml) was treated with rhodium acetate (1.2 g, 5.5 mmol). A solution of ethyl diazoacetate (31.5 g, 276 mmol) in methylene chloride (8.6 ml) was then added over 22 hours, via syringe pump. After completion of the addition, the reaction mixture was filtered through celite; concentration of the filtrate provided the title compound, which was used in step 2 without purification.

¹H NMR (CDCl₃): 7.32–7.23 (m, 5H), 5.09 (s, 2H), 4.08 (q, J=7.3 Hz, 2H), 3.96 (d, J=13.8 Hz, 1H), 3.55 (dd, J=13.8, 4.1 Hz, 1H), 3.45 (bm, 1H), 3.01 (m, 1H), 1.96 (m, 1H), 1.78–1.66 (bm, 3H), 1.45 (t, J=4.3 Hz, 1H), 1.23 (t, J=7.3 Hz, 3H).

2.
[1α,6α,7α]-3-Benzyloxycarbonyl-3-azabicyclo[4.1.0]heptane-7-carboxylic acid The title compound of step 1 was dissolved in aqueous dioxane (20% by volume, 200 ml). Powdered sodium hydroxide (38 g) was added, and the mixture was stirred at 85° C. overnight. After being cooled to room temperature, the solution was extracted with ether. The aqueous layer was acidified with sodium bisulfate to a pH of 2 and extracted with methylene chloride. The methylene chloride layers were washed with brine, dried over magnesium sulfate and concentrated to afford the title compound (13.09 g, 47.5 mmol, crude). This material was utilized in the next reaction step without purification.

$^1$H NMR (CDCl$_3$): 7.32–7.23 (m, 5H), 5.09 (s, 2H), 3.96 (d, J=13.8 Hz, 1H), 3.76 (m, 1H), 3.56 (dd, J=13.8, 3.9 Hz, 1H), 3.47 (m, 1H), 3.02 (m, 2H), 1.96 (m, 1H), 1.75 (m, 1H), 1.46 (t, J=3.9 Hz, 1H).

3.

[1α,6α,7α]-3-Benzyloxycarbonyl-7-tert-butoxycarbonyl)amino-3-azabicyclo[4.1.0]heptane A mixture of the compound of step 2 (13.09 g, 47.5 mmol) and triethylamine (7.28 ml, 52.2 mmol) in acetone (150 ml) was cooled to 0° C.; ethyl chloroformate (5.4 ml, 57.0 mmol) was added dropwise. The mixture was stirred at 0° C. for 30 minutes. A solution of sodium azide (30.85 g, 475 mmol) in water (70 ml) was then added slowly. After an additional 2 hours, the mixture was diluted with water and extracted with ether. The ether layer was washed with brine, dried over magnesium sulfate and concentrated in vacuo to give the acyl azide (7.90 g, 26.3 mmol, crude) which was used directly in the next reaction.

A solution of the acyl azide in toluene (150 ml) was added dropwise to a toluene solution (150 ml) of t-butanol (30 ml) and pyridinium tosylate (9 mg) at 100° C. After completion of the addition, the reaction mixture was maintained at 100° C. for 12 hours. The reaction mixture was concentrated in vacuo, and the residue was chromatographed on silica gel (eluant: 20% ethyl acetate/hexane), providing the title compound as a viscous yellow oil, (2.4 g, 6.9 mmol, 7.5% yield from benzyl 1,2,5,6-tetrahydropyridine-1-carboxylate).

$^1$H NMR (CDCl$_3$): 7.31 (m, 5H), 5.08 (s, 2H), 4.72 (bs, 1H), 3.88 (bd, J=13.5 Hz, 1H), 3.62 (bm, 1H), 3.32 (bm, 1H), 3.00 (bm, 1H), 2.27 (bm, 1H), 1.94 (m, 1H), 1.77 (m, 1H), 1.41 (s, 9H), 1.19 (m, 2H).

4. [1α,5α,6α]-7-(tert-Butoxycarbonyl)amino-3-azabicyclo[4.1.0]heptane

To a solution of the compound of step 3 (2.3 g, 6.6 mmol) in ethanol (100 ml) was added ammonium formate (1.24 g, 19.8 mmol) followed by palladium on activated carbon (10% palladium content, 2.09 g, 1.9 mmol). The mixture was stirred at 60° C. for 1 hour and then at room temperature overnight. The reaction mixture was filtered, and the filtrate was concentrated in vacuo to afford the title compound as a viscous, pale yellow oil (1.38 g, 6.51 mmol, 91% yield).

$^1$H NMR (CD OD): 3.20 (dd, J=13.2, 5.8 Hz, 1H), 2.97 (dd, J=13.2, 1.5 Hz, 1H), 2.45 (m, 1H), 2.43 (m, 1H), 2.33 (m, 1H), 1.92 (m, 1H), 1.72 (m, 1H), 1.43 (s, 9H), 1.11 (m, 1H), 1.03 (m, 1H).

EXAMPLE R

1.

[1α,6α,6α]-6-Amino-3-benzyloxycarbonyl-3-azabicyclo 3.1.0] hexane

[1α,5α,6α]-6-tert-Butoxycarbonylamino-3-benzyloxycarbonyl-3-azabicyclo[3.1.0]hexane (640 mg, 1.93 mmol) was dissolved in methylene chloride (6 ml) and treated with trifluoroacetic acid (2 ml). The resulting solution was allowed to stir at room temperature for 1.5 hours, then concentrated in vacuo. The residue was partitioned between aqueous sodium carbonate and chloroform, and the organic layer was dried over sodium sulfate and concentrated to provide the title product as a yellow oil (421 mg, 1.81 mmol, 94% yield).

$^1$H NMR (CDCl$_3$: 7.24 (s, 5H), 4.99 (s, 2H), 3.49 (m, 2H), 3.31 (m, 2H), 1.96 (bs, 1H), 1.41 (bs, 4H).

2.

[1α,5α,6α]-3-Benzyloxvcarbonyl-6-(N-tert-butoxycarbonyl-L-Ala-L-Ala-amino)-3-azabicyclo[3.1.0]hexane The title product of Example R.1. (400 mg, 1.72 mmol) was dissolved in methylene chloride (10 ml) and treated with N-tert-butoxycarbonyl-L-alanine-L-alanine (450 mg, 1.75 mmol), 1-(3-dimethylaminopropyl)-3-ethylcarbodiimide hydrochloride (335 mg, 1.75 mmol), 1-hydroxybenzotriazole hydrate (235 mg, 1.75 mmol) and triethylamine (485 μl, 3.5 mmol). After stirring for 16 hours at room temperature, the mixture was treated with hydrochloric acid (1N, 30 ml) and extracted with methylene chloride. After drying over sodium sulfate, the organic layers were filtered and concentrated to a residue which was purified by column chromatography (eluant 10% methanol/chloroform) to provide the title product as a white foam, mp 158°–161° C. with decomposition (382 mg, 0.80 mmol, 47% yield).

$^1$H NMR (CDCl$_3$): 7.27 (m, 5H), 7.18 (bs, 1H), 6.94 (m, 1H), 5.38 (m, 1H), 5.02 (s, 2H), 4.38 (m, 1H), 4.05 (m, 1H), 3.67 (m, 2H), 3.39 (M, 2H), 2.39 (s, 1H), 1.66 (s, 2H), 1.38 (s, 9H), 1.29 (d, J =6.9 Hz, 6H).

3.

[1α,5α,6α]-6-(N-tert-Butoxycarbonyl-L-Ala-L-Ala-amino)-3-azabicyclo[3.1.0]hexane The title product of Example R.2. (350 mg, 0.74 mmol) was dissolved in methanol (50 ml), treated with palladium hydroxide (50 mg) and hydrogenated at 50 psi for two hours. The catalyst was removed by filtration, and the filtrate concentrated in vacuo, to provide a residue, which was purified by column chromatography (eluant: 50:50:1 chloroform: methanol: concentrated ammonium hydroxide). The title product was obtained as a solid, mp 188° C. with decomposition (208 mg, 0.61 mmol, 82% yield).

$^1$H NMR (CDCl$_3$): 7.00 (bs, 1H), 6.90 (m, 1H), 5.14 (bs, 1H), 4.38 (m, 1H), 4.07 (m, 1H), 3.22 (m, 2H), 3.05 (m, 2H), 2.62 (s, 1H), 1.67 (s, 2H), 1.42 (s, 9H), 1.33 (d, J=7.3 Hz, 6H).

The following examples illustrate the invention.

EXAMPLE 1

7-(3-Azabicyclo[3.1.0]hex-3-yl)-1-cyclopropyl-6-fluoro-1,4-dihydro-4-oxo-quinoline-3-carboxylic acid A solution of the hydrochloride salt of 3-azabicyclo -3.1.0]hexane (157 mg, 1.31 mmol), (prepared in a manner similar to that described in U.S. Pat. No. 4,183,857) in dimethylsulfoxide (13 ml) was treated with -cyclopropyl-6,7-difluoro-1,4-dihydro-4-oxo-quinolinecarboxylic acid (348 mg, 1.31 mmol) and triethylamine (0.58 ml, 3.9 mmol) and heated for 18 hours. Filtration of the reaction mixture provided a white solid, which was purified by column chromatography (eluant: 1% acetic acid in chloroform, then 5% acetic acid in chloroform, then methanol) to give the title product as a white solid, melting point 290° (186 mg, 0.43 mmol, 33% yield). $^1$H NMR (DMSO-d$_6$): 8.54 (s, 1H), 7.75 (d, J=14 Hz, 1H), 7.08 (d, J=9 Hz, 1H), 3.83 (dd, J=4, 10

Hz, 2H), 3.73 (bs, 1H), 3.62 (bd, J=10 Hz, 2H), 1.77 (m, 2H), 1.30 (d, J=6 Hz, 2H), 1.14 (bs, 2H), 0.77 (m, 1H), 0.30 (m, 1H).

EXAMPLE 2

A.

7-1-[(N-tert-Butoxycarbonyl)aminomethyl]-3-azabicyclo[3.1.0]hex-3-yl-1-cyclopropyl-6-fluoro-1,4-dihydro-4-oxo-quinoline-3-carboxylic acid A mixture of 1-[(N-tert-butoxycarbonyl)aminomethyl]-3-azabicyclo[3.1.0]hexane (0.30 g, 1.41 mmol) and triethylamine (0.39 ml, 2.8 mmol) in acetonitrile (20 ml) was treated with 1-cyclopropyl-6,7-difluoro-1,4-dihydro-4-oxo-quinoline-3-carboxylic acid (0.375 g, 1.41 mmol) and heated to 50° for 21 hours. The temperature was then increased to 80° for 24 hours. Filtration of the reaction mixture then provided the title product as a white solid, mp 235.5°-236° (508 mg, 1.11 mmol, 79% yield). $^1$H NMR (DCDl$_3$/CD$_3$OD): 8.62 (s, 1H), 7.84 (d, J=14 Hz, 1H), 6.88 (d, J=7 Hz, 1H), 5.06 (vbs, 1H), 3.84 (m, 2H), 3.68 (m, 1H), 3.58 (m, 1H), 3.48 (m, 1H), 3.36 (bs, 2H), 1.64 (m, 1H), 1.45 (s, 9H), 1.36 (m, 2H), 1.17 (m, 2H), 0.87 (m, 1H), 0.66 (m, 1H).

B.

7-(1-Aminomethyl-3-azabicyclo[3.1.0]hex-3-yl)-1-cyclopropyl-6-fluoro-1,4-dihydro-4-oxo-quinoline-3-carboxylic acid, hydrochloride salt The title compound of Example 2A (442.8 mg, 0.97 mmol) was mixed with hydrochloric acid (3.0 ml of a 6 M solution) and acetic acid (3.0 ml) and heated to 100° for 1 hour. The resulting solution was cooled and concentrated in vacuo by azeotropic distillation with toluene, to provide a yellow residue, which was triturated with isopropanol and filtered. The title product was obtained as a white solid, mp 261° with decomposition (350 mg, 0.89 mmol, 92% yield). $^1$H NMR (DMSO-d : 8.57 (s, 1H), 7.79 (d, J=13 Hz, 1H), 7.11 (d, J=7 Hz, 1H), 4.00 (m, 1H), 3.81 (m, 1H), 3.71 (d, J=9 Hz, 2H), 3.70 (m, 1H), 3.18 (d, J=11 Hz, 1H), 3.06 (d, J=11 Hz, 1H), 1.88 (m, 1H), 1.38 (bd, J=7 Hz, 2H), 1.16 (bs, 2H), 1.06 (m, 1H), 0.68 (m, 1H).

EXAMPLE 3

A.

7-(1-[(N-tert-Butoxycarbnyl)aminomethyl]-3-azbicyclo[3.1.0]hex-3-yl{-1-cyclopropyl-6,8-difluoro-1,4-dihydro-4-ox-quinoline-3-carboxylic acid A mixture of 1-[(N-tert-butoxycarbonyl)aminomethyl]-3-azabicyclo[3.1.0]hexane (501 mg, 2.35 mmol) and triethylamine (0.655 ml, 4.7 mmol) in acetonitrile (25 ml) was treated with 1-cyclopropyl-6,7,8-trifluoro-1,4-dihydro-4-oxo-quinoline-3-carboxylic acid (668.3 mg, 2.35 mmol) and heated to 80° for 24 hours. Filtration of the reaction mixture then provided the title product as a white solid, mp 188°-189.5° (851 mg, 1.79 mmol, 76% yield). $^1$H NMR (CDCl$_3$): 14.6 (s, 1H), 8.72 (s, 1H), 7.80 (dd, J=13, 2 Hz, 1H), 4.67 (bs, 1H), 3.94 (m, 1H), 3.83 (d, J=10 Hz, 1H), 3.76 (s, 2H), 3.66 (d, J=10 Hz, 1H), 3.42 (dd, J=14, 6 Hz, 1H), 3.29 (bdd, J=14, 6 Hz, 1H), 1.44 (bs, 10H), 1.24 (m, 2H), 1.12 (m, 2H), 0.70 (m, 2H).

B.

7-[1-Aminomethyl-3-azabicyclo[3.1.0]hex-3-yl]-1-cyclopropyl-6,8-difluoro-1,4-dihydro-4-oxo-quinoline-3-carboxylic acid, hydrochloride salt The title compound of Example 3B (779.4 mg, 1.63 mmol) was mixed with hydrochloric acid (5.0 ml of a 6M solution) and acetic acid (5.0 ml) and heated to 100° for 1.75 hours. The resulting solution was cooled and concentrated in vacuo by azeotropic distillation with toluene, to provide a residue which was triturated with isopropanol and filtered. The title product was obtained as a light yellow solid, mp 251° with decomposition (556 mg, 1.35 mmol, 83% yield). $^1$H NMR (DMSO-d$_6$): 8.63 (s, 1H), 7.74 (dd, J=13, 2 Hz, 1H), 4.08 (m, 1H), 3.90 (d, J=10 Hz, 1H), 3.70 (m, 3H), 3.17 (d, J=13 Hz, 1H), 3.03 (d, J=13 Hz, 1H), 1.73 (m, 1H), 1.15 (m, 4H), 0.93 (m, 1H), 0.66 (m, 1H).

EXAMPLE 4

A.

7-(1-[(N-tert-Butoxycarbonyl)aminomethyl]-3-azabicyclo[3.1.0]hex-3-yl)-1-cyclopropyl-6-fluoro-1,4-dihdro-4-oxo-1,8-naphthyridine-3-carboxylic acid A mixture of 1-[(N-tert-butoxycarbonyl)aminomethyl]-3-azabicyclo[3.1.0]hexane (52.5 mg, 0.24 mmol) and triethylamine (66 μl, 0.48 mmol) in acetonitrile (3 ml) was treated with 7-chloro-1-cyclopropyl-6-fluoro-1,4-dihydro-4-oxo-1,8-naphthyridine-3-carboxylic acid (70 mg, 0.24 mmol) and heated to 80° for 20 hours. Filtration of the reaction mixture then provided the title product as a white solid, mp 234° with decomposition (89.0 mg, 0.19 mmol, 79% yield). $^1$H NMR (CDCl$_3$): 8.66 (s, 1H), 7.96 (d, J=12 Hz, 1H), 4.72 (bs, 1H), 4.11 (m, 2H), 3.80 (m, 2H), 3.58 (m, 1H), 3.36 (d, J=6 Hz, 2H), 1.60 (m, 1H), 1.43 (s, 9H), 1.22 (m, 2H), 1.02 (m, 2H), 0.88 (m, 1H), 0.58 (m, 1H).

B.

7-[1-Aminomethyl-3-azabicyclo[3.1.0]hex-3-yl]-1-cyclopropyl-6-fluoro-1,4-dihydro-4-oxo-1,8-naphthyridine-3-carboxylic acid, hydrochloride salt The title compound of Example 4A (89 mg, 0.194 mmol) was mixed with hydrochloric acid (1.5 ml of a 6M solution) and acetic acid (1.5 ml) and heated to 100° for 1 hour. The resulting solution was cooled and concentrated in vacuo by azeotropic distillation with toluene, to provide a residue which was triturated with isopropanol and filtered. The title product was obtained as a light yellow solid, mp 283° with decomposition (48.4 mg, 0.122 mmol, 64% yield). $^1$H NMR (DMSO-d 8.52 (s, 1H), 8.16 (bs, 1H), 7.95 (d, J=13 Hz, 1H), 4.18 (m, 1H), 4.02 (m, 1H), 3.86 (m, 2H), 3.66 (m, 1H), 3.08 (m, 2H), 1.86 (m, 1H), 1.24 (m, 2H), 1.06 (m, 3H), 0.61 (m, 1H).

EXAMPLE 5

A.

7-(1-[(N-tert-Butoxycarbonyl)aminomethyl]-3-azabicyclo3.1.0]hex-3-yl)-1-cyclopropyl-6-fluoro-8-methoxy-1,4-dihydro-4-oxo-quinoline-3-carboxylic acid A mixture of 1-[(N-tert-butoxycarbonyl)aminomethyl]-3-azabicyclo[3.1.0]hexane (209.6 mg, 0.99 mmol) and triethylamine (0.273 ml, 1.96 mmol) in dimethylsulfoxide (10 ml) was treated with 1-cyclopropyl-6,7-difluoro-8-methoxy-1,4-dihydro-4-oxo-quinoline-3-carboxylic acid (242.9 mg, 0.82 mmol) and heated to 80° for 42 hours. The reaction mixture was then concentrated in vacuo and the resulting solid was triturated with isopropanol to deliver the title produce as a white solid, mp 212°-213° with decomposition (183 mg, 0.376 mol, 46% yield). $^1$H NMR (CDCl$_3$): 8.79 (s, 1H), 7.79 (d, J=13 Hz, 1H), 4.69 (m, 1H), 3.99 (m, 1H), 3.66 (m, 4H), 3.57 (s, 3H), 3.48 (m, 1H), 3.27 (m, 1H), 1.58 (bs, 1H), 1.46 (s, 9H), 1.19 (m, 2H), 0.98 (m, 2H), 0.72 (m, 2H).

B.

7-[1-Aminomethyl-3-azabicyclo[3.1.0]hex-3-yl]-1-cyclopropyl-6-fluoro-8-methoxy-1,4-dihydro-4-oxo-quinoline-3-carboxylic acid The title compound of Example 5A (166.7 mg, 0.34 mmol) was mixed with hydrochloric acid (2.5 ml of a 6M solution) and acetic acid (2.5 ml) and heated to 100° for 3.5 hours. The resulting solution was cooled and concentrated in vacuo by azeotropic distillation with heptane, to provide a residue which was trturated with isopropanol and ether. The product was then dissolved in water (2 ml), brought to pH 8.5 with sodium hydroxide solution (0.1N) and filtered to provide the title product as a greenish solid, mp 194°-196° (36.6 mg, 0.095 mmol, 28% yield). $^1$H NMR (D$_2$O/NaOD): 8.50 (s, 1H), 7.62 (d, J=14 Hz, 1H), 4.05 (bs, 1H), 3.71 (d, J=10 Hz, 1H), 3.55 (s, 3H), 3.5 (m, 3H), 2.90 (bd, J=13 Hz, 1H), 2.70 (bd, J=13 Hz, 1H), 1.44 (bs, 1H), 1.11 (m, 2H), 0.90 (bs, 2H), 0.62 (m, 2H).

EXAMPLE 6

A.

7-(1-[(N-acetyl)aminomethyl]-3-azabicyclo[3.1.0]-hex-3-yl)-6-fluoro-1-(2,4-difluorophenyl)-1,4-dihdro-4-oxo-1,8-naphthyridine-3-carboxylic acid, ethyl ester A mixture of 1-[(N-acetyl)aminomethyl]-3-azabicyclo[3.1.0]hexane (115.5 mg, 0.75 mmol) and triethylamine (312 μl, 2.25 mmol) in acetonitrile (20 ml) was treated with the ethyl ester of 7-chloro-6-fluoro-1-(2,4-difluorophenyl)-1,4-dihydro-4-oxo-1,8-naphthyridine-3-carboxylic acid (283 mg, 0.74 mmol) and heated to 80° for 20 hours. Additional 1-(N-acetyl)-aminomethyl-3-azabicyclo[3.1.0]hexane (97 mg) was added portionwise over 2.5 hours until thin layer chromatography indicated the absence of starting naphthyridine. The reaction mixture was concentrated in vacuo, and the residue chromatographed on silica gel (eluant: 189:10:1 chloroform: methanol: concentrated ammonium hydroxide). The title product was obtained as a colorless oil (280.3 mg, 0.56 mmol, 76% yield).

$^1$H NMR (CDCl$_3$): 8.36 (s, 1H), 7.93 (d, J=13 Hz, 1H), 7.37 (bs, 1H), 7.07 (bs, 2H), 6.15 {bs, 1H), 4.36 (q, J=7 Hz, 2H), 3.48 (m, 6H), 2.02 (s, 3H), 1.50 (m, 1H), 1.37 (t, J=7 Hz, 3H), 0.81 (m, 1H), 0.43 (m, 1H).

B.

7-[1-Aminomethyl-3-azabicyclo[3.1.0]hex-3-yl]-6-fluoro-1-(2,4-difluorophenyl)-1,4-dihydro-4-oxo-1,8-naphthyridine-3-carboxylic acid, hydrochloride salt The title compound of Example 6A (231.2 mg, 0.46 mmol) was mixed with hydrochloric acid (3 ml of a 6M solution) and acetic acid (3 ml) and heated to 100° for 24 hours. The resulting solution was cooled and concentrated in vacuo to provide a residue which was mixed with isopropanol and isopropyl ether and filtered. The filtrate was concentrated, and the product triturated with a small quantity of cold isopropanol to provide a white solid, which was dissolved in a minimum quantity of sodium hydroxide solution and acidified with hydrochloric acid until a precipitate appeared Filtration provided the title product as a yellow solid, mp 201°-203° (40 mg, 0.086 mmol, 19% yield). $^1$H NMR (D20/NaOD): 8.25 (s, 1H), 7.80 (d, J=13 Hz, 1H), 7.45 (m, 1H), 7.15 (m, 2H), 3.5 (vbm, 4H), 2.70 (bd, J=13 Hz, 1H), 2.60 (bd, J=13 Hz, 1H), 1.39 (bs, 1H), 0.68 (bs, 1H), 0.20 (bs, 1H).

EXAMPLE 7

A.

7-(1-[N-(tert-Butoxycarbonyl)ethylaminomethyl]-3-azabicyclo[3.1.0]hex-3-yl)-1-cyclopropyl-6-fluoro-1,4-dihydro-4-oxo-quinoline-3-carboxylic acid A mixture of 1-[N-(tert-butoxycarbonyl)ethylaminomethyl]-3-azabicyclo[3.1.0]hexane (45.3 mg, 0.18 mmol) and triethylamine (50 μl, 0.36 mmol) in acetonitrile (5 ml) was treated with 1-cyclopropyl-6,7-difluoro-1,4-dihydro-4-oxo-quinoline-3-carboxylic acid (50.0 mg, 0.18 mmol) and heated to 80° for 18 hours. Filtratation of the reaction mixture provided the title product as a white solid (26.8 mg, 0.055 mmol, 31% yield). $^1$H NMR (CDCl$_3$):8.67 (s, 1H), 7.90 (d, J=15 Hz, 1H), 6.89 (d, J=7 Hz, 1H), 3.87 (bs, 2H), 3.5 (m, 5H), 3.3 (bs, 2H), 1.6 (m, 1H), 1.49 (s, 9H), 1.33 (m, 2H), 1.14 (m, 5H), 0.83 (m, 1H), 0.68 (m, 1H).

B.

7-(1-Ethylaminomethyl-3-azabicyclo[3.1.0]hex-3-yl)-1-cyclopropyl-6-fluoro-1,4-dihydro-4-oxo-quinoline-3-carboxylic acid, hydrochloride salt The title compound of Example 7A (20.2 mg, 0.042 mmol) was mixed with hydrochloric acid (0.75 ml of a 6M solution) and acetic acid (0.75 ml) and heated to 100° for 2 hours. The resulting solution was concentrated in vacuo and the residue triturated with isopropanol and dried under vacuum to provide the title product as a yellow solid, mp 289°-293° with decomposition (11.2 mg, 0.027 mmol, 63% yield. $^1$H NMR (DMSO-d$_6$, 107°): 8.6 (s, 1H), 7.85 (d, J=14 Hz, 1H), 7.2 (d, J=7 Hz, 1H), 4.05 (m, 1H), 3.75 (m, 4H), 3.3 (d, J=10 Hz, 1H), 3.2 (d, J=10 Hz, 1H), 2.9 (m, 2H), 1.95 (m, 1H), 1.45 (m, 2H), 1.3 (t, J=7 Hz, 3H), 1.2 (m, 3H), 0.75 (m, 1H).

EXAMPLE 8

A.

7-(1-Acetylamino-3-azabicyclo[3.1.0]hex-3-yl)-1-cyclopropyl-6-fluoro-1,4-dihydro-4-oxo-1,8-naphthyridine-3-carboxylic acid A mixture of 1-acetylamino-3-azabicyclo[3.1.0]-hexane (150 mg, 0.70 mmol) and triethylamine (0.48 ml, 3.5 mmol) in acetonitrile (7 ml) was treated with 7-chloro-1-cyclopropyl-6-fluoro-1,4-dihydro-4-oxo-1,8-naphthyridine-3-carboxylic acid (192.1 mg, 0.68 mmol) and heated to 80° for 18 hours. Filtration of the reaction mixture provided the title product as a white solid, mp 275° with decomposition (135.8 mg, 0.35 mmol, 51% yield). $^1$H NMR (CDCl$_3$) 8.55 (s, 1H), 8.49 (s, 1H), 7.96 (d, J=13 Hz, 1H), 4.22 (m, 1H), 3.98 (bs, 2H), 3.81 (m, 1H), 3.68 (m, 1H), 1.82 (bs, 4H), 1.12 (m, 5H), 0.78 (m, 1H).

B.

7-(1-Amino-3-azabicyclo[3.1.0]hex-3-yl)-1-cyclopropyl-6-fluoro-1,4-dihydro-4-oxo-1,8-naphthyridine-3-carboxylic acid, hydrochloride salt The title compound of Example 8A (133 mg, 0.34 mmol) was mixed with hydrochloric acid (2.5 ml of a 6M solution) and acetic acid (2.5 ml) and heated to 100° for 18 hours. The resulting solution was cooled and concentrated in vacuo by azeotropic distillation with heptane, to provide a residue which was triturated with isopropanol. The title product was obtained as a yellow solid, mp 230° with decomposition (114.7 mg, 0.30 mmol, 88% yield). $^1$H NMR (DMSO-d$_6$): 8.57 (s, 1H), 8.01 (d, J=12 Hz, 1H), 4.35 (m, 1H), 4.00 (m, 3H), 3.66 (bs, 1H), 2.15 (bs, 1H), 1.40 (m, 1H), 1.18 (m, 2H), 1.09 (bs, 2H), 0.91 (bs, 1H).

EXAMPLE 9

A.

7-(1-Acetylamino-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester A mixture of 1-acetylamino-3-azabicyclo[3.1.0]-hexane (60 mg, 0.28 mmol) and triethylamine (195 μl, 1.4 mmol) in acetonitrile (10 ml) was treated with the ethyl ester of 7-chloro-6-fluoro-1-{2,4-difluoro-phenyl) -1,4-dihydro-4-oxo-1,8-naphthyridine-3-carboxylic acid (95.6 mg, 0.25 mmol) and heated to 80° for 20 hours. The reaction mixture was concentrated in vacuo, diluted with chloroform and washed with saturated aqueous sodium bicarbonate. The organic layer was dried over magnesium sulfate, filtered and concentrated in vacuo. The residue was chromatographed on silica gel (eluant: 189:10:1 chloroform: methanol: conc. ammonium hydroxide) to yield the title product as a yellow oil (120.8 mg, 0.25 mmol, 100% yield). $^1$H NMR (CDCl$_3$) 8.35 (s, 1H), 8.01 (d, J=13 Hz, 1H), 7.36 (m, 1H), 7.04 (m, 2H), 6.11 (bs, 1H), 4.35 (q, J=7 Hz, 2H), 3.96 (vbs, 1H), 3.69 (vbs, 3H), 1.96 (s, 3H), 1.73 (m, 1H), 1.37 (t, J=7 Hz, 3H), 1.06 (m, 1H), 0.71 (m, 1H).

B.

7-(1-Amino-3-azabicyclo[3.1.0]hex-3-yl)-6-fluoro-1-(2,4-difluorophenyl)-1,4-dihvdro-4-oxo-1,8-naphthyridine-3-carboxylic acid, hydrochloride salt The title compound of Example 9A (116 mg, 0.24 mmol) was mixed with hydrochloric acid (3 ml of a 6M solution) and acetic acid (3 ml) and heated to 100° for 18 hours. The resulting solution was cooled and concentrated in vacuo to provide a residue which was crystallized from ether/methanol. The resulting solid was dissolved in 0.5N sodium hydroxide solution and filtered. The filtrate was then acidified with hydrochloric acid until a precipitate appeared. Filtration of the resulting mixture provided the title product as a tan solid, mp 205° with decomposition (31.2 mg, 0.069 mmol, 29% yield). $^1$H NMR (D$_2$O/NaOH)): 8.26 (s, 1H), 7.76 (d, J=13 Hz, 1H), 7.42 (m, 1H), 7.15 (m, 2H), 3.82 (vbs, 1H), 3.4 (vbm, 3H), 1.41 (bs, 1H), 0.86 (m, 1H), 0.29 (bs, 1H).

EXAMPLE 10

A.

7-([1α,5α,6α]-6-[(N-tert-Butoxycarbonyl)aminomethyl-3-azabicyclo[3.1.0]hex-3-yl)-1-cyclopropyl-6-fluoro-1,4-dihydro-4-oxo-1,8-naphthyridine-3-carboxylic acid, ethyl ester A solution of [1,5,6]-6-[(tert-butoxycarbonyl)-aminomethyl]-3-azabicyclo[3.1.0]hexane (75 mg, 0.35 mmol) in acetonitrile (10 ml) and triethylamine (2 ml) was treated with the ethyl ester of 7-chloro-1-cyclopropyl-6-fluoro-1,4-dihydro-4-oxo-1,8-naphthyridine-3-carboxylic acid (105 mg, 0.34 mmol) and heated to 80° for 18 hours. Removal of solvent in vacuo gave a residue which was subjected to column chromatography (eluant: chloroform, then 5% methanol in chloroform) to provide the title product (132 mg, 0.27 mmol, 79% yield). $^1$H NMR (CDCl$_3$): 8.41 (s, 1H), 7.98 (d, J=13 Hz, 1H), 4.7 (bs, 1H), 4.35 (q, J=7 Hz, 2H), 4.08 (bd, J=11 Hz, 2H), 3.72 (bd, J=11 Hz, 2H), 3.45 (bs, 1H), 3.10 (m, 2H), 1.55 (bs, 2H), 1.40 (s, 9H), 1.36 (t, J=7 Hz, 3H), 1.15 (m, 2H), 0.98 (bs, 2H), 0.90 (bs, 1H).

B.

7-([1α,5α,6α]-6-Aminomethyl-3-azabicyclo[3.1.0]-hex-3-yl)-1-cyclopropyl-6-fluoro-1,4-dihydro-4-oxo-1,8-naphthyridine-3-carboxylic acid, hydrochloride salt The title compound of Example 10A (110 was dissolved in hydrochloric acid (6N, 6 ml) and acetic acid (6 ml) and heated to reflux for 18 hours. The solvents were then removed in vacuo, and the residue recrystallized from acetonitrile-methanol. The title product was obtained as fine white needle, mp 272° with decomposition (27 mg, 0.068 mmol, 30% yield).

$^1$H NMR (D 0, 93° ): 9.5 (s, 1H), 8.6 (d, J=14 Hz, 1H), 5.0 (bd, J=10 Hz, 2H), 4.7 (bd, J=10 Hz, 2H), 4.5 (bs, 1H), 3.8 (d, J=6 Hz, 2H), 2.7 (bs, 2H), 2.1 (m, 2H), 1.8 (bs, 3H).

EXAMPLE 11

A.

7-[1α,5α,6α]-6-tert-Butoxycarbonylamino-3-azabicyclo[3.1.0]hex-3-yl)-1-cyclopropyl-6-fluoro-1,4-dihydro-4-oxo-1,8-naphthyridine-3-carboxylic acid, ethyl ester A solution of [1α,5α,6α]-6-tert-butoxycarbonylamino-3-azabicyclo[3.1.0]hexane (149 mg, 0.75 mmol) in acetonitrile (25 ml) and triethylamine (3 ml) was treated with the ethyl ester of 7-chloro-1-cyclopropyl-6-fluoro-1,4-dihydro-4-oxo-1,8-naphthyridine-3-carboxylic acid (230 mg, 0.74 mmol) and heated to 80° for 15 hours. Removal of solvent in vacuo gave a residue which was subjected to column chromatography (eluant:chloroform) to provide material which upon trituration with diethyl ether gave the title product (206 mg, 0.45 mmol, 60% yield). 1H NMR (CDCl$_3$) 8.46 (s, 1H), 8.04 (d, J=13 Hz, 1H), 4.80 (bs, 1H), 4.37 (q, J=7 Hz, 2H), 4.17 (bd, J=11 Hz, 2H), 3.81 (bd, J=11 Hz, 2H), 3.46 (m, 1H), 2.38 (bs, 1H), 1.89 (bs, 2H), 1.45 (s, 9H), 1.39 (t, J=7 Hz, 3H), 1.18 (m, 2H), 0.99 (m, 2H).

B.

7-([1α,5α,6α]-6-Amino-3-azabicyclo[3.1.0]hex-3-yl)-1-cyclopropyl-6-fluoro-1,4-dihydro-4-oxo-1,8-naphthyridine-3-carboxylic acid, dihydrochloride salt The title compound of Example 11.A (170 mg, 0.37 mmol) was dissolved in hydrochloric acid (6N, 10 ml) and heated to reflux for 24 hours. The solvent was then removed in vacuo, and the residue recrystallized from acetonitrilemethanol. The title product was obtained as a pale yellow solid, mp 180° with decomposition (52 mg, 0.12 mmol, 34% yield). $^1$H NMR (methanol-d$_4$) 8.65 (s, 1H), 7.93 (d, J=13 Hz, 1H), 4.3 (bm, 2H), 3.98 (bm, 2H), 3.72 (bs, 1H), 2.68 (bs, 1H), 2.26 (bs, 2H), 1.30 (bs, 2H), 1.12 (bs, 2H).

EXAMPLE 12

A.

7-([1α,5α,6α]-6-tert-Butoxycarbonylamino-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester A solution of [1α,5α,6α]-6-tert-butoxycarbonylamino-3-azabicyclo[3.1.0]hexane (200 mg, 1.01 mmol) in acetonitrile (35 ml) and triethylamine (5 ml) was treated with the ethyl ester of 7-chloro-6-fluoro-1-(2,4-difluorophenyl)-1,4-dihydro-4-oxo-1,8-naphthyridine-3-carboxylic acid (385 mg, 1.01 mmol) and heated to 90° for 18 hours. Removal of solvent in vacuo gave a residue which was partitioned between ethyl acetate and water. The organic layer was treated with activated charcoal, filtered, and concentrated; the residue was then subjected to column chromatography (eluant: 5% methanol in chloroform). The material thus obtained was recrystallized from diethyl ether to give the title product m.p. 256°-258°, (296 mg, 0.54 mmol, 54% yield). $^1$H NMR (CDCl$_3$): 8.35 (s, 1H), 8.06 (d, J=13 Hz, 1H), 7.37 (m, 1H), 7.05 (m, 2H), 4.72 (vbs, 1H), 4.37 (q, J=7 Hz, 2H), 3.81 (vbs, 2H), 3.55 (bm, 2H), 2.26 (bs, 1H), 1.78 (bs, 2H), 1.43 (s, 9H), 1.38 (t, J=7 Hz, 2H).

B.

7-([1α,5α,6α]-6-Amino-3-azabicyclo[3.1.0]hex-3-yl)-6-fluoro-1-(2,4-difluorophenyl)-1,4-dihydro-4-oxo-1,8-naphthyridine-3-carboxylic acid, hydrochloride salt The title compound of Example 12.A (250 mg, 0.46 mmol) was dissolved in hydrochloric acid (6N, 20ml) and heated to reflux for 24 hours. The solvent was then removed in vacuo, and the residue triturated with acetonitrile, washed with diethyl ether and recrystallized from acetonitrile-methanol. The title product was obtained as a pale yellow solid, mp 246° with decomposition (116 mg, 0.26 mmol, 57% yield). $^1$H NMR (Methanol-d$_4$): 8.68 (s, 1H), 7.96 (d, J=13 Hz, 1H), 7.57 (m, 1H), 7.22 (m, 1H), 7.14 (m, 1H), 3.82 (vbs, 2H), 3.62 (vbs, 2H), 2.37 (bs, 1H), 2.03 (bs, 2H).

EXAMPLE 13

A.

7-([1α,5α,6α]-6-tert-Butoxycarbonylamino-3-azabicyclo[3.1.0]hex-3-yl)-6-tluoro-1-(2,4-difluorohenyl)-1,4-dihydro-4-oxo-quinoline-3-carboxylic acid, ethyl ester A solution of [1α,5α,6α]-6-tert-butoxycarbonylamino-3-azabicyclo[3.1.0]hexane (210 mg, 1.06 mmol) and 6,7-difluoro-1-(2,4-difluorophenyl)-1,4-dihydro-4-oxo-quinoline-3-carboxylic acid ethyl ester (365 mg, 1.0 mmol) in dimethylsulfoxide (20 ml) and triethylamine (5 ml) was heated at 80° C. for 60 hours. Solvent was removed in vacuo, nd the residue was purified by column chromatogaphy (eluant: chloroform). The title product was obtained as a yellow foam (432 mg, 0.79 mmol, 79% yield).

$^1$H NMR (CDCl$_3$): 8.23 (s, 1H), 7.96 (d, J=15 Hz, 1H), 7.43 (m, 1H), 7.14 (m, 2H), 5.65 (d, J=6.9 Hz, 1H), 4.73 (bs, 1H), 4.34 (q, J=7 Hz, 2H), 3.68 (m, 2H), 3.36 (m, 2H), 2.31 (s, 1H), 1.78 (s, 2H), 1.40 (s, 9H), 1.36 (t, J=7 Hz, 3H).

B.

7-([1α,5α,6α]-6-Amino-3-azabicvc-lo[3.1.0]hex-3-yl)-6-fluoro-1-(2,4-difluorophenyl)-1,4-dihydro-4-oxo-quinoline-3-carboxylic acid, mesylate salt A suspension of the compound of Example 13.A (400 mg, 0.73 mmol) in dioxane (25 ml) and water (25 ml) was treated with methanesulfonic acid (0.25 ml, 3.8 mmol) and heated at 100° C. for 18 hours. Solvents were removed in vacuo, and the residue was dissolved in acetone, treated with decolorizing charcoal, and filtered through Celite. Treatment of the filtrate with ether provided the title product as a pale green powder, mp 256° C. (decomp.) (108 mg, 0.22 mmol, 30% yield).

$^1$H NMR (MeOD-d$_4$/D$_2$O): 8.62 (s, 1H), 7.85 (d, J=13 Hz, 1H), 7.71 (m, 1H), 7.35 (m, 2H), 5.90 (m, 1H), 3.74 (m, 2H), 3.47 (m, 2H), 2.45 (bs, 1H), 2.13 (s, 2H).

EXAMPLE 14

A. 10-[(1α,5α,6α)-6-tert Butoxycarbonylamino-3-azabicyclo[3.1.0]hex-3-yl]-9-fluoro-2,3-dihydro-3-methyl-7-oxo-7H-pyrido[1,2,3-de]-1,4-benzoxazine-6-carboxylic acid A solution of [1α,5α,6α]-6-tert-butoxycarbonylamino-3-azabicyclo[3.1.0]hexane (75 mg, 0.38 mmol) and 9,10-difluoro-2,3-dihydro-3-methyl-7-oxo-7H-pyrido[1,2,3-de]-1,4-benzoxazine-6-carboxylic acid (100 mg, 0.36 mmol) in dimethylsulfoxide (6 ml) and triethylamine (1 ml) was heated at 80° C. for 72 hours. Solvent was removed in vacuo, and the residue was partitioned between chloroform and water. The organic layer was dried over sodium sulfate, filtered, and concentrated in vacuo, to give a yellow powder. This was further purified by column chromatography (eluant: 50:50:1 chloroform: methanol: concentrated ammonium hydroxide), supplying the title product as a yellow solid, mp 170°-173° C. (decomp.) (98 mg, 0.21 mmol, 59% yield).

$^1$H NMR (CDCl$_3$): 8.60 (s, 1H), 7.68 (d, J=13 Hz, 1H), 4.77 (bs, 1H), 4.48 (m, 2H), 4.33 (bd, J=12 Hz, 1H), 3.96 (m, 2H), 3.71 (m, 2H), 2.64 (bs, 1H), 1.77 (s, 2H), 1.62 (d, J=7 Hz, 3H), 1.48 (s, 9H).

B.

10-[(1α,5α,6α)-6-Amino-3-azabicyclo[3.1.0]hex-3-yl]-9-fluoro-2,3-dihydro-3-methyl-7-oxo-7H-pyrido[1,2,3-de]-1,4-benzoxazine-6-carboxylic acid, hydrochloride salt A solution of the compound of Example 14.A (85 mg, 0.19 mmol) in 6N hydrochloric acid (5 ml) was allowed to stir at room temperature for 2 hours. After the solvent was removed in vacuo, the residue was recrystallized from acetonitrile-methanol-ether to provide the title product as a solid, mp 186°-188° C. (decomp.) (48 mg, 0.12 mmol, 63% yield).

$^1$H NMR (D$_2$O): 8.62 (s, 1H), 7.07 (d, J=13.3 Hz, 1H), 4.55 (bd, J=11 Hz, 1H), 4.38 (bd, J=10 Hz, 1H), 3.96 (dd, J=14.2, 9.8 Hz, 2H), 3.69 (dd, apparent t, J=10 Hz, 2H), 2.77 (s, 1H), 2.09 (s, 2H), 1.57 (d, J=6.8 Hz, 3H).

EXAMPLE 15

A.

7-(1α,5α,6α]-6-tert-Butoxycarbonylamino-3-azabicyclo[3.1.0]hex-3-yl)-5-amino-1-cyclopropyl-6,8-difluoro-1,4-dihydro-4-oxo-quinoline-3-carboxylic acid A suspension of [1α,5α,6α]-6-tert-butoxycarbonylamino-3-azabicyclo[3.1.0]hexane (115 mg, 0.58 mmol) and 5-amino-1-cyclopropyl-6,7,8-trifluoro-1,4-dihydro-4-oxo-quinoline-3-carboxylic acid (125 mg, 0.42 mmol) in dimethylsulfoxide (3 ml) and triethylamine (0.3 ml) was heated at 80° C. for 19 hours. Solvent was removed in vacuo, and the residue partitioned between methylene chloride and water. The organic layer was washed with saturated aqueous sodium chloride solution, dried over sodium sulfate, filtered and concentrated to provide the title product (146 mg, 0.31 mmol, 74% yield).

$^1$H NMR (CDCl$_3$): 8.58 (s, 1H), 4.71 (bs, 1H), 3 90 (m, 3H), 3.69 (d, J=9.8 Hz, 2H), 2.52 (s, 1H), 1.75 (s, 2H), 1.43 (s, 9H), 1.15 (m, 2H), 1.00 (bs, 2H).

B.

7-([1α,5α,6α]-6-Amino-3-azabicyclo[3.1.0]hex-3-yl)-5-amino-1-cyclopropyl-6,8-difluoro-1,4-dihydro-4-oxo-quinoline-3-carboxylic acid, methanesulfonic acid salt A solution of the compound of Example 15.A (135 mg, 0.28 mmol) and methanesulfonic acid (28 μl, 0.41 mmol) in dioxane (20 ml) and water (20 ml) was heated to 100° C. for 18 hours. After removal of solvent, the residue was dissolved in methanol and isopropanol, treated with decolorizing charcoal, and filtered through Celite. The resulting filtrate was partially concentrated in vacuo; a powder formed, which was collected by filtration to provide the title product, mp,>275° C. (57 mg, 0.12 mmol, 43% yield).

$^1$H NMR (MeOD-d$_4$): 8.52 (s, 1H), 3.96 (m, 1H), 3.94 (d, J=10.5 Hz, 2H), 3.71 (d, J=9.7 Hz, 2H), 2.68 (s, 3H), 2.04 (s, 2H), 1.15 (m, 2H), 1.09 (bs, 2H).

EXAMPLE 16

A.

7-([1α,2β,5α,6α]-6-tert-Butoxycarbonylamino-2-methyl-3azabicyclo[3.1.0]hex-3-yl)-6-fluoro-1-(2,4-difluorophenyl)-1,4-dihydro-4-oxo-1,8-naphthyridine-3-carboxylic acid, ethyl ester A solution of [1,6-6-tert-butoxycarbonyl-amino-2-methyl-3-azabicyclo-3.1.0]hexane (370 mg, 1.74 mmol) and the ethyl ester of 7-chloro-6-fluor-1-(2,4difluorophenyl)-1,4-dihydro-4-oxo-1,8-naphthyridine-3-carboxylic acid ethyl ester (600 mg, 1.57 mmol) in acetonitrile (50 ml) and triethylamine (5 ml) was heated at reflux for 18 hours. Solvent was removed in vacuo, and the residue subjected to column chromatography (eluant: chloroform) to provide the title product as an oil (345 mg, 0.62 mmol, 39% yield).

$^1$H NMR (CDCl$_3$), mixture of rotamers: 8.35 and 8.33 (s, 1H), 8.03 and 8.01 (d, J=12.5 Hz, 1H), 7.38 (m, 1H), 7.02 (m, 2H), 4.73 (bs, 1H), 4.33 (q, J=7 Hz, 2H), 3.99 (m, 2H), 3.58 (m, 1H), 2.39 (s, 1H), 1.77 (m, 2H), 1.40 (s, 9H), 1 34 (t, J=7.4 Hz, 3H), 1.00 and 0.88 (d, J=5.7 Hz, 3H).

B.

7-([1α,2β,5α,6α]-6-Amino-2-methyl-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonic acid salt A solution of the compound of Example 16.A (0.30 g, 0.53 mmol) and methanesulfonic acid (0.10 ml, 1.53 mmol) in acetonitrile (30 ml) and water (15 ml) was heated to reflux for 24 hours. Solvents were removed in vacuo, and the residue recrystallized from methanol-acetonitrile, and then isopropanol-ether to give the title product as a white solid, mp>275° C. (darkening at 208° C.) (56 mg, 0.11 mmol, 21% yield).

$^1$H NMR (DMSO-d$_6$, 87° C.): 8.79 (s, 1H), 8.11 (d, J=12.6 Hz, 1H), 7.79 (dt, J=5.9, 8.7 Hz, 1H), 7.52 (ddd, J=10.3, 9.0, 2.7 Hz, 1H), 7.33 (m, 1H), 4.10 (m, 1H), 3.96 (dd, J=11, 5 Hz, 1H), 3.83 (m, 1H), 2.58 (m, 1H), 2.34 (s, 3H), 2.15 (m, 2H), 0.96 (m, 3H).

EXAMPLE 17

A.

7-([1,2,5,6]-6-tert-Butoxycarbonylamino-2-methyl-3azabicyclo[3.1.0]hex-3-yl)-1-cyclopropyl-6-fluoro-1,4-dihydro-4-oxo-quinoline-3-carboxylic acid A solution of [1α,2β,5α,6α]-6-tert-butoxycarbonylamino-2-methyl-3-azabicyclo[3.1.0]hexane (135 mg, 0.64 mmol) and 1-cyclopropyl-6,7-difluoro-1,4-dihydro-4-oxo-quinoline-3-carboxylic acid (120 mg, 0.45 mmol) in dimethylsulfoxide (5 ml) and triethylamine (0.5 ml) was heated at 80° C. for 18 hours. Solvent was removed in vacuo and the residue was dissolved in ethyl acetate (100 ml), treated with decolorizing charcoal, filtered through Celite, and concentrated in vacuo. The resulting solid was recrystallized from ethyl acetate-ether to provide the title product, mp 214°–216° C. (decomp) (137 mg, 0.30 mmol, 67% yield).

$^1$H NMR (CDCl$_3$): 8.70 (s, 1H), 7.94 (d, J=13.5 Hz, 1H), 7.08 (d, J=7.3 Hz, 1H), 4.73 (bs, 1H), 4.21 (m, 2H), 3.44 (m, 2H), 2.61 (s, 1H), 1.98 (m, 1H), 1.85 (m, 1H), 1.44 (s, 9H), 1.36 (d, J=5.6 Hz, 3H), 1.32 (m, 1H), 1.20 (m, 2H), 1.13 (m, 1H).

B.

7-([1α,2β,5α,6α]-6-Amino-2-methyl-3-azabicyclo[3.1.0]hex-3-yl)-1-cyclopropyl-6-fluoro-1,4-dihydro-4-oxo-quinoline-3-carboxylic acid, methanesulfonic acid salt A suspension of the compound of Example 17.A (130 mg, 0.28 mmol) and methanesulfonic acid (0.03 ml, 0.44 mmol) in acetonitrile (10 ml) and water (10 ml) was heated to reflux for 18 hours. After removal of solvent in vacuo, the residue was recrystallized from isopropanol-methanol to provide the title product as a white solid, mp>275° C. (38 mg, 0.084 mmol, 30% yield). $^1$H NMR (DMSO-d$_6$): 8.65 (s, 1H), 8.14 (bs, 1H), 7.89 (d, J=13.4 Hz, 1H), 7.33 (d, J=7.7 Hz, 1H), 4.29 (m, 1H), 4.08 (m, 1H), 3.78 (m, 1H), 3.42 (m, 1H), 2.71 (s, 1H), 2.29 (s, 3H), 2.23 (m, 1H), 2.10 (m, 1H), 1.29 (d, J=5.5 Hz, 3H), 1.25 (m, 3H), 1.11 (m, 1H).

EXAMPLE 18

A.
7-([1α,2β,5α,6α]-6-tert-Butoxycarbonylamino-2-methyl-3azabicyclo[3.1.0]hex-3-yl)-5-amino-1-cyclopropyl-6,8-difluoro-1,4-dihydro-4-oxo-quinoline.-3-carboxylic acid A suspension of [1α,2β,5α,6α]-6-tert-butoxycarbonyl-amino-2-methyl-3-azabicyclo[3.1.0]hexane (65 mg, 0.31 mmol) and 5-amino-1-cyclopropyl-6,7,8-trifluoro-1,4-dihydro-4-oxo-quinoline-3-carboxylic acid (80 mg, 0.27 mmol) in dimethylsulfoxide (1 ml) and triethylamine (0.1 ml) was heated at 85° C. for 18 hours. Additional 3-azabicyclo-[3.1.0]hexane (10 mg, 0.047 mmol) was added, and heating was continued for 16 hours. Solvent was removed in vacuo, and the residue partitioned between chloroform and water. The organic layer was washed with saturated aqueous sodium chloride solution, dried over sodium sulfate, filtered and concentrated to provide the title product (51 mg, 0.10 mmol, 37% yield).

$^1$H NMR (CDCl$_3$): 8.62 (s, 1H), 6.44 (vbs, 2H), 4.66 (bs, 1H), 4.30 (m, 1H), 3.94 (m, 2H), 3.31 (dd, J=9.2, 3.6 Hz, 1H), 2.70 (s, 1H), 1.72 (m, 2H), 1.44 (s, 9H), 1.19 (m, H), 1.16 (d,J=5.9 Hz, 3H), 0.98 (m, 1H).

B.
7-([1α,2β,5α,6α]-6-Amino-2-methyl-3-azabicyclo-[3.1.0]hex-3-yl)-5-amino-1-cyclopropyl-6,8-difluoro-1,4-dihydro-4-oxo-quinoline-3-carboxylic acid, methanesulfonic acid salt A solution of the compound of Example 18.A (48 mg, 0.098 mmol) and methanesulfonic acid (15 μl, 0.21 mmol) in dioxane (3 ml) and water (3 ml) was heated to 100° C. for 24 hours. After removal of solvent, the residue was triturated with isopropanol to provide the title product as a solid, mp>275° C. (32 mg, 0.066 mmol, 67% yield).

$^1$H NMR/(DMSO-d$_6$): 8.52 (s, 1H), 8.11 (m, 2H), 4.20 (m, 1H), 4.02 (m, 1H), 3.79 (d, J=9.6 Hz, 1H), 3.36 (m, 1H), 2.61 (bs, 1H), 2.31 (s, 3H), 2.05 (m, 1H), 1.98 (m, 1H), 1.11 (m, 5H), 1.02 (m, 2H).

EXAMPLE 19

A.
7-([1α,2β,5α]-1-tert-Butoxycarbonylamino-2-methyl-3azabicyclo[3.1.0]hex-3-yl)-6-fluoro-1-(2,4-difluorophenyl)-1,4-dihydro-4-oxo-1,8-naphthyridine-3-carboxylic acid, ethyl ester A solution of [1α,2β,5α]-1-tert-butoxycarbonylamino-2-methyl-3-azabicyclo[3.1.0]hexane (122 mg, 0.57 mmol) and the ethyl ester of 7-chloro-6-fluoro-1-(2,4-difluorophenyl)-1,4-dihydro-4-oxo-1,8-naphthyridine-3-carboxylic acid ethyl ester (208 mg, 0.54 mmol) in dimethylsulfoxide (3 ml) and triethylamine (0.3 ml) was heated to 85° C. for 3.5 hours. Solvent was removed in vacuo, and the residue was partitioned between chloroform and water. The organic layer was dried over sodium sulfate and concentrated; the resulting material was purified by column chromatography (eluant: chloroform) to provide the title product as a white solid, mp 254° C. (with decomposition) (217 mg, 0.39 mmol, 72% yield).

$^1$H NMR (CDCl$_3$): 8.33 (m, 1H), 8.05 (bd, J=12 Hz, 1H), 7.30 (m, 1H), 6.99 (m, 2H), 4.90 (bs, 1H), 4.37 (q, J=7 Hz, 2H), 3.90 (m, 1H), 3.73 (m, 1H), 1.81 (m, 1H), 1.43 (s, 9H), 1.40 (t, J=7 Hz, 3H), 0.88 (m, 2H).

B.
7-([1α,2β,5α]-1-Amino-2-methyl-3-azabicyclo-[3.1.0]hex-3-yl)-6-fluoro-1-(2,4-difluorophenyl)-1,4-dihydro-4-oxo-1,8-naphthyridine-3-carboxylic acid, methanesulfonic acid salt A solution of the compound of Example 19.A (190 mg, 0.34 mmol) and methanesulfonic acid (50 μl, 0.73 mmol) in dioxane (10 ml) and water (10 ml) was heated to reflux for 19 hours. Solvents were removed in vacuo, and the residue was dissolved in methanol-isopropanol, and treated with decolorizing charcoal. Concentration in vacuo provided the title product as a solid, mp>275° C. (59 mg, 0.14 mmol, 40% yield).

$^1$H NMR (DMSO-d$_6$), mixture of rotamers: 8.91 and 8.87 (s, 1H), 8.19 and 8.18 (d, J=12.5 Hz, 1H), 7.83 (m, 1H), 7.60 (m, 1H), 7.37 (m, 1H), 3.99 (m, 1H), 3.86 (m, 2H), 2.30 (s, 3H), 2.08 (m, 1H), 1.18 (m, 1H), 1.05 and 0.88 (d, J=6.0 Hz, 3H), 0.96 (m, 3H).

EXAMPLE 20

A.
7-([1α,2β,5α]-1-tert-Butoxycarbonylamino-2-methyl-3azabicyclo[3.1.0]hex-3-yl)-1-cyclopropyl-6-fluoro-1,4-dihdro-4-oxo-1,8-naphthvridine-3-carboxylic acid, ethyl ester A suspension of [1α,2β,5α]-1-tert-butoxycarbonyl-amino-2-methyl-3-azabicyclo[3.1.0]hexane (130 mg, 0.61 mmol) and the ethyl ester of 7-chloro-1-cyclopropyl-6-fluoro-1,4-dihydro-4-oxo-1,8-naphthyridine-3-carboxylic acid ethyl ester (180 mg, 0.58 mmol) in dimethylsulfoxide (3.5 ml) and triethylamine (0.3 ml) was heated to 80° C. for 26 hours. Solvent was removed in vacuo, and the residue was chromatographed (eluant: chloroform), and then recrystallized from ether. The title product was obtained as a yellow solid, mp 181°-183° C. (96 mg, 0.20 mm©l, 34% yield).

$^1$H NMR (CDCl$_3$): 8.48 (s, 1H), 8.06 (d, J=12.3 Hz, 1H), 5.06 (bs, 1H), 4.42 (q, J=5.9 Hz, 1H), 4.36 (q, J=7 Hz, 2H), 4.08 (dd, J=10.4, 5.5 Hz, 1H), 3.84 (m, 1H), 3.49 (m, 1H), 1.92 (m, 1H), 1.42 (s, 9H), 1.40 (m, 6H), 1.18 (m, 2H), 1.03 (m, 4H).

B.
7-([1α,2β,5α]-1-Amino-2-methyl-3-azabicyclo-[3.1.0]hex-3-1)-1-cyclopropyl-6-fluoro-1,4-dihydro-4-oxo-1,8-naphthyridine-3-carboxylic acid, methanesulfonic acid salt A solution of the compound of Example 20.A (80 mg, 0.16 mmol) and methanesulfonic acid (11Ll, 0.17 mmol) in dioxane (10 ml) and water (10 ml) was heated to reflux for 42 hours. Solvents were removed in vaouo, and the residue was triturated with acetone, then recrystallized from isopropanol-methanol. The title product was obtained as a solid, mp>275° C. (33 mg, 0.073 mmol, 46% yield).

$^1$H NMR (DMSO-d$_6$): 8.64 (s, 1H), 8.13 (d, J=13.0 Hz, 1H), 4.64 (bq, J=5.9 Hz, 1H), 3.97 (m, 2H), 3.72 (m, 1H), 2.30 (s, 3H), 2.17 (m, 1H), 1.50 (d, J=5.9 Hz, 3H), 1.16 (m, 6H).

EXAMPLE 21

A.

7-([1α,2β,5α]-1-[(N-Acetyl)aminomethyl]-2-methyl-3-azabicclo[3.1.0]hex-3-yl)-6-fluoro-1-(2,4-difluorophenyl)-1,4-dihydro-4-oxo-1,8-naphthyridine-3-carboxylic acid, ethyl ester A mixture of [1α,2β,5α]-1-[(N-acetyl)aminomethyl]-2-methyl-3-azabicyclo[3.1.0]hexane (101 mg, 0.60 mmol) and triethylamine (0.25 ml, 1.8 mmol) in acetonitrile (15 ml) was treated with the ethyl ester of 7-chloro-6-fluoro-1-(2,4-difluorophenyl)-1,4-dihydro-4-oxo-1,8-naphthyridine-3-carboxylic acid (206 mg, 1.8 mmol) and heated to 80° C. for 24 hours. The reaction mixture was concentrated in vacuo, and chromatographed on a Chromatotron using a silica gel plate (eluant: 89:10:1 chloroform: methanol: concentrated ammonium hydroxide) to provide the title product (244 mg, 0.47 mmol, 87% yield).

$^1$H NMR (CDCl$_3$, mixture of rotamers): 8.40 and 8.36 (s, 1H), 7.96 (bd, J=12.4 Hz, 1H), 7.23 (m, 3H), 5.91 (bs, 1H), 4.34 (q, J=7 Hz, 2H), 3.86 (m, 2H), 3.71 (m, 1H), 3.57 (m, 1H), 3.20 and 2.96 (m, 1H), 2.03 and 1.97 (s, 3H), 1.54 (m, 1H), 1.36 (t, J=7 Hz, 3H), 0.90 and 0.74 (d, J=5.7 Hz, 3H), 0.67 (m, 1H), 0.57 (m, 1H).

A.

7-([1α,2β,5α]-1-Aminomethyl]-2-methyl-3-azabicyclo-[3.1.hex-3-yl)-6-fluoro-1-(2,4-difluorophenyl)-1,4-dihydro-4-oxo-1,8-naphthyridine-3-carboxylic acid, hydrochloride salt The compound of Example 21.A (232 mg, 0.45 mmol) was mixed with hydrochloric acid (3 ml of a 6N solution) and acetic acid (3 ml) and heated to 100° C. for 7 days. The reaction mixture was then concentrated in vacuo and the residue was triturated with isopropanol to provide the title product as a cream-colored solid, mp 239° C. with decomposition (90.1 mg, 0.19 mmol, 42% yield).

$^1$H NMR (DMSO-d$_6$, 87° C.): 8.75 (s, 1H), 8.09 (d, J=12.9 Hz, 1H), 7.80 (m, 1H), 7.52 (m, 1H), 7.33 (m, 1H), 4.14 (m, 1H), 3.85 (dd, J=11.0, 4.8 Hz, 1H), 3.75 (m, 1H), 3.21 (d, J=13.9 Hz, 1H), 2.79 (d, J=13.9 Hz, 1H), 1.94 (m, 1H), 0.98 (d, J=5.8 Hz, 3H), 0.91 (dd, J=8.4, 5.4 Hz, 1H), 0.72 (dd, apparent t, J=4.9 Hz, 1H).

EXAMPLE 22

A.

7-([1α,5α,6α]-6-[(N-tert-Butoxycarbonyl)aminomethyl]-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester A mixture of [1α,5α,6α]-6-[N-tert-butoxycarbonyl)-aminomethyl]-3-azabicyclo[3.1.0]hexane (307 mg, 1.45 mmol) and triethylamine (8 ml) in acetonitrile (40 ml) was treated with the ethyl ester of 7-chloro-6-fluoro-1-(2,4-difluorophenyl)-1,4-dihydro-4-oxo-1,8-naphthyridine-3-carboxylic acid (525 mg, 1.37 mmol) and heated to 80° C. for 18 hours. The solvent was removed in vacuo, and the residue was partitioned between ethyl acetate and water. The organic layer was washed with saturated sodium chloride solution, dried over sodium sulfate, filtered and concentrated in vacuo. The resulting material was purified by chromatography on silica gel (eluant: chloroform) to provide the title product as a foam (608 mg, 1.12 mmol, 77% yield).

$^1$H NMR (CDCl$_3$): 8.32 (s, 1H), 8.00 (d, J=12.9 Hz, 1H), 7.37 (m, 1H), 7.03 (m, 2H), 4.66 (bs, 1H), 4.33 (q, J=7 Hz, 2H), 3.69 (m, 2H), 3.45 (m, 2H), 3.02 (m, 2H), 1.49 (s, 2H), 1.40 (s, 9H), 1.35 (t, J=7 Hz, 3H), 0.77 (m, 1H).

B.

7-([1α,5α,6α]-6-Aminomethyl-3-azabicyclo[3.1.0]-hex-3-yl)-6-fluoro-1-(2,4-difluorophenyl)-1,4-dihydro-4-oxo-1,8-nahthyridine-3-carboxylic acid, hydrochloride salt The compound of Example 22.A (600 mg, 1.1 mmol) was treated with hydrochloric acid (25 ml of a 6N solution) and heated to reflux for 18 hours. Removal of solvent provided a solid, which was recrystallized from methanol and washed with ether to provide the title product as a white solid, mp>275° C. (186 mg, 0.398 mmol, 36% yield).

$^1$H NMR (D$_2$O, 87° C.): 9.40 (s, 1H), 8.63 (d, J=12.8 Hz, 1H), 8.24 (m, 1H), 7.94 (m, 2H), 4.48 (m, 2H), 4.28 (m, 2H), 3.66 (d, J=7.2 Hz, 2H), 2.45 (s, 2H), 1.59 (s, 1H).

EXAMPLE 23

A.

7-([1α,5α,6α]-6-[(N-tert-Butoxycarbonyl)aminomethyl]-3-azabicyclo[3.1.0]hex-3-yl)-1-cyclopropyl-6-fluoro-1,4-dihydro-4-oxo-quinoline-3-carboxylic acid, ethyl ester

[1α,5α,6α]-6-[(N-tert-Butoxycarbonyl)aminomethyl]-3-azabicyclo[3.1.0]hexane (350 mg, 1.6 mmol) in dimethylsulfoxide 8 ml) and triethylamine (1 ml) was treated with the ethyl ester of 1-cyclopropyl-6,7-difluoro-1,4-dihydro-4-oxo-quinoline-3-carboxylic acid (352 mg, 1.2 mmol) as in Example 22.A to provide the title product as a solid, mp 35°-137° C. (296 mg, 0.61 mmol, 51% yield). $^1$H NMR (CDCl$_3$) 8.43 (s, 1H), 7.93 (d, J=14.9 Hz, 1H), 6.79 (d, J=7.3 Hz, 1H), 4.69 (bs, 1H), 4.35 (q, J=6.8 Hz, 2H), 3.82 (dd, J=9.9, 2.9 Hz, 2H), 3.48 (m, 2H), 3.32 (m, 1H), 3.08 (m, 2H), 1.61 (s, 2H), 1.43 (s, 9H), 1.37 (t, J=7 Hz, 3H), 1.25 (m, 2H), 1.08 (m, 2H), 1.00 (m, 1H).

B.

7-([1α,5α,6α]-6-Aminomethyl-3-azabicyclo[3.1.0]-hex-3-yl)-1-cyclopropyl-6-fluoro-1,4-dihydro-4-oxo-quinoline-3-carboxylic acid, hydrochloric acid The compound of Example 23.A (225 mg, 0.46 mmol) was converted by the method of Example 22.B to provide the title product as a yellow solid, mp>275° C. (146 mg, 0.39 mmol, 85% yield).

$^1$H NMR (MeOD-d$_4$): 8.57 (s, 1H), 7.66 (d, J=14.7 Hz, 1H), 7.05 (d, J=7.7 Hz, 1H), 3.96 (bd, J=7 Hz, 2H), 3.69 (bd, J=9 Hz, 2H), 2.97 (d, J=7.6 Hz, 2H), 1.92 (s, 2H), 1.39 (m, 2H), 1.20 (m, 3H).

EXAMPLE 24

A.

10-[(1α,5α,6α]-6-(N-tert-Butoxycarbonyl]aminomethyl-3-azabicyclo[3.1.0]hex-3-yl)-9-fluoro-2,3-dihydro-3-methyl-7-oxo-7H-pyrido[1,2,3-de]-1,4-benzoxazine-6-carboxylic acid A mixture of [1α,5α,6α]-6-([N-tert-butoxycarbonyl]-aminomethyl)-3-azabicyclo[3.1.0]hexane (300 mg, 1.5 mmol) and 9,10-difluoro-2,3-dihydro-3-methyl-7-oxo-7H-pyrido -[1,2,3-de]-1,4-benzoxazine-6-carboxylic acid (260 mg, 0.92 mmol) in dimethylsulfoxide (5 ml) and triethylamine (1 ml) was treated as in Example 22.A to provide the title product (96 mg, 0.22 mmol, 24% yield).

¹H NMR (CDCl₃) 8.54 (s, 1H), 7.67 (d, J=13.1 Hz, 1H), 4.60 (bs, 1H), 4.41 (m, 2H), 4.28 (m, 1H), 3.80 (m, 2H), 3.63 (m, 2H), 3.08 (m, 2H), 1.58 (d, J=6.4 Hz, 3H), 1.54 (s, 2H), 1.43 (s, 9H), 1.10 (m, 1H).

B.
10-[(1-,5,6]-6-Aminomethyl-3-azabicyclo[3.1.0]-hex-3-yl]-9-fluoro-2,3-dihydro-3-methyl-7-oxo-7H-pyrido[1,2,3-de]-1,4-benzoxazine-6-carboxylic acid, methanesulfonic acid salt A suspension of the compound of Example 24.A (80 mg, 0.17 mmol) in acetone (2.5 ml) and water (2.5 ml) was treated with methanesulfonic acid (0.10 ml, 1.5 mmol) and heated on a steam bath for 1.5 hours. Solvents were removed in vacuo, and the residue was triturated with acetone to provide the title product as a yellow solid, mp 276° C. with decomposition (38 mg, 0.08 mmol, 47% yield).

¹H NMR (D₂O): 8.66 (s, 1H), 7.18 (d, J=13.6 Hz, 1H), 4.78 (m, 1H), 4.57 (m, 1H), 4.37 (m, 1H), 3.91 (m, 2H), 3.67 (m, 2H), 3.03 (d, J=7.3 Hz, 2H), 2.82 (s, 3H), 1.73 (s, 2H), 1.58 (d, J=6.1 Hz, 3H), 1.27 (m, 1H).

EXAMPLE 25

A.
7-([1α,5α,6α]-6-[(N-tert-Butoxycarbonyl)aminomethyl]-3-azabicyclo-[3.1.0]hex-3-yl)-6-fluoro-1-(2,4-difluorophenyl)-1,4-dihydro-4-oxo-quinoline-3-carboxylic acid, ethyl ester

[1α,5α,6α]-6-[(N-tert-Butoxycarbonyl)aminomethyl]-3-azabicyclo[3.1.0]hexane (225 mg, 1.06 mmol) in dimethyl- sulfoxide (5 ml) and triethylamine (1 ml) was treated with the ethyl ester of 1-cyclopropyl-6,7-difluoro-1,4-dihydro-4-oxo-quinoline-3-carboxylic acid (365 mg, 1.0 mmol) as in Example 22.A to provide the title product as a foam (226 mg, 0.406 mmol, 41% yield).

¹H NMR (CDCl₃) 8.22 (s, 1H), 7.96 (d, J=13 Hz, 1H), 7.45 (m, 1H), 7.12 (m, 2H), 5.67 (bd, J=7 Hz, 1H), 4.60 (bs, 1H), 4.37 (q, J=7 Hz, 2H), 3.60 (m, 2H), 3.32 (m, 2H), 3.05 (m, 2H), 1.55 (s, 2H), 1.45 (s, 9H), 1.40 (t, J=7 Hz, 3H), 0.92 (m, 1H).

B.
7-[(1α,5α,6α]-6-Aminomethyl-3-azabicyclo[3.1.0]-hex-3-yl]-6-fluoro-1-(2,4-difluorophenyl)-1,4-dihydro-4-oxo-quinoline-3-carboxylic acid methanesulfonic acid salt The compound of Example 25.A (200 mg, 0.35 mmol) was treated with methanesulfonic acid (95 1, 1.43 mmol) as in Example 24.B to provide the title product as a yellow powder, mp 255° C. with decomposition (82 mg, 0.16 mmol, 44% yield).

¹H NMR (D₂O, 97° C.): 9.43 (s, 1H), 8.47 (m, 2H), 8.16 (m, 2H), 6.64 (m, 1H), 4.39 (m, 2H), 4.24 (m, 2H), 3.79 (m, 2H), 3.57 (s, 3H), 2.60 (s, 2H), 1.80 (m, 1H).

EXAMPLE 26

A. 7-([1α,5α,6α]-6-[(N-tert-Butoxycarbonyl)amino -methyl]-2-methyl-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester A mixture of [1α,2β,5α,6α]-6-[(M-tert-butoxycarbonyl) -aminomethyl]-2-methyl-3-azabicyclo[3.1.0]hexane (400 mg, 1.75 mmol) and triethylamine (5 ml) in acetonitrile (50 ml) was treated with the ethyl ester of 7-chloro-6-fluoro-1-(2,4-difluorophenyl)-1,4-dihydro-4-oxo-1,8-naphthyridine-3-carboxylic acid (625 mg, 1.63 mmol) by the method of Example 22.A to provide the title product (687 mg, 1.2 mmol, 74% yield).

¹H NMR (CDCl₃, mixture of rotamers): 8.35 and 8.34 (s, 1H), 8.04 and 8.02 (d, J=12.5 Hz, 1H), 7.38 (m, 1H), 7.03 (m, 2H), 4.63 (bs, 1H), 4.33 (q, J=7 Hz, 2H), 3.95 (m, 2H), 3.53 (m, 1H), 2.99 (m, 2H), 1.55 (m, 2H), 1.41 (s, 9H), 1.35 (t, J=7 Hz, 3H), 0.94 (m, 1H), 0.91 and 0.79 (d, J=5.9 Hz, 3H).

B.
7-[(1α,5α,6α]-6-Aminomethyl-2-methyl-3-azabicyclo-[3.1.0]hex-3-yl)-6-fluoro-1-(2,4-difluorophenyl)dihydro-4-oxo-1,8-naphthyridine-3-carboxylic acid, hydrochloride salt The compound of Example 26.A (650 mg, 1.13 mmol) was converted as in Example 22.B to provide the title product (78 mg, 0.16 mmol, 14% yield).

¹H NMR ((MeOD-d₄, mixture of rotamers): 8.73 and 8.71 (s, 1H), 8.00 (d, J=12 Hz, 1H), 7.57 (m, 1H), 7.22 (m, 2H), 4.02 (m, 2H), 3.70 (m, 1H), 2.87 (m, 2H), 1.83 (m, 2H), 1.11 (m, 1H), 0.96 and 0.85 (d, J=6 Hz, 3H).

EXAMPLE 27

A.
7-([1α,5α,6α]-6-tert-Butoxycarbonvlamino-3-azabicyclo-[3.1.0]hex-3-yl)-1-cyclopropyl-6-fluoro-1,4-dihydro-4-oxo-quinoline-3-carboxylic acid, ethyl ester A suspension of [1α,5α,6α]-6-tert-butoxycarbonylamino-3-azabicyclo[3.1.0]hexane (275 mg, 1.38 mmol) and 1-cyclopropyl-6,7-difluoro-1,4-dihydro-4-oxo-quinoline-3-carboxylic acid (335 mg, 1.14 mmol) in dimethylsulfoxide (10 ml) and triethylamine (2 ml) was treated as in Example 22.A to provide the title product as a solid, mp 202°-204° C. (261 mg, 0.625 mmol, 55% yield).

¹H NMR (CDCl₃) 8.44 (s, 1H), 7.93 (d, J=13 Hz, 1H), 6.78 (d, J=6 Hz, 1H), 4.80 (bs, 1H), 4.40 (q, J=7 Hz, 2H), 3.91 (m, 2H), 3.55 (bd, J=8 Hz, 2H), 3.31 (m, 1H), 2.45 (s, 1H), 1.88 (s, 2H), 1.45 (s, 9H), 1.39 (t, J=7 Hz, 3H), 1.25 (m, 2H), 1.09 (m, 2H).

B.
7-[(1α,5α,6α]-6-Amino-3-azabicyclo[3.1.0]hex-3-yl)-1-cyclopropyl-6-fluoro-1,4-dihydro-4-oxo-quinoline-3-carboxylic acid, hydrochloride salt The compound of Example 27.A (200 mg, 0.48 mmol) was treated as in Example 22.B to provide the title product as a solid, mp 202°-204° C. with decomposition (64.6 mg, 0.17 mmol, 35% yield).

¹H NMR (D₂0, 87° C.): 9.23 (s, 1H), 8.08 (d, J=14.5 Hz, 1H), 7.59 (d, J=7.5 Hz, 1H), 4.62 (dd, J=10.6, 2.9 Hz, 2H), 4.37 (bd, J=10.7 Hz, 2H), 4.25 (m, 1H), 3.38 (s, 1H), 3.01 (s, 2H), 2.09 (m, 2H), 1.81 (m, 2H).

EXAMPLE 28

A.
7-([1α,5α,6α]-1-tert-Butoxycarbonylamino-2-methyl-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester

[1α,2α,5α]-1-tert-Butoxycarbonylamino-2-methyl-3azabicyclo[3.1.0]hexane and 7-chloro-6-fluoro-1-(2,4-difluorophenyl)-1,4-dihydro-4-oxo-1,8-naphthyridine- 3-carboxylic acid ethyl ester were reacted and purified according to the procedure of Example 23.A to provide the title product as a solid, mp 181°–183° C. (72% yield).

¹H NMR (MeOH-d₄): 8.57 (s, 1H), 7.96 (bd, J=12.4 Hz, 1H), 7.63 (m, 1H), 7.26 (m, 2H), 4.3 (vbm, 1H), 4.28 (q, J=7.0 Hz, 2H), 3.8 (vbm, 2H), 1.72 (m, 1H), 1.42 (s, 9H), 1.31 (t, J=7.0 Hz, 3H), 0.98 (m, 4H), 0.65 (m, 1H).

B.
7-[(1α,2α,5α]-1-Amino-2-methyl-3-azabicclo[3.1.0]hex-3-yl)-6-fluoro-1-(2,4-difluorophenyl)-1,4-dihydro-4-oxo-1,8-naphthyridine-3-carboxylic acid, methane-sulfonic acid salt.

7-([1α,2α,5α]-1-tert-Butoxycarbonylamino-2-methyl-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester was hydrolyzed to the title product by the procedure of Example 25.B. The product was purified by recrystallization from acetone to provide a solid of mp>275° C. (82% yield).

¹H NMR (D₂O, 67° C.): 9.30 (s, 1H), 8.39 (d, J=12.4 Hz, 1H), 8.08 (m, 1H), 7.79 (m, 2H), 4.96 (m, 1H), 4.37 (m, 2H), 3.30 (s, 3H), 2.64 (m, 1H), 1.81 (m, 1H), 1.69 (bs, 3H), 1.33 (m, 1H).

EXAMPLE 29
A.
7-[(1α,5α,6α]-6-[(N-Methyl)tert-butoxycarbonylamino]-3-azabicyclo[3.1.0]hex-3-yl)-1-cyclopropyl-6-fluoro-1,4-dihydro-4-oxo-quinoline-3-carboxylic acid

[1α,5α,6α]-6-(N-Methyl)tert-butoxycarbonylamino-3-azabicyclo[3.1.0]hexane and 1-cyclopropyl-6,7-difluoro-1,4-dihydro-4-oxo-quinoline-3-carboxylic acid were reacted according to the procedure of Example 18.A. Purification was effected by recrystallization from ethyl acetate, to provide the title product as a solid, mp 253°–256° C. (40% yield).

¹H NMR (CDCl₃) 8.66 (s, 1H), 7.90 (d, J=14.3 Hz, 1H), 6.89 (d, J=7.3 Hz, 1H), 3.97 (m, 2H), 3.72 (bd, J=9.2 Hz, 2H), 3.48 (m, 1H, 2.89 (s, 3H), 2.43 (m, 1H), 2.05 (bs, 2H), 1.50 (s, 9H), 1.35 (m, 2H), 1.18 (m, 2H).

B.
7-[(1α,5α,6α]-6-[(N-Methyl)amino]-3-azabicyclo[3.1.0]hex-3-yl)-1-cyclopropyl-6-fluoro-1,4-dihydro-4-oxo-quinoline-3-carboxylic acid, methanesulfonic acid salt The compound of step A was hydrolyzed according to the procedure of Example 25.B. Recrystallization from isopropanol-methanol provided the title product as a solid, mp>275° C. (46% yield).

¹H NMR (DMSO-d₆): 8.75 (bs, 1H), 8.59 (s, 1H), 7.83 (d, J=14.5 Hz, 1H), 7.11 (d, J=7.7 Hz, 1H), 3.91 (m, 2H), 3.70 (m, 3H), 2.73 (s, 1H), 2.68 (s, 3H), 2.30 (s, 3H), 2.26 (s, 2H), 1.28 (m, 2H), 1.15 (m, 2H).

EXAMPLE 30
A.
7-[(1α,5α,6α]-6-[(N-MethYl}tert-butoxcarbonylamino]-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester

[1α,5α,6α]-6-(N-Methyl)tert-butoxycarbonylamino-3-azabicyclo[3.1.0]hexane and the ethyl ester of 7-chloro-6-fluoro-1-(2,4-difluorophenyl)-1,4-dihydro-4-oxo-1,8-naphthyridine-3-carboxylic acid were reacted according to the procedure of Example 22.A. After removal of the reaction solvents, purification was effected by recrystallization from ethyl acetate/ether, to provide the title product as a white solid, mp 171°–173° C. (84% yield).

¹H NMR (CDCl₃): 8.37 (s, 1H), 8.06 (d, J=12.7 Hz, 1H), 7.39 (m, 1H), 7.06 (m, 2H), 4.38 (q, J=7.1 Hz, 2H), 3.82 (vbm, 2H), 3.60 (vbm, 2H), 2.83 (s, 3H), 2.21 (m, 1H), 1.86 (bs, 2H), 1.45 (s, 9H), 1.39 (t, J=7.1 Hz, 3H).

B.
7-[(1α,5α,6α]-6-[(N-Methy)amino]-3-azabicyclo[3.1.0]-hex-3-yl)-6-fluoro-1-(2,4-difluorophenyl)-1,4-dihydro-4-oxo-1,8-naphthyridine-3-carboxylic acid, methanesulfonic acid salt The compound of step A was hydrolyzed according to the procedure of Example 25.B. Recrystallization from acetone-methanol provided the title product as an off-white powder, mp>275° C. (53% yield).

¹H NMR (D₂O, 77° C.): 9.35 (s, 1H), 8.35 (d, J=13 Hz, 1H), 8.15 (m, 2H), 7.90 (m, 2H), 4.45 (d, J=8 Hz, 2H), 4.25 (d, J=8 Hz, 2H), 3.45 (s, 3H), 3.40 (s, 3H), 3.20 (s, 1H), 2.90 (s, 2H).

EXAMPLE 31
A.
7-[(1α,5α,6α]-6-[tert-Butoxycarbonvlamino]-3-azabicyclo[3.1.0]hex-3-yl)-6-fluoro-1-(2,4-difluorophenyl)-1,4-dihydro-4-oxo-1,8-naphthyridine-3-carboxylic acid, ethyl ester 1α,5α,6α]-6-(tert-Butoxycarbonylamino)-3-azabicyclo-[3.1.0]hexane ad the ethyl ester of 7-chloro-6-fluoro-1-(2,4-difluorophenyl)-1,4-dihydro-4-oxo-1,8-naphthyridine-3-carboxylic acid were reacted according to the procedure of Example 22.A. After removal of the reaction solvents, the residue was partitioned between chloroform and water. The organic layer was dried over sodium sulfate, filtered and concentrated, to provide material which was then recrystallized from ethyl acetate to provide the title product as a white solid, mp>248° C. with decomposition (72% yield).

¹H NMR (CDCl₃) 8.33 (s, 1H), 8.00 (d, J=12.5 Hz, 1H), 7.36 (m, 1H), 7.02 (m, 2H), 4.51 (bs, 1H), 4.34 (q, J=7 Hz, 2H), 3.67 (bm, 2H), 3.56 (bm, 2H), 2.75 (m, 1H), 1.86 (bs, 2H), 1.36 (m, 12H).

B.
7-[(1α,2α,5α]-6-Amino-3-azabicyclo[3.1.0]hex-3-yl)-6-fluoro-1-2,4-difluorophenyl)-1,4-dihydro-4-oxo-1,8-naphthyridine-3-carboxylic acid, methanesulfonic acid salt The compound of step A was hydrolyzed according to the procedure of Example 25.B. The resulting powder was triturated with acetone to give a white powder, mp>275° C. (77% yield).

¹H NMR (D20-MeOH-d₄) 8.76 (s, 1H), 7.85 (d, J=12.0 Hz, 1H), 7.55 (m, 1H), 7.21 (m, 2H), 3.85 (m, 4H), 2.84 (t, J=7.4 Hz, 1H), 2.72 (s, 3H), 2.08 (bd, J=7.5 Hz, 2H).

EXAMPLE 32
A.
7-[(1α,5α,6α]-6-tert-Butoxycarbonylamino]-3-azabicyclo[3.1.0]hex-3-yl)-1-cyclopropyl-6-fluoro-1,4-dihydro-4-oxo-1,8-naphthyridine-3-carboxylic acid, ethyl ester 7-[(1α,5α,6α]-6-(tert-Butoxycarbonylamino)-3-azabicyclo-[3.1.0]hexane and the ethyl ester of 7-chloro- 1-cyclopropyl-6-fluoro-1,4-dihydro-4-oxo-1,8-naphthyridine-3-carboxylic acid were reacted according to the procedure of Example 22.A. After removal of the reaction solvents, the residue was partitioned between methylene chloride and water. The organic layer was dried over sodium sulfate, filtered and concentrated, to provide material which was then purified by chromatography (eluant: 5% methanol in chloroform) to provide the title product as a solid, mp 226°–228° C. with decomposition (94% yield).

$^1$H NMR (CDCl$_3$): 8.44 (s, 1H), 8.01 (d, J=12.8 Hz, 1H), 4.59 (bs, 1H), 4.35 (q, J=7 Hz, 2H), 3.93 (m, 4H), 2.86 (m, 1H), 1.96 (m, 2H), 1.36 (m, 12H), 1.16 (m, 2H), 0.98 (m, 2H).

B.

7-[(1α,5α,6α]-6-Amino-3-azabicyclo[3.1.0]hex-3-yl)-1-cyclopropl-6-fluoro-1,4-dihydro-4-oxo-1,8-naphthyridine-3-carboxylic acid, methanesulfonic acid salt The compound of step A was hydrolyzed according to the procedure of Example 25.B. The resulting material was triturated with acetone to provide a white powder, mp>275° C. (88% yield). $^1$H NMR (D 0): 8.47 (s, 1H), 7.73 (d, J=12.3 Hz, 1H), 4.16 (s, 4H), 3.65 (m, 1H), 2.96 (t, J=7.5 Hz, 1H), 2.73 (s, 3H), 2.23 (d, J=7.5 Hz, 2H), 1.27 (m, 2H), 1.02 (m, 2H).

EXAMPLE 33

A.

7-[(1α,2β,5α,6α]-6-tert-Butoxycarbonylamino]-2-methyl-3-azabicyclo]3.1.0]hex-3-yl)-1-cyclopropyl-6-fluoro-1,4-dihydro-4-oxo-1,8-naphthyridine-3-carboxylic acid, ethyl ester

[1α,2β,5α,6α]-6-tert-Butoxycarbonylamino)-2-methyl-3-azabicyclo[3.1.0]hexane and the ethyl ester of 7-chloro-1-cyclopropyl-6-fluoro-1,4-dihydro-4-oxo-1,8-naphthyridine-3-carboxylic acid were reacted according to the procedure of Example 20.A. The title product was obtained as a solid, mp 206°–209° C. with decomposition (65% yield).

$^1$H NMR (CDCl$_3$): 8.47 (s, 1H), 8.05 (d, J=12.9 Hz, 1H), 4.71 (bs, 1H), 4.55 (m, 1H), 4.35 (q, J=7.4 Hz, 2H), 4.20 (m, 1H), 3.68 (m, 1H), 3.48 (m, 1H), 2.55 (s, 1H), 1.95 (m, 1H), 1.86 (m, 1H), 1.47 (d, J=5.9 Hz, 3H), 1.44 (s, 9H), 1.37 (t, J=7.4 Hz, 3H), 1.18 (m, 2H), 1.01 (m, 2H).

B.

7-[(1α,2β,5α,6α]-6-Amino-2-methyl-3-azabicyclo[3.1.0]-hex-3-yl}-1-cyclopropyl-6-fluoro-1,4-dihydro-4-oxo-1,8-naphthyridine-3-carboxylic acid, methanesulfonic acid salt The compound of step A was hydrolyzed according to the procedure of Example 25.B. The material obtained in this way was crystallized from acetone to provide the title product as a solid, mp>289° C. with decomposition (76% yield).

$^1$H NMR (D20): 8.52 (s, 1H), 7.49 (d, J=12.4 Hz, 1H), 4.65 (m, 1H), 4.15 (m, 1H), 3.96 (m, 1H), 3.61 (m, 1H), 2.79 (m, 4H), 2.42 (m, 1H), 2.33 (m, 1H), 1.48 (d, J=5.7 Hz, 3H), 1.29 (m, 2H), 1.05 (m, 2H).

EXAMPLE 34

A.

7-(1-tert-Butoxycarbonylamino-3-azabicyclo[4.1.0]-hept-3-yl)-6-fluoro-1-(2,4-difluorophenyl)-1,4-dihydro-4-oxo-1,8-naphthyridine-3-carboxylic acid, ethyl ester A solution of 1-tert-butoxycarbonylamino-3-azabicyclo-[4.1.0]heptane (200 mg, 0.94 mmol) and the ethyl ester of 7-chloro-6-fluoro-1-(2,4-difluorophenyl) 1,4-dihydro-4-oxo-1,8-naphthyridine-3-carboxylic acid (327 mg, 0.85 mmol) in acetonitrile (12 ml) was heated at reflux for 3 hours. Solvent was removed in vacuo, and the residue was chromatographed on silica gel (eluant: 50% ethyl acetate/-hexane) to afford the title produce as an off-white solid (423 mg, 0.758 mmol, 88% yield).

$^1$H NMR (CDCl$_3$): 8.33 (s, 1H), 8.02 (d, J=13 Hz, 1H), 7.33 (m, 1H), 7.01 (m, 2H), 4.83 (bs, 1H), 4.35 (q, J=7 Hz, 2H), 4.11 (bd, J=13 Hz, 1H), 3.52 (bm, 2H), 3.09 (bm, 1H), 1.99 (bm, 1H), 1.40 (s, 9H), 1.35 (t, J=7 Hz, 3H), 0.78 (dd, J=12,6 Hz, 1H), 0.42 (t, J=4 Hz, 1H).

B.

7-(1-Amino-3-azabicyclo[4.1.0]hept-3-yl)-6-fluoro-1-(2,4-difluorophenyl)-1,4-dihydro-4-oxo-1,8-naphthyridine-3-carboxylic acid, hydrochloride salt A solution of the compound of step A (300 mg, 0.54 mmol) in ethyl acetate (6 ml) and 3N hydrochloric acid (6 ml) was heated to reflux overnight. Solvents were removed in vacuo, and the residue was recrystallized from methanol-acetonitrile to give the title product as a white solid, mp>192° C. (decomp.) (155.5 mg, 0.338 mmol, 62% yield).

$^1$H NMR (DMSO-d$_6$): 8.86 (s, 1H), 8.16 (d, J=13.7 Hz, 1H), 7.80 (m, 1H), 7.60 (m, 1H), 7.34 (m, 1H), 4.04 (dd, J=13.8, 8.2 Hz, 1H), 3.87 (dd, J=13.8, 9.2 Hz, 1H), 3.40 (m, 1H), 3.18 (m, 1H), 1.97 (m, 1H), 1.46 (m, 2H), 1.10 (m, 1H), 0.64 (m, 1H).

EXAMPLE 35

A.

7-(1-tert-Butoxycarbonylamino-3-azabicclo[4.1.0]-hept-3-yl)-1-cyclopropyl-6-fluoro-1,4-dihydro-4-oxo-quinoline-3-carboxylic acid According to the procedure of Example 34A, 1-tert-butoxycarbonylamino-3-azabicyclo[4.1.0]heptane (270.0 mg, 1.27 mmol) and 1-cyclopropyl-6,7-difluoro-1,4-dihydro-4-oxo-quinoline-3-carboxylic acid (275.6 mg, 1.03 mmol) were reacted to generate the title compound (304.2 mg, 0.666 mmol, 65%).

$^1$H NMR (CDCl$_3$): 8.70 (s, 1H), 7.93 (d, J=13.3 Hz, 1H), 7.28 (m, 1H), 5.03 (bs, 1H), 3.82 (m, 1H), 3.46 (m, 3H), 3.19 (bm, 1H), 2.24 (bm, 1H), 1.93 (bm, 1H), 1.63 (bm, 1H), 1.43 (s, 9H), 1.37 (m, 2H), 1.16 (bs, 2H), 0.94 (dd, J=9.7, 5.5 Hz, 1H), 0.80 (t, J=6.0 Hz, 1H). B. 7-(1-Amino-3-azabicyclo[4.1.0]hept-3-yl)-1-cyclopropyl-6-fluoro-1,4-dihydro-4-oxo-quinoline -3-carboxylic acid, hydrochloride salt According to the procedure of Example 34B, the compound of Step A (287.2 mg, 0.63 mmol) was converted with hydrochloric acid to provide the title compound, mp 235° C. (152.4 mg, 0.387 mmol, 62% yield).

EXAMPLE 36

A.

7-(1-tert-Butoxycarbonylamino-3-azabicyclo[4.1.0]-hept-3-yl)6-fluoro-1-(2,4-difluorophenyl)-1,4-dihydro-4-oxo-quinoline-3-carboxylic acid, ether ester According to the procedure of Example 34A, 1-tert-butoxycarbonylamino-3-azabicyclo[4.1.0]heptane (270.0 mg, 1.27 mmol) and 6,7-difluoro-1-(2,4-difluorophenyl)-1,4-dihydro-4-oxo-quinoline-3-carboxylic acid, ethyl ester (463.6 mg, 1.27 mmol) were reacted to generate the tile compound (333.3 mg, 0.59 mmol, 47% yield).

H NMR (CDCl$_3$): 8.24 (s, 1H), 7.92 (d, J=14 Hz, 1H), 7.54 (m, 1H), 7.13 (m, 2H), 6.03 (m, 1H), 4.99 (bs, 1H), 4.31 (q, J=7 Hz, 2H), 3.46 (m, 1H), 3.14 (m, 2H), 2.86 (m, 1H). 2.09 (bm, 1H), 1.77 (m, 1H), 1.38 (m, 13H), 0.84 (dd, J=9, 6 Hz, 1H), 0.71 (m, 1H).

B.

7-(1-Amino-3-azabicyclo[4.1.0]hept-3-yl)-6-fluoro-1-(2,4-difluorophenyl)-1,4-dihydro-4-oxo-quinoline-3-carboxylic acid, hydrochloride salt According to the procedure of Example 34B, the compound of Step B (333.3 mg, 0.59 mmol) was converted with hydrochloric acid to provide the title product, mp 223° C. (decomp), (128.5 mg, 0.276 mmol, 47% yield).

$^1$H NMR (DMSO-d$_6$): 8.84 (s, 1H), 7.98 (d, J=13.5 Hz, 1H), 7.93 (m, 1H), 7.75 (m, 1H), 7.46 (m, 1H), 6.22 (d, J=7.3 Hz, 1H), 3.62 (d, J=12.3 Hz, 1H), 3.40 (dd, J=12.3, 3 Hz, 1H), 3.15 (m, 1H), 2.93 (m, 1H), 1.63 (m, 1H), 1.52 (m, 1H), 1.14 (dd, J=10.4, 5.7 Hz, 1H), 0.71 (m, 1H).

EXAMPLE 37

A.

7-([1α,5α,6α]-5-tert-Butoxycarbonylamino-3-azabicyclo[4.1.0]hept-3-yl)-6-fluoro-1-(2,4-difluorophenyl)-1,4-dihydro-4-oxo-1,8-naphthyridine-3-carboxylic acid, ethyl ester According to the procedure of Example 34A, [1α,5α,6α]-5-tert-butoxycarbonylamino-3-azabicyclo-[4.1.0]heptane (122 mg, 0.57 mmol) and the ethyl ester of 7-chloro-6-fluoro-1-(2,4-difluorophenyyl)-1,4-dihydro-4-oxo-1,8-naphthyridine-3-carboxylic acid (218 mg, 0.57 mmol) were reacted to generate the title product (205 mg, 0.367 mmol, 64% yield).

$^1$H NMR (CDCl$_3$): 8.36 (s, 1H), 8.09 (d, J=13.8 Hz, 1H), 7.37 (m, 1H), 7.05 (m, 2H), 4.75 (m, 1H), 4.36 (q, J=7 Hz, 2H), 3.87 (m, 2H), 3.46 (m, 2H), 3.20 (m, 1H), 1.43 (s, 9H), 1.36 (t, J=7 Hz, 3H), 1.08 (m, 2H), 0.73 (m, 1H), 0.24 (m, 1H).

B.

7-([1α,5α,6α]-5-Amino-3-azabicyclo[4.1.0]hept-3-yl1)-6-fluoro-1-(2,4-difluorophenyl)-1,4-dihydro-4-oxo-1,8-naphthyridine-3-carboxylic acid, hydrochloride salt According to the procedure of Example 34B, the compound of Step A (155 mg, 0.27 mmol) was converted with hydrochloric acid to provide the title product, mp 200°-210° C. (decomp) (50.1 mg, 0.11 mmol, 40% yield).

$^1$H NMR (D$_2$O): 8.83 (bs, 1H), 7.88 (bm, 1H), 7.60 (bm, 1H), 7.29 (bm, 2H), 3.9–3.6 (m, 5H), 1.38 (bm, 1H), 1.24 (bm, 1H), 0.92 (bm, 1H), 0.42 (bm, 1H).

EXAMPLE 38

A.

7-([1α,5α,6α]-5-tert-Butoxycarbonylamino-3-azabicyclo[4.1.0]hept-3-yl)-1-cyclopropyl-6-fluoro-1,4-dihydro-4-oxo-1,8-naphthyridine-3-carboxylic acid, ethyl ester According to the procedure of Example 34A, 1α,5α,6α]-5-tert-butoxycarbonylamino-3-azabicyclo-[4.1.0]heptane (150 mg, 0.7 mmol) and the ethyl ester of 7-chloro-1-cyclopropyl-6-fluoro-1,4-dihydro-4-oxo-1,8-naphthyridine-3-carboxylic acid (217.3 mg, 0.7 mmol) were reacted to generate the title product (230 mg, 0.47 mmol, 67% yield).

$^1$H NMR (CDC13): 8.47 (s, 1H), 8.06 (d, J=13.2 Hz, 1H), 5.33 (bs, 1H), 4.35 (q, J=7.3 Hz, 2H), 4.20 (m, 1H), 4.11 (m, 1H), 3.79 (m, 2H), 3.55–3.35 (m, 2H), 1.41 (s, 9H), 1.37 (t, J=7.3 Hz, 3H), 1.21 (m, 4H), 0.98 (m, 2H), 0.81 (m, 1H), 0.34 (m, 1H).

B.

7-([1α,5α,6α]-5-Amino-3-azabicyclo[4.1.0]-hept-3-yl)-1-cyclopropyl-6-fluoro-1,4-dihydro-4-oxo-1,8-nahthyridine-3-carboxylic acid, mesylate salt According to the procedure of Example 34B, the compound of Step A (220 mg, 0.45 mmol) was converted with methanesulfonic acid in dioxane (15 ml) and water (15 ml) to provide the title compound, mp>260° C. (153.8 mg, 0.339 mmol, 75% yield).

$^1$H NMR (D$_2$O): 8.58 (s, 1H), 7.72 (d, J=12.6 Hz, 1H), 4.33 (bm, 1H), 4.08–3.84 (m, 5H), 2.81 (s, 3H), 1.55 (m, 1H), 1.33 (bs, 3H), 1.07 (bs, 3H), 0.60 (bs, 1H).

EXAMPLE 39

A.

7-([1α,5α,6α]-5-tert-Butoxycarbonylamino-3-azabicyclo[4.1.0]hept-3-yl)-1-cyclopropyl-6-fluoro-1,4-dihydro-4-oxo-quinoline-3-carboxylic acid According to the procedure of Example 34A, [1α,5α,6α]-5-tert-butoxycarbonylamino-3-azabicyclo[4.1.0-]heptane (187.8 mg, 0.88 mmol) and 1-cyclopropyl-6,7-difluoro-1,4-dihydro-4-oxo-quinoline-3-carboxylic acid (210 mg, 0.79 mmol) were reacted to generate the title product, mp 167° C. (195 mg, 0.426 mmol, 48% yield).

B.

7-([1α,5α,6α]-5-Amino-3-azabicyclo[4.1.0]hept-3-y1)-1-cyclopropyl-6-fluoro-1,4-dihydro-4-oxo-quinoline-3-carboxylic acid, hydrochloride salt According to the procedure of Example 34B, the compound of step A (195 mg, 0.43 mmol) was converted with hydrochloric acid to provide the title product, mp 210° C. (decomp.) (113.4 mg, 0.289 mmol, 67% yield).

$^1$H NMR (D$_2$O): 8.53 (bs, 1H), 7.47 (m, 2H), 4.00 (bs, 1H), 3.88 (m, 1H), 3.68–3.40 (m, 3H), 3.21 (m, 1H), 1.62 (m, 1H), 1.44 (m, 2H), 1.37 (m, 1H), 1.18 (m, 2H), 1.09 (m, 1H), 0.73 (m, 1H).

EXAMPLE 40

A.

7-([1α,5α,6α]-5-tert-Butoxycarbonylamino-3-azabicyclo[4.1.0]hept-3-yl)-1-cyclopropyl-6,8-difluoro-1,4-dihydro-4-oxo-quinoline-3-carboxylic acid According to the procedure of Example 34A, [1α,5α,6α]bicyclo[4 1.0]-5-tert-butoxycarbonylamino-3- azabicyclo[4.1.0]-heptane (200 mg, 0.94 mmol) and 1-cyclopropyl-6,7,8-trifluoro-1,4-dihydro-4-oxo-quinoline-3-carboxylic acid (313 mg, 0.94 mmol) were reacted to generate the title product (290 mg, 0.61 mmol, 65% yield).

1H NMR (CDCl$_3$): 8.74 (s, 1H), 7 84 (d, J=11.6 Hz, 1H), 4.98 (m, 1H), 4.04 (m, 1H), 3.93 (m, 1H), 3.70 (dd, J=12.3, 5.6 Hz, 1H), 3.40 (d, J=12.3 Hz, 1H), 3.32 (m, 1H), 2.89 (m, 1H), 1.39 (s, 9H), 1.24 (m, 2H), 1.12 (m, 2H), 1.04 (m, 1H), 0.79 (m, 1H), 0.51 (m, 1H), 0.29 (m, 1H).

B.

7-([1α,5α,6α]-5-Amino-3-azabicyclo[4.1.0]hept-3-yl)-1-cyclopropyl-6,8-difluoro-1,4-dihydro-4-oxo-quinoline-3-carboxylic acid, mesylate salt According to the procedure of Example 34B, the compound of step A (290 mg, 0.61 mmol) was converted with methanesulfonic acid in dioxane (10 ml) and water (10 ml) to provide the title product, mp>250° C. (51.1 mg, 0.11 mmol, 18% yield).

1H NMR (D$_2$O-NaOH): 8.50 (s, 1H), 7.66 (d, J=12.4 Hz, 1H), 4.01 (m, 1H), 3.68 (m, 1H), 3.45 (d, J=11.6 Hz, 1H), 3.30 (d, J=11.6 Hz, 1H), 3.22 (m, 1H), 2.83 (s, 3H), 2.79 (m, 1H), 1.23 (m, 2H), 1.10 (m, 2H), 0.98 (m, 1H), 0.74 (m, 1H), 0.46 (m, 1H), 0.22 (m, 1H).

EXAMPLE 41

A.

7-([1α,5α,6α]-5-tert-Butoxycarbonylamino-3-azabicyclo[4.1.0]hept-3-Yl)-5-amino-1-cyclopropyl-6,8-difluoro-1,4-dihydro-4-oxo-quinoline-3-carboxylic acid According to the procedure of Example 34A, [1α,5α,6α]-5-tert-butoxycarbonylamino-3-azabicyclo[4.1.0]heptane (110 mg, 0.52 mmol) and 5-amino-1-cyclopropyl-6,7,8-trifluoro-1,4-dihydro-4-oxo-quinoline-3-carboxylic acid (140 mg, 0.46 mmol) were reacted in dimethylsulfoxide to generate the title product (220 mg, 0.45 mmol, 98% yield).

1H NMR (DMSO-d$_6$): 8.48 (s, 1H), 7.25 (bs, 1H), 7.10 (d, J=7 Hz, 1H), 4.00 (m, 1H), 3.72 (m, 1H), 3.61 (bd, J=10 Hz, 1H), 3.47 (d, J=12 Hz, 1H), 2.76 (t, J=10 Hz, 1H), 1.38 (s, 9H), 1.16 (m, 1H), 0.97 (m, 1H), 0.69 (m, 1H), 0.35 (m, 1H).

A.

7-([1α,5α,6α]-5-Amino-3-azabicyclo[4.1.0]hept-3-yl)-5-amino-1-cyclopropyl-6,8-difluoro-1,4-dihydro-4-oxo-quinoline-3-carboxylic acid, hydrochloride salt According the the procedure of Example 34B, the compound of step A (220 mg, 0.45 mmol) was converted with hydrochloric acid to provide the title product, mp>238° C. (76.5 mg, 0.18 mmol, 40% yield).

1H NMR (DMSO-d$_6$/D$_2$O): 8.50 (s, 1H), 3.99 (m, 1H), 3.62 (m, 1H), 3.47 (m, 2H), 3.01 (m, 2H), 1.32 (m, 1H), 1.07 (m, 5H), 0.81 (m, 1H), 0.53 (m, 1H).

EXAMPLE 42

A.

7-([1α,5β,6α]-5-tert-Butoxycarbonylamino-3-azabicyclo[4.1.0]hept-3-yl)-6-fluoro-1-(2,4-difluorophenyl)-1,4-dihydro-4-oxo-1,8-naphthyridine-3-carboxylic acid, ethyl ester According to the procedure of Example 34A, [1α,5β,6α]-5-tert-butoxycarbonylamino-3-azabicyclo[4.1.0]heptane (212 mg., 1.0 mmol) and the ethyl ester of 7-chloro-6-fluoro-1-(2,4-difluorophenyl)-1,4-dihydro-4-oxo-1,8-naphthyridine-3-carboxylic acid (363.3 mg, 0.95 mmol) were reacted to generate the title product (389 mg, 0.70 mmol, 73% yield).

1H NMR (CDCl$_3$): 8.35 (s, 1H), 8.08 (d, J=13 Hz, 1H), 7.35 (m, 1H), 7.05 (m, 2H), 4.58 (m, 1H), 4.36 (q, J=7 Hz, 2H), 4.05 (m, 1H), 3.80 (m, 1H), 3.45 (m, 1H), 3.30 (m, 1H), 1.44 (bs, 10H), 1.38 (t, J=7 Hz, 3H), 1.22 (m, 1H), 0.54 (m, 1H), 0 26 (m, 1H).

B.

7-([1α,5β,6α]-5-Amino-3-azabicyclo[4.1.0]hept-3-yl)-6-fluro-1-(2,4-difluorophenyl)-1,4-dihYdro-4-oxo-1,8-naphthyridine-3-carboxylic acid, hydrochloride salt According to the procedure of Example 34B, the compound of step A (383.4 mg, 0.68 mmol) was converted with hydrochloric acid to provide the title product, mp>200° C. (173.1 mg, 0.377 mmol, 55% yield).

1H NMR (D$_2$0): 8.85 (s, 1H), 7.95 (d, J=12.8 Hz, 1H), 7.60 (m, 1H), 7.32 (m, 2H), 4.03 (m, 1H), 3.96–3.73 (m, 2H), 3.53 (m, 2H), 1.55 (m, 1H), 1.46 (m, 1H), 0.84 (m, 1H), 0.56 (m, 1H).

EXAMPLE 43

A.

7-([1α,5β,6α]-5-tert-Butoxycarbonylamino-3-azabicyclo[4.1.0]hept-3-yl)-1-cyclopropyl-6-fluoro-1,4-dihydro-4-oxo-quinoline-3-carboxylic acid According to the procedure of Example 34A, [1α,5β,6α]-5-tert-butoxycarbonylaino-3-azabicyclo[4.1.0]heptane (133 mg, 0.62 mmol) and 1-cyclopropyl-6,7-difluoro-1,4-dihydro-4-oxo-quinoline-3-carboxylic acid (164 mg, 0.62 mmol) were reacted to generate the title product (99.6 mg, 0.218 mmol, 35% yield).

1H NMR (CDCl$_3$) 8.72 (s, 1H), 7.96 (d, J=13.3 Hz, 1H), 7.38 (d, J=7.2 Hz, 1H), 4.82 (bd, J=7.6 Hz, 1H), 4.28 (m, 1H), 3.58 (m, 3H), 3.30 (m, 1H), 3.12 (m, 1H), 1.44 (m, 13H), 1.15 (m, 2H), 0.71 (m, 1H), 0.62 (m, 1H).

B.

7-([1α,5β,6α]-5-Amino-3-azabicyclo[4.1.0]hept-3-yl)-1-cyc 1-6-fluoro-1,4-dihydro-4-oxo-quinoline-3-carboxylic acid, hydrochloride salt According to the procedure of Example 34B, the compound of step A (99 mg, 0.21 mmol) was converted with hydrochloric acid to provide the title product, mp 252° C. (decomp.) (32 mg, 0.081 mmol, 38% yield).

1H NMR (DMSO-d$_6$): 8.71 (s, 1H), 8.39 (bs, 2H), 7.97 (d, J=13 Hz, 1H), 7.62 (bs, 1H), 4.0-3.2 (m, 6H), 1.57 (m, 2H), 1.41 (m, 2H), 1.24 (m, 2H), 1.00 (m, 1H), 0.81 (m, 1H).

EXAMPLE 44

A.

7-([1α,6α,7α]-7-tert-Butoxycarbonylamino-3-azabicyclo[4.1.0]hept-3-yl)-6-fluoro-1-(2,4-difluorophenyl)-1,4-dihydro-4-oxo-1,8-naphthyridine-3-carboxylic acid, ethyl ester According to the procedure of Example 34A, (1α,6α,7α]-7-tert-butoxycarbonylamino-3-azabicyclo[4.1.0]heptane (300 mg, 1.41 mmol) and the ethyl ester of 7-chloro-6-fluoro-1-(2,4-difluorophenyl)-1,4-dihydro-4-oxo-1,8-naphthyridine-3 -carboxylic acid (535.3 mg, 1.40 mmol) were reacted to generate the title product (780 mg, 1.39 mmol, 99%).

¹H NMR (CDCl₃): 8.40 (s, 1H), 8.12 (d, J=13 Hz, 1H), 7.43 (m, 1H), 7.09 (m, 2H), 4.70 (m, 1H), 4.43 (q, J=7 Hz, 2H), 3.92 (d, J=12 Hz, 1H), 3.70 (m, 1H), 3.40 (m, 1H), 3.10 (m, 1H), 2.28 (m, 1H), 1.99 (m, 1H), 1.82 (m, 1H), 1.45 (s, 9H), 1.42 (t, J=7 Hz, 3H), 1.21 (m, 2H).

B.1

7-([1α,6α,7α]-7-Amino-3-azabicyclo[4.1.0]hept-3-yl)-6-fluoro-1-(2,4-difluorophenyl)-1,4-dihydro-4-oxo-1,8-naphthyridine-3-carboxylic acid, hydrochloride salt According to the procedure of Example 34B, the compound of step A (283 mg, 0.51 mmol) was converted with hydrochloric acid to provide the title product, mp 204° C. (decomp.) (150 mg, 0.322 mmol, 63% yield).

¹H NMR (D₂O): 8.81 (s, 1H), 7.76 (d, J=13.5 Hz, 1H), 7.57 (m, 1H), 7.29 (m, 2H), 4.01 (d, J=14.9 Hz, 1H), 3.81 (bd, J=13.3 Hz, 1H), 3.45 (m, 1H), 3.20 (m, 1H), 2.50 (bs, 1H), 2.05 (m, 1H), 1.79 (m, 1H), 1.61 (bs, 2H).

B.2

7-([1α,6α,7α]-7-Amino-3-azabicyclo[4.1.0]hept-3-yl)-6-fluoro-1-(2,4-difluorophenyl)-1,4-dihydro-4-oxo-1,8-naphthyridine-3-carboxylic acid, mesylate salt According to the procedure of Example 34B, the compound of step A (770 mg, 1.37 mmol) was converted with methanesulfonic acid in dioxane (10 ml) and water (10 ml) to provide the title product, mp>219° C. (decomp.) (249.5 mg, 0.474 mmol, 35% yield).

¹H NMR (D₂O-NaOH): 8.35 (s, 1H), 7.93 (d, J=13.4 Hz, 1H), 7.54 (m, 1H), 7.24 (m, 2H), 3.85-3.60 (m, 2H), 3.33 (m, 1H), 3.06 (m, 1H), 2.85 (s, 3H), 1.95 (m, 2H), 1.63 (m, 1H), 1.00 (bs, 2H).

EXAMPLE 45

A. 7-([1α,6α,7α]-7-tert-Butoxycarbonylamino-3-azabicyclo[4.1.0]hept-3yl)-1-cyclopropyl-6-fluoro-1,4-dihydro-4-oxo-1,8-naphthyridine-3-carboxylic acid ethyl ester According to the procedure of Example 34A, [1α,-6α,7α]-7-tert-butoxycarbonylamino-3-azabicyclo[4.1.0-]heptane (325 mg, 1.53 mmol) and the ethyl ester of 7-chloro-1-cyclopropyl-6-fluoro-1,4-dihydro-4-oxo-1,8-naphthyridine-3 -carboxylic acid (402 mg, 1.29 mmol) were reacted to generate the title product (609 mg, 1.25 mmol, 97% yield).

¹H NMR (CDCl₃): 8.44 (s, 1H), 8.02 (d, J=13 Hz, 1H), 4.77 (bs, 1H), 4.35 (q, J=7 Hz, 2H), 4.25 (d, J=13 Hz, 1H), 3.92 (m, 1H), 3.65 (m, 1H), 3.48 (m, 1H), 3.27 (m, 1H), 2.34 (m, 1H), 2.10 (m, 1H), 1.95 (m, 1H), 1.40 (s, 9H), 1.37 (t, J=7 Hz, 3H), 1.26 (m, 2H), 1.19 (m, 2H), 0.99 (m, 2H).

B.

7-([1α,6α,7α]-7-Amino-3-azabicyclo[4.1.0]hept-3-yl)-1 cyclopropyl-6-fluoro-1,4-dihydro-4-oxo-1,8-naphthyridine-3-carboxylic acid, hydrochloride salt According to the procedure of Example 34B, the compound of step A (585 mg, 1.20 mmol) was converted with hydrochloric acid to provide the title product, mp 180° C. (decomp.) (265.7 mg, 0.675 mmol, 56% yield).

¹H NMR (DMSO-d₆): 8.58 (s, 1H), 8.40 (bs, 2H), 8.02 (d, J=13.6 Hz, 1H), 4.19 (d, J=14.1 Hz, 1H), 4.06 (dd, J=13.8, 5.2 Hz, 1H), 3.73 (m, 2H), 3.37 (m, 2H), 2.49 (m, 1H), 2.16 (m, 1H), 1.84 (m, 1H), 1.66 (m, 1H), 1.58 (m, 1H), 1.19 (m, 2H), 1.10 (m, 2H).

EXAMPLE 46

A.

7-([1α,5α,6α]-6-(N-Benzyloxycarbonyl-L-Ala-L-Leu -amino)-3-azabicyclo[3.1.0]hex-3-yl)-6-fluoro-1-2,4-difluorophenyl)-1,4-dihydro-4-oxo-1,8-naphthyridine-3-carboxylic acid 7-([1α,5α,6α]-6-Amino-3-azabicyclo[3.1.0]hex-3-yl)-6-fluoro-1-(2,4-difluorophenyl)-1,4-dihydro-4-oxo-1,8-naphthyridine-3-carboxylic acid, methanesulfonate salt (400 mg, 0.78 mmol) was mixed with methylene chloride (50 ml) and treated with N-benzyloxycarbonyl-L-alanine-L-leucine (290 mg, 0.86 mmol), 1-(3-dimethylaminopropyl) -3-ethylcarbodiimide hydrochloride (175 mg, 0.91 mmol), 1-hydroxybenzotriazole hydrate (135 mg, 1.0 mmol) and triethylamine (0.20 ml, 1.4 mmol). After stirring for 16 hours at room temperature, the mixture was treated with hydrochloric acid (1N, 30 ml) and extracted with methylene chloride. After drying over sodium sulfate, the organic layers were filtered and concentrated to a residue, which was recrystallized from chloroform-methanol to provide the title product as a solid, mp>214°-216° C. (468 mg, 0.63 mmol, 81% yield).

¹H NMR (CDCl₃-CD₃OD): 8.58 (s, 1H), 7.97 (d, J=12.4 Hz, 1H), 7.28 (m, 6H), 7.04 (m, 2H), 5.04 (s, 2H), 4.20 (m, 1H), 4.07 (q, J=7.1 Hz, 1H), 2.32 (s, 1H), 1.75 (m, 2H), 1.5 (m, 3H), 1.28 d, J=7.1 Hz, 3H), 0.83 (m, 6H).

B.

7-[1α,5α,6α]-6-(L-Ala-L-Leu-amino)-3-azabicyclo-[3.1.0]hex-3-y1)-6-fluoro-1-(2,4-difluorcphenyl)-1,4-dihydro-4-oxo-1,8-naphthyridine-3-carboxlic acid, hydrochloride salt The title compound of Example 46A (250 mg, 0.34 mmol) was dissolved in acetic acid (50 ml), treated with palladium on carbon (125 mg) and hdrogenated at 50 psi for 16 hours. The catalyst was remcvd by filtration and the filtrate treated with hydrochloric acid (6N, 5 ml). Concentration in vacuo provided a r° sidue which was then recrystalized frcm isopropanol. The resulting solid was washed with acetce and ether to provide the title product as a pale tan solid, mp>242° C. with decomposition (96 mg, 0.15 mmol, 44% yield).

¹H NMR (DMSO-d₆): 8.82 (s, 1H), 8.52 (m, 1H), 8.33 (bs, 1H), 8.15 (bm, 1H), 8.07 (d, J=12.6 Hz, 1H), 7.81 (m, 1H), 7.63 (m, 1H), 7.35 (m, 1H), 4.21 ;m, 1H), 3.82 (m, 1H), 3.7 (vbm, 4H), 2.37 (s, 1H), 1.77 (bs, 2H), 1.51 (m, 3H), 1.32 (d, J=6.6 Hz, 3H), 0.86 (m, 6H).

EXAMPLE 47

A. 7-([1α,5α,6α]-6-(N-Benzvloxycarbonyl-Gly-L-Phe -amino)-3-azabicyclo[3.1.0]hex-3-yl)-6-fluoro-1-(2,4-difluorophenyl)-1,4-dihydro-4-oxo-1,8-naphthyridine-3-carboxylic acid 7-([1α,5α,6α]-6-Amino-3-azabicyclo[3.1.0]hex-3-yl)-6-fluoro-1-(2,4-difluorophenyl)-1,4-dihydro-4-oxo-1,8-naphthyridine-3-carboxylic acid, hydrochloride salt (454 mg, 1.0 mmol) was racted with N-benzyloxycarbonyl-glycine-L-phenylalanine (450 mg, 1.2 mmol) according to the procedure of Example 46A, except that an additional equivalent of trithylamine was utilized, and the extraction was effected with chloroform. Recrystallization of the crude product from chloroform-ether provided the title product as a white solid, mp > 209°–211° C. with decomposition (516 mg, 0.68 mmol, 68% yield).

¹H NMR (CDCl₃): 8.59 (s, 1H), 7.95 (d, J=12.3 Hz, 1H), 7.26 (m, 15H), 6.84 (bs, 1H), 5.86 (bs, 1H), 5.03 (s, 2H), 4.61 (m, 1H), 3.79 (bs, 2H), 3.6 (vbm, 4H), 3.01 (bs, 2H), 2.32 (s, 1H), 1.63 (s, 2H).

B.

7-([1α,5α,6α]-6-(Gly-L-Phe-amino)-3-azabicyclo-[3.1.0]hex-3-yl)-6-fluoro-1-(2,4-difluorophenyl)-1,4-dihydro-4-oxo-1,8-naphthyridine-3-carboxylic acid, hydrochloride salt The title product of Example 47A (235 mg, 0.35 mmol) was hydrogenated according to the procedure of Example 46B. The residue obtained upon concentration of the acidified reaction mixture was triturated with isopropanol-ether and filtered to give a solid which was then slurried in hot isopropanol. Filtration provided the title product as a solid, mp > 275° C. (38 mg, 0.058 mmol, 16% yield)

¹H NMR (DMSO-d₆D₂O): 8.78 (s, 1H), 8.04 (d, J=12.5 Hz, 1H), 7.76 (m, 1H), 7.57 (m, 1H), 7.33 (m, 1H), 7.20 (m, 5H), 4.40 (dd, J=5.6, 9.2 HZ, 1H), 3.50 (m, 6H), 2.90 (dd, J=5.6, 13.6 Hz, 1H), 2.74 (dd, J=9.3, 13.4 Hz, 1H), 2.28 (s, 1H), 1.67 (bs, 2H).

EXAMPLE 48

A.

7-([1α,5α,6α]-6-(N-tert-Butoxycarbonyl-L-Ala-amino)-3-azabicyclo[3.1.0]hex-3-yl)-6-fluoro-1-(2,4-difluorophenyl)-1,4-dihydro-4-oxo-1,8-naphthyridine-3-carboxylic acid 7-([1α,5α,6α]-6-Amino-3-azabicyclo[3.1.0]hex-3-yl)-6-fluoro-1-(2,4-difluorophenyl)-1,4-dihydro-4-oxo-1,8-naphthridine-3-carboxylic acid, hydrochloride salt (500 mg, 1.1 mmol) was mixed with methylene chloride (60 ml) and reacted with N-tert-butoxycarbonyl-L-alanine (250 mg, 1.32 mmol) according to the procedure of Example 46A, except that an additional equivalent of triethylamine was used. The crude product was purified by column chromatography (eluant: 89:10:1 chloroform: mehtanol: concentrated ammonium hydroxide) to provide the title product as a solid, mp 228°–230 ° C. (426 mg, 0.72 mmol, 66% yield).

¹H NMR (CDCL ): 8.61 (s, 1H), 8.02 (d, J=12.1 Hz, 7.34 (m, 1H), 7.06 (m, 2H), 6.45 (bs, 1H), 4.81 (bs, 1H), 4.03 (m, 1H), 3.8 (vbm, 4H), 2.39 (s, 1H), 1.78 (s, 2H), 1.41 (s, 9H), 1.29 (d, J=7.4 Hz, 3H).

B.

7-([1α,5α,6α]-6-(1-Ala-amino)-3-azabicyclo[3.1.0]hex-3-yl)-6-fluoro-1-(2,4-difluorophenyl)-1,4-dihydro-4-oxo-1,8-naphthyridine-3-carboxylic acid, hydrochloride salt The title product of Example 48A (325 mg, 0.58 mmol) was dissolved in dioxane (10 ml) and treated with a solution of hydrochloric acid in dioxane (4M, 1 ml). After stirring at 6.5 hours at room temperature, the reaction mixture was concentrated in vacuo, and the residue recrystall;-zed from isopropanol-methanol to provide the title product as a white powder, mp 236°–238° C. (204 mg, 0.4 mmol, 69% yield).

¹H NMR (DMSO-d₆-D₂O, 87° C.:, 8.70 (s, 1H), 8.01 (d, J=12.7 Hz, 1H), 7.75 (m, 1H), 7.49 (m, 1H), 7.31 (m, 1H), 3.74 (bdd, J=2.9, 12.1 Hz, 2H), 3.7 (m, 1H), 3.61 (bd, J=12.0 Hz, 2H), 2.34 (m, 1H), 1.82 (bs, 2H), 1.11 (d, J=6.8 Hz, 3H).

EXAMPLE 49

A.

7-([1α,5α,6α]-6-(N-tert-Butoxycarbonyl-L-Ala-L-Ala-amino)-3-azabicyclo[3.1.0]hex-3-yl)-6-fluoro-1-(2,4 di-fluorophenyl)-1,4-dihydro-4-oxo-1,8-naphthyridine-3-carboxylic acid The title product from Example 48B (345 mg, 0.68 mmol) was mixed with methylene chloride (40 ml) and reacted with N-tert-butoxycarbonyl-L-alanine (140 mg, 0.75 mmol) according to the procedure of Example 46A. The crude product was purified by column chromatography (eluant: 80:20:1 chloroform: methanol: concentrated ammonium hydroxide) to provide material which was then recrystallized from ethyl acetate-ether. The title product was obtained as a solid, mp > 275° C. (182 mg, 0.28 mmol, 41% yield).

¹H NMR (DMSO-d₆): 8.80 (s, 1H), 8.03 (d, J=12.9 Hz, 1H), 7.98 (bs, 1H), 7.79 (m, 2H), 7.61 (m, 1H), 7.34 (m, 1H), 6.99 (bd, J=6.7 Hz, 1H), 4.12 (m, 1H), 3.90 (m, 1H), 3.64 (vbm, 4H), 2.34 (bs, 1H), 1.74 (bs, 2H), 1.36 (s, 9H), 1.14 (m, 6H).

Alternatively, the title product can be prepared by reaction of 7-chloro-6-fluoro-1-(2,4-difluorophenyl)-1,4-dihydro-4-oxo-1,8-naphthyridine-3-carboxylic acid (180 mg, 0.51 mmol) with [1α,5α,6α]-6-(N-tert-butoxycarbonyl-L-Ala-L-Ala-amino)-3-azabicyclo[3.1.0]hexane (340.4 mg, 0.56 mmol) in triethylamine (1 ml) and acetonitrile (10 ml). This mixture was stirred at room temperature for 18 hours, at which point solvent was removed in vacuo, and the residue partitioned between chloroform and water. The organic layer was dried over magnesium sulfate, filtered and concentrated to provide the title product (308 mg, 0.47 mmol, 84% yield).

B.

7-[1α,5α,6α]-6-(L-Ala-L-Ala-amino)-3-azabicyclo-[3.1.0]hex-3-yl)-6-fluoro-1-(2,4-difluorophenyl)-1,4-dihydro-4-oxo-1,8-naphthyridine-3-carboxylic acid, hydrochloride salt The title product of Example 49A (150 mg, 0.23 mmol) was mixed with dioxane (22 ml) and a hydrochloric acid solution (3N in dioxane, 2.5 ml) and allowed to stir at room temperature for 18 hours. Removal of solvent in vacuo provided a residue which was recrystallized from isopropanol-methanol to provide the title product as a white solid, mp > 275° C. (102 mg, 0.17 mmol, 75% yield).

¹H NMR (DMSO-d₆-D₂O, 87° C.): 8.66 (s, 1H), 7.99 (d, J=12.6 Hz, 1H), 7.68 (m, 1H), 7.40 (m, 1H), 7.26 (m, 1H), 4.18 (m, 1H), 3.84 (q, J=7.0 Hz, 1H), 3.72 (bd, J=10.6 Hz, 2H), 3.58 (bd, J 11.0 Hz, 2H), 2.29 (s, 1H), 1.78 (bs, 2H), 1.37 (d, J=7.0 Hz, 3H), 1.22 (d, J=7.1 Hz, 3H).

C.

7-([1α,5α,6α]-6-(L-Ala-L-Ala-amino)-3-azabicyclo-[3.1.0]hex-3-yl)-6-fluoro-1-(2,4-difluorophenyl)-1,4-dihydro-4-oxo-1,8-naphthydrine-3-carboxylic acid, methane-sulfonic acid salt The title product of Example 49B (2.0 g, 3.4 mmol) was dissolved in water and the solution adjusted to pH 7 by addition of saturated aqueous sodium bicarbonate. The mixture was then extracted with chloroform/methanol. The organic layers were dried over sodium sulfate, filtered and concentrated to provide the free base (1.06 g, 1.9 mmol, 56% for conversion to the free base). A portion of this material (900 mg, 1.61 mmol) was dissolved in acetone (30 ml) and treated with methanesulfonic acid (0.10 ml, 1.5 mmol). The solid which formed was separated by filtration and recrystallized from ethanol to provide the title product as a solid, mp 211°-213° C. (466 mg, 0.71 mmol, 44% yield).

$^1$H NMR (DMSO-$d_6$): 15.12 (s, 1H), 8.82 (s, 1H), 8.52 (d, J=7.3 Hz, 1H), 8.21 (d, J=3.9 Hz, 1H), 8.07 (d, J=12.6 Hz, 1H), 8.02 (m, 2H), 7.80 (m, 1H), 7.63 (m, 1H), 7.35 (m, 1H), 4.21 (m, 1H), 3.83 (m, 1H), 3.64 (bm, 4H), 2.49 (bs, 1H), 2.29 (s, 3H), 1.76 (bs, 2H), 1.32 (d, J=7.0 Hz, 3H), 1.20 (d, J=7.1 Hz, 3H).

I claim:
1. A compound of the formula

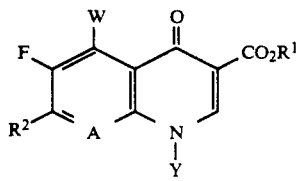

or a pharmaceutically acceptable acid addition salt thereof, wherein $R^1$ is hydrogen, a pharmaceutically acceptable cation, or ($C_1$-$C_6$) alkyl;

W is hydrogen, fluoro, chloro, bromo, $C_1$-$C_4$ alkyl, $C_1$-$C_4$ alkoxy, amino or aminomethyl;

A is carbon and is taken together with Y and the carbon and nitrogen to which A and Y are attached to form a five or six membered ring which may contain oxygen or a double bond, and which may have attached thereto $R^8$ which is methyl or methylene; and R2 is

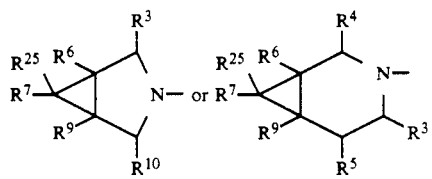

wherein $R^3$, $R^4$, $R^5$, $R^6$, $R^7$, $R^9$, $R^{10}$ and $R^{25}$ are each independently H, $CH_3$, $CH_2NH_2$, $CH_2NHCH_3$ or $CH_2NHC_2H_5$, and $R^5$, $R^6$, $R^7$, and $R^9$ may also independently by $NH_2$, $NHDH_3$ or $NHC_2H_5$, provided that not more than three of $R^3$, $R^4$, $R^5$, $R^6$, $R^7$, $R^9$, $R^{10}$ and $R^{25}$ are other than hydrogen and if three of these substituents are not hydrogen, at least one of them is methyl; and prodrugs of those compounds of formula I having free amino groups.

2. A compound according to claim 1 wherein $R^1$ is hydrogen.

3. A compound according to claim 1 wherein W is hydrogen, and A is CH or N, or A is carbon and is taken together with Y and the carbon and nitrogen to which A and Y are attached to form a six membered ring as follows:

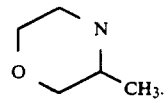

4. A compound according to claim 1 wherein one or two of $R^3$, $R^4$, $R^5$, $R^6$, $R^9$, $R^{10}$ and $R^{25}$ are other than hydrogen.

5. A compound to claim 4 wherein one of $R^3$, $R^4$, $R^5$, $R^6$, $R^7$, $R^9$, or $R^{10}$ is $CH_2NH_2$ or $CH_2NHCH_3$, and, optionally, another of $R^3$, $R^4$, $R^5$, $R^6$, $R^7$, $R^9$, $R^{10}$ or $R^{25}$ is methyl.

6. A compound according to claim 5 wherein one of $R^5$, $R^6$, $R^7$ or $R^9$ is $NH_2$ or $NHCH_3$ and, optionally, another of $R^5$, $R^6$, $R^7$ or $R^9$ or one of $R^3$, $R^4$, $R^{10}$ or $R^{25}$ is methyl.

7. A compound according to claim 6 wherein $R^6$, $R^7$ or $R^9$ is amino and, optionally one of $R^3$, $R^4$, $R^5$, $R^6$, $R^7$, $R^9$, $R^{10}$ or $R^{25}$ is methyl.

8. A compound according to claim 1 wherein $R^7$ is amino and, optionally, one of $R^3$, $R^4$, $R^5$, $R^6$, $R^9$, $R^{10}$ or $R^{25}$ is methyl.

9. A compound according to claim 4 wherein $R^7$ is amino and $R^3$, $R^4$, $R^5$, $R^6$, $R^9$, $R^{10}$ or $R^{25}$ are each hydrogen.

10. A compound according to claim 1 wherein $R^6$, $R^7$ or $R^9$ contains an amino group which is covalently bonded through a peptide bond to one amino acid residue.

11. A compound according to claim 1 wherein $R^6$, $R^7$ or $R^9$ contains an amino group which is covalently bonded through a peptide bond to a polypeptide of two or more amino acids.

12. A compound according to claim 1 wherein $R^6$, $R^7$ or $R^9$ contains an amino group which is covalently bonded through a peptide bond to a polypeptide of two amino acids.

13. A compoudn according to claim 9, wherein the amino group of $R^7$ is covalently bonded through a peptide bond to one amino acid residue.

14. A compound according to claim 9, wherein the amino group of $R^7$ is covalently bonded through a peptide bond to a polypeptide of two or more amino acids.

15. A compound according to claim 9 wherien the amino group of $R^7$ is covalently bonded to a polypeptide of two amino acids.

16. An antibacterial composition comprising an antibacterially effective amount of a compound according to claim 1 and a pharmaceutically acceptable carrier.

17. A method for the treatment of a bacterial infection which comprises administering to a subject affected by a bacterial infection an antibacterially effective amount of a compound according to claim 1.

* * * * *